(12) United States Patent
Lu et al.

(10) Patent No.: US 9,957,511 B2
(45) Date of Patent: May 1, 2018

(54) FUNCTIONALIZATION OF ENDOGENOUS BACTERIA

(71) Applicants: Massachusetts Institute of Technology, Cambridge, MA (US); Trustees of Boston University, Boston, MA (US)

(72) Inventors: Timothy Kuan-Ta Lu, Charlestown, MA (US); Robert James Citorik, Kingston, NH (US); James Collins, Newton, MA (US); Russell-John Krom, Boston, MA (US)

(73) Assignees: Massachusetts Institute of Technology, Cambridge, MA (US); Trustees of Boston University, Boston, MA (US)

( * ) Notice: Subject to any disclaimer, the term of this patent is extended or adjusted under 35 U.S.C. 154(b) by 0 days. days.

(21) Appl. No.: 14/320,965

(22) Filed: Jul. 1, 2014

(65) Prior Publication Data

US 2015/0004705 A1 Jan. 1, 2015

Related U.S. Application Data

(60) Provisional application No. 61/841,904, filed on Jul. 1, 2013.

(51) Int. Cl.
| | | |
|---|---|---|
| C12N 7/00 | (2006.01) | |
| C12N 15/74 | (2006.01) | |
| C12N 15/70 | (2006.01) | |

(52) U.S. Cl.
CPC .......... *C12N 15/74* (2013.01); *C12N 7/00* (2013.01); *C12N 15/70* (2013.01); *C12N 2795/14132* (2013.01); *C12N 2795/14143* (2013.01); *C12N 2795/14171* (2013.01); *C12N 2830/55* (2013.01)

(58) Field of Classification Search
None
See application file for complete search history.

(56) References Cited

U.S. PATENT DOCUMENTS

| | | | |
|---|---|---|---|
| 7,763,420 B2 * | 7/2010 | Stritzker | A61K 33/24 424/234.1 |
| 2003/0165877 A1 | 9/2003 | Muyldermans et al. | |
| 2009/0010872 A1 * | 1/2009 | Mackiewicz | C07K 14/7155 424/85.2 |
| 2010/0011456 A1 * | 1/2010 | Mathur | C12N 9/00 800/15 |
| 2013/0122549 A1 | 5/2013 | Lu et al. | |

FOREIGN PATENT DOCUMENTS

| | | |
|---|---|---|
| EP | 1073671 A1 | 2/2001 |
| WO | WO 99/55720 A1 | 11/1999 |
| WO | WO 00/61804 A1 | 10/2000 |
| WO | WO 2004/007695 A2 | 1/2004 |

OTHER PUBLICATIONS

Lu et al. 2009 (Engineered bacteriophage targeting gene networks as adjuvants for antibiotic therepy; PNAS 106(12): 4629-4639).*
Yacoby et al. 2008 (Targeted filamentous bacteriophages as therapeutic agents; Expert Opin. Drug Deliv. 5(3):321-329).*
Reyes et al. 2012 (Going viral: next-generation sequencing applied to phage populations in the human gut; Nature Reviews Microbiology 10:607-617).*
Lu et al. 2011 (The next generation of bacteriophage therapy; Current Opinion in Microbiology 14:524-531).*
Weiss et al. (In vivo replication of T4 and T7 bacteriophages in germ-free mice colonized with *Escherichia coli*; Virology 393: 16-23).*
Chibani-Chennoufi et al. 2004 (In vitro and in vivo bacteriolytic activities of *Escherichia coli* phages: implications for phage therapy; Antimicrobial agents and Chemotherapy 48(7): 2558-2569).*
Johnson et al. 2008 (*Escherichia coli* colonization patterns among human household member and pets, with attention to acute urinary tract infection; The Journal of Infectious Diseases 197:218-224).*
Seow et al. 2009 (Biological Gene Delivery Vehicles: Beyond Viral Vectors; Molecular Therapy 17(5):767-777).*
Sidhu et al. 2001 (Engineering M13 for phage display; Biomolecular Engineering, 18:57-63; see Pertinent Art).*
Citorik et al., Bacteriophage-based synthetic biology for the study of infectious diseases. Curr Opin Microbiol. Jun. 2014;19:59-69. doi: 10.1016/j.mib.2014.05.022. Epub Jul. 3, 2014.
Lu et al., Advancing bacteriophage-based microbial diagnostics with synthetic biology. Trends Biotechnol. Jun. 2013;31(6):325-7. doi: 10.1016/j.tibtech.2013.03.009. Epub Apr. 19, 2013.
Lu et al., Engineering synthetic bacteriophage to combat antibiotic-resistant bacteria. Bioengineering Conference. 2009 IEEE 35th Annual Northeast.
Ortiz et al., Engineered cell-cell communication via DNA messaging. J Biol Eng. Sep. 7, 2012;6(1):16. doi: 10.1186/1754-1611-6-16.
Westwater et al., Use of genetically engineered phage to deliver antimicrobial agents to bacteria: an alternative therapy for treatment of bacterial infections. Antimicrob Agents Chemother. Apr. 2003;47(4):1301-7.
Extended European Search Report for Application No. 14819499.6 dated Jan. 26, 2017.

(Continued)

*Primary Examiner* — Mary Maille Lyons
(74) *Attorney, Agent, or Firm* — Wolf, Greenfield & Sacks, P.C.

(57) ABSTRACT

Various aspects and embodiments of the present disclosure are directed to methods and compositions for functionalizing endogenous bacteria in vivo. The methods include delivering to endogenous bacterial cells a recombinant bacteriophage or phagemid that is engineered to contain at least one genetic circuit.

8 Claims, 17 Drawing Sheets

(56) References Cited

OTHER PUBLICATIONS

Berg, The Indigenous gastrointestinal microflora. Trends in Micriobio. Nov. 1, 1996;4(11):430-5.

Froyen et al., Cloning, Bacterial Expressions and Biological Characterization of Recombinant Human Granulocyte Chemotactic Protein-2 and Differential Expression of Granulocyte Chemotactic Protein-2 and Epithelial Cell-Derived Neutrophil Activating Peptide-78 mRNAs. Europ. J. of Biochem. Feb. 1, 1997:243(3);762-9.

Hoogenboom et al., Multi-subunit proteins on the surface of the filamentous phage: methodologies for displaying antibody (Fab) heavy and light chains. Nucleic Acids Research. Jan. 1, 1991:19(15);4133-7.

\* cited by examiner

FUNCTIONALIZATION OF ENDOGENOUS BACTERIA

RELATED APPLICATION

This application claims the benefit under 35 U.S.C. § 119(e) of U.S. provisional application No. 61/841,904, filed Jul. 1, 2013, which is incorporated by reference herein in its entirety.

FEDERALLY SPONSORED RESEARCH

This invention was made with government support under Grant Nos. DP2 OD008435 and T32 GM008334 awarded by the National Institutes of Health. The government has certain rights in the invention.

BACKGROUND OF THE INVENTION

A human microbiome is considered to be the aggregate of microorganisms that reside on the surface and in deep layers of the skin, in the saliva and oral mucosa, in the conjunctive, an in the gastrointestinal tracts. A human microbiome is thought to be composed of at least ten times as many bacterial cells as human cells, and these bacterial communities are known to have major impacts on the systems in which they reside. For example, recent studies have implicated the human microbiome in many human diseases.

SUMMARY OF THE INVENTION

The present disclosure is based, at least in part, on the surprising discovery that endogenous bacterial cells of a microbiome (e.g., human microbiome) can be "functionalized" in vivo with new genetically encoded capabilities to perform a range of useful functions. Thus, the present disclosure provides, inter alia, methods and compositions for selectively manipulating bacterial cells that are stably maintained in a microbiome (e.g., endogenous bacterial cells), for example, to deliver therapeutic molecules and/or to serve as "biosensors." The present disclosure is also based on the discovery that recombinant bacteriophages (e.g., non-lytic, or lysogenic bacteriophages) can be engineered to selectively deliver, to endogenous bacterial cells in vivo, particular genetic circuits, which when expressed, functionalize the bacterial cells.

Thus, various aspects and embodiments of the present disclosure provide methods of functionalizing endogenous bacteria in vivo, the methods comprising delivering to endogenous bacterial cells a recombinant bacteriophage that is engineered to contain at least one genetic circuit. Other aspects and embodiments of the present disclosure contemplate the delivery of recombinant phagemids to endogenous bacterial cells.

In some embodiments, the at least one genetic circuit does not express an antimicrobial protein or peptide.

Various other aspects and embodiments of the present disclosure provide recombinant bacteriophages that are engineered for in vivo delivery to endogenous bacterial cells and to contain at least one genetic circuit, wherein the at least one genetic circuit does not express an antimicrobial protein or peptide. Other aspects and embodiments of the present disclosure provide recombinant phagemids that are engineered for in vivo delivery to endogenous bacterial cells and to contain at least one genetic circuit, wherein the at least one genetic circuit does not express an antimicrobial protein.

In some embodiments, the endogenous bacterial cells are nonpathogenic bacterial cells.

In some embodiments, the endogenous bacterial cells are stably maintained in a microbiome.

In some embodiments, the recombinant bacteriophage is a non-lytic recombinant bacteriophage. In some embodiments, non-lytic bacteriophages, or phagemids, are from a family selected from Myoviridae, Siphoviridae, Podoviridae, Tectiviridae, Corticoviridae, Lipothrixviridae, Plasmaviridae, Rudiviridae, Fuselloviridae, Inoviridae, Microviridae, Leviviridae and Cystoviridae. In some embodiments, wherein a non-lytic recombinant Inoviridae bacteriophage is an M13 or M13-like bacteriophage. In some embodiments, a recombinant phagemid is an M13-derived phagemid.

In some embodiments, the genetic circuit contains a nucleic acid with a promoter operably linked to a nucleotide sequence encoding a gene product.

In some embodiments, the nucleic acid is a recombinant nucleic acid. In some embodiments, the nucleic acid is a synthetic nucleic acid.

In some embodiments, the promoter is a constitutively active promoter. In some embodiments, the promoter is an inducible promoter.

In some embodiments, the genetic circuit is a recombinase-based genetic circuit.

In some embodiments, the genetic circuit is engineered to express a therapeutic molecule. In some embodiments, the genetic circuit comprises a nucleic acid with a promoter operably linked to a nucleotide sequence that encodes the therapeutic molecule. In some embodiments, the therapeutic molecule is an antibody, antibody-based drug, Fc fusion protein, anticoagulant, blood factor, bone morphogenetic protein, engineered protein scaffold, enzyme, growth factor, hormone, interferon, interleukin or thrombolytic.

In some embodiments, the genetic circuit is engineered to detect a condition. In some embodiments, the condition is a cancer, an immune disorder or an infection.

In some embodiments, the genetic circuit comprises a nucleic acid with an inducible promoter operably linked to a nucleotide sequence that encodes a reporter molecule. In some embodiments, the reporter molecule is a fluorescent protein.

In some embodiments, the genetic circuit comprises a nucleic acid with a promoter operably linked to a nucleotide sequence that encodes toluene dioxygenase or styrene monoxygenase.

Also provided herein are compositions that comprise any one or more of the recombinant bacteriophages and/or phagemids of the present disclosure.

As used herein, "a" and "an" should be understood to mean "at least one."

BRIEF DESCRIPTION OF THE DRAWINGS

The accompanying drawings are not intended to be drawn to scale. In the drawings, each identical or nearly identical component illustrated in various figures is represented by a like numeral. For purposes of clarity, not every component may be labeled in every drawing.

FIG. 5 also shows a graph of indigo concentration over time produced by bacteria transformed with the constitutive PLtet0 promoter network expressing styrene monooxygenase ("test network") or infected with recombinant M13 bacteriophage harboring the constitutive PLtet0 promoter network expressing styrene monooxygenase ("bacteriophage network") (bottom). Styrene monooxygenase (and, thus, indigo) is produced in the presence of the Pbad inducer for both the test network and the bacteriophage network.

FIG. 6 also shows a graph of the fold change of the concentration of indigo produced over time by bacteria transformed with the constitutive PLtet0 test network versus bacteria infected with the constitutive PLtet0 bacteriophage network (bottom).

DETAILED DESCRIPTION OF THE INVENTION

Figure 1:
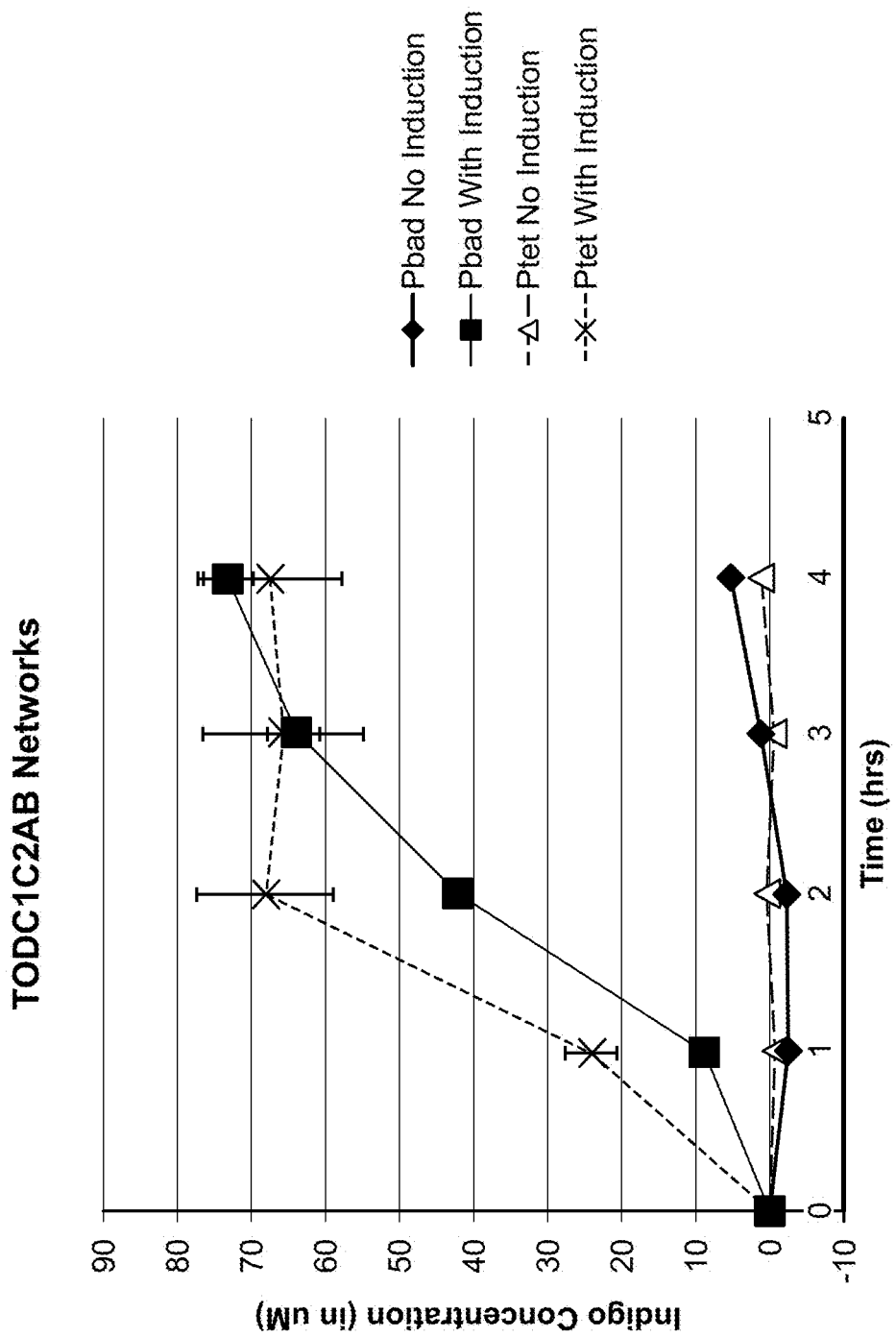
FIG. 1 shows a graph of indigo concentration over time for the constitutive PLtet0 and the inducible Pbad promoter networks used to express toluene dioxygenase. Toluene dioxygenase (and, thus, indigo) is produced in the presence of the Pbad inducer and in the presence of the Ptet inducer.

Provided herein are efficient and effective strategies for selectively manipulating endogenous bacterial cells of a microbiome to express genetic circuits, for example, to deliver therapeutic molecules to the host organism or to detect changes in the host organism's biological environment. Surprisingly, the present disclosure shows that these endogenous bacterial cells, which are stably maintained in a host organism, can be manipulated in vivo through the use of viruses (e.g., bacteriophages), or virus particles (e.g., phagemids), to serve as, inter alia, long-term drug delivery devices and biosensors. One traditional way of manipulating a microbiome is to administer antibiotics; however, antibiotics are broad spectrum in nature and target/kill both pathogenic and non-pathogenic "healthy" bacteria. Another traditional way of manipulating a microbiome is to deliver exogenous bacteria in the form of, for example, probiotic pills or yogurt; however, exogenous bacteria are typically only transiently present in the microbiome to which they are delivered because most existing ecological niches are already occupied by endogenous bacteria. Unlike the foregoing traditional strategies, which are indiscriminate and transient in nature, the present disclosure provides, in some instances, selective and stable delivery of new genetic programs to endogenous bacterial cells already established in a microbiome.

A "microbiome," as used herein, refers to the totality of microbes in a particular environment (e.g., in/on an organism, in a marine environment (e.g., ocean), and/or in a terrestrial environment (e.g., soil)). In some embodiments, a microbiome may refer to the totality of microbes that reside, or are stably maintained, for example, on the surface and in deep layers of the skin, in the saliva and oral mucosa, in the conjunctiva, and in the gastrointestinal tracts of an organism. A "host" organism or subject (e.g., animal such as a mammal, e.g., human) refers to the organism in/on which endogenous bacteria reside. Examples of host organisms or subjects in accordance with the present disclosure include, without limitation, animals such as humans, domesticated animals (e.g., cats, dogs, rodents, rabbits, birds), and farm animals (e.g., cows, pigs, goats, chickens, horse, sheep). It is to be understood that the microbes (e.g., endogenous bacteria) of a microbiome are typically non-pathogenic, or "healthy," microbes (e.g., they exist symbiotically, or in a mutually beneficial relationship, in an organism and do not cause disease unless the microbes grow abnormally). The bacterial cells (e.g., non-pathogenic bacterial cells) that make up a microbiome are referred to herein as "endogenous" bacterial cells. The endogenous bacteria that exist in/on an organism are distinguished from exogenous bacteria, which can be introduced to an organism and, in some instances, may be pathogenic (e.g., may cause disease).

The present disclosure is directed, in some embodiments, to methods of functionalizing endogenous bacteria in vivo to express genetic circuits that can be used, for example, to deliver therapeutic molecules and/or to act as biosensors of various biological conditions and/or disease states. To achieve this functionalization, the present disclosure contemplates, in some embodiments, engineering non-lytic, or lysogenic, recombinant bacteriophages and/or phagemids as vehicles to deliver to endogenous bacterial cells a variety of new genetic programs.

Bacteriophages

A bacteriophage (also referred to as a phage), is a virus that infects and replicates in bacteria. Bacteriophages are composed of proteins that encapsulate a DNA or RNA genome and may have relatively simple or elaborate structures. Their genomes may encode as few as four genes, and as many as hundreds of genes. Bacteriophages replicate within bacteria following the injection of their genome into the cytoplasm and do so using either a lytic cycle, which results in bacterial cell lysis, or a lysogenic (non-lytic) cycle, which leaves the bacterial cell intact. Bacteriophages of the present disclosure are, in some embodiments, non-lytic (also referred to as lysogenic or temperate). Thus, after phage delivery of a genetic circuit to an endogenous bacterial cell, the bacterial cell may remain viable and able to stably maintain expression of the genetic circuit.

Examples of non-lytic bacteriophage for use in accordance with the present disclosure include, without limitation, Myoviridae (P1-like viruses; P2-like viruses; Mu-like viruses; SPO1-like viruses; phiH-like viruses); Siphoviridae (λ-like viruses, γ-like viruses, T1-like viruses; T5-like viruses; c2-like viruses; L5-like viruses; .psi.M1-like viruses; phiC31-like viruses; N15-like viruses); Podoviridae (phi29-like viruses; P22-like viruses; N4-like viruses); Tectiviridae (Tectivirus); Corticoviridae (Corticovirus); Lipothrixviridae (Alphalipothrixvirus, Betalipothrixvirus, Gammalipothrixvirus, Deltalipothrixvirus); Plasmaviridae (Plasmavirus); Rudiviridae (Rudivirus); Fuselloviridae (Fusellovirus); Inoviridae (Inovirus, Plectrovirus, M13-like viruses, fd-like viruses); Microviridae (Microvirus, Spiromicrovirus, Bdellomicrovirus, Chlamydiamicrovirus); Leviviridae (Levivirus, Allolevivirus) and Cystoviridae (Cystovirus). Such phages may be naturally occurring or engineered phages. In some embodiments, a bacteriophage is a coliphage (e.g., infects *Escherichia coli*).

In some embodiments, a bacteriophage of the present disclosure is an M13 bacteriophage. M13 is a filamentous bacteriophage of the family Inoviridae and is composed of circular single-stranded DNA. M13 phages are about 900 nm long and 6-7 nm in diameter with 5 proteins. The minor coat protein, P3, attaches to the receptor at the tip of the F pilus of an *Escherichia coli* host cell. Thus, in some embodiments, methods of the present disclosure comprise delivering to endogenous bacterial cells a recombinant M13 bacteriophage that is engineered to contain at least one genetic circuit.

In some embodiments, the bacteriophage of the present disclosure is isolated from (e.g., collected from, obtained from) stool or sewage.

Phagemids

In some embodiments of the present disclosure, phagemids are engineered to contain at least one genetic circuit. As used herein, "phagemid" refers to a bacteriophage-derived vector containing the replication origin of a plasmid and the packaging site of a bacteriophage. Examples of phagemids that may be used in accordance with the present disclosure include, without limitation, M13-derived phagemids containing the f1 origin for filamentous bacteriophage packaging such as, for example, pBluescript II SK (+/−) and KS (+/−) phagemids, pBC SK and KS phagemids, pADL and P1-based phagemids (see, e.g., Westwater C A et al., *Microbiology* 148, 943-50 (2002); Kittleson J T et al., *ACS Synthetic Biology* 1, 583-89 (2012); Mead D A et al., *Biotechnology* 10, 85-102 (1988)). Other phagemids may be used in accordance with the present disclosure and, for example, can be made to work with packaging systems from natural, engineered or evolved bacteriophage.

Endogenous Bacterial Cells

A microbiome may comprise of a variety of endogenous bacterial species, any of which may be targeted in accordance with the present disclosure. In some embodiments, the genus and/or species of target endogenous bacterial cells may depend on the type of bacteriophage and/or phagemid being used. For example, some bacteriophages exhibit tropism for, or preferentially target, specific host species of bacteria. Other bacteriophages do not exhibit such tropism and may be used to target a number of different genus and/or species of endogenous bacterial cells. In some embodiments, the bacteria are considered to be lysogenic bacteria. As used herein, "lysogenic bacteria" are endogenous bacteria that are infected by a non-lytic (also referred to as lysogenic or temperate) bacteriophage. Lysogenic bacteria are typically not lysed by bacteriophage infection. It should be appreciated that, in some instances, infection of an endogenous bacterial cell by a non-lytic or lysogenic bacteriophage may result in cell lysis of, for example, a small proportion (e.g., less than 20%, less than 10%, less than 5%, less than 2%, or less than 1%) of the infected bacterial cells.

Bacteria are small (typical linear dimensions of around 1 micron), non-compartmentalized, with circular DNA and ribosomes of 70S. As used herein, the term "bacteria" encompasses all variants of endogenous bacteria. "Endogenous" bacteria naturally reside in a closed system. Bacterial cells of the present disclosure include bacterial subdivisions of Eubacteria and Archaebacteria. Eubacteria can be further subdivided into gram-positive and gram-negative Eubacteria, which depend upon a difference in cell wall structure. Also included herein are those classified based on gross morphology alone (e.g., cocci, bacilli). In some embodiments, the bacterial cells are Gram-negative cells, and in some embodiments, the bacterial cells are Gram-positive cells. Examples of bacterial cells of the present disclosure include, without limitation, cells from *Yersinia* spp., *Escherichia* spp., *Klebsiella* spp., *Bordetella* spp., *Neisseria* spp., *Aeromonas* spp., *Franciesella* spp., *Corynebacterium* spp., *Citrobacter* spp., *Chlamydia* spp., *Hemophilus* spp., *Brucella* spp., *Mycobacterium* spp., *Legionella* spp., *Rhodococcus* spp., *Pseudomonas* spp., *Helicobacter* spp., *Salmonella* spp., *Vibrio* spp., *Bacillus* spp., *Erysipelothrix* spp., *Salmonella* spp., *Streptomyces* spp., *Bacteroides* spp., *Prevotella* spp., *Clostridium* spp., *Bifidobacterium* spp., or *Lactobacillus* spp. In some embodiments, the bacterial cells are from *Bacteroides thetaiotaomicron, Bacteroides fragilis, Bacteroides distasonis, Bacteroides vulgatus, Clostridium leptum, Clostridium coccoides, Staphylococcus aureus, Bacillus subtilis, Clostridium butyricum, Brevibacterium lactofermentum, Streptococcus agalactiae, Lactococcus lactis, Leuconostoc lactis, Actinobacillus actinobycetemcomitans*, cyanobacteria, *Escherichia coli, Helicobacter pylori, Selnomonas ruminatium, Shigella sonnei, Zymomonas mobilis, Mycoplasma mycoides, Treponema denticola, Bacillus thuringiensis, Staphlococcus lugdunensis, Leuconostoc oenos, Corynebacterium xerosis, Lactobacillus plantarum, Lactobacillus rhamnosus, Lactobacillus casei,*

Lactobacillus acidophilus, Streptococcus Enterococcus faecalis, Bacillus coagulans, Bacillus ceretus, Bacillus popillae, Synechocystis strain PCC6803, Bacillus liquefaciens, Pyrococcus abyssiSelenomonas nominantium, Lactobacillus hilgardii, Streptococcus ferus, Lactobacillus pentosus, Bacteroides fragilis, Staphylococcus epidermidis, Zymomonas mobilis, Streptomyces phaechromogenes, or Streptomyces ghanaenis. Thus, bacteriophages and/or phagemids of the present disclosure may target (e.g., specifically target) a bacterial cell from any one or more of the foregoing genus and/or species of bacteria.

In some embodiments, bacterial cells of the present disclosure are anaerobic bacterial cells (e.g., cells that do not require oxygen for growth). Anaerobic bacterial cells include facultative anaerobic cells such as, for example, Escherichia coli, Shewanella oneidensis and Listeria. Anaerobic bacterial cells also include obligate anaerobic cells such as, for example, Bacteroides and Clostridium species. In humans, for example, anaerobic bacteria are most commonly found in the gastrointestinal tract. Thus, bacteriophages and/or phagemids of the present disclosure may target (e.g., specifically target) anaerobic bacterial cells.

Genetic Circuits

The non-lytic recombinant bacteriophages and/or phagemid of the present disclosure are engineered to deliver to endogenous bacterial cells one or more of a variety of genetic circuits, which may depend on the particular intended application (e.g., delivery of a therapeutic molecule). A "genetic circuit," as used herein, refers to a nucleic acid containing at least one promoter operably linked to at least one nucleic acid sequence that encodes a gene product of interest (e.g., protein or RNA). In some embodiments, a genetic circuit contains a nucleic acid with a promoter operably linked to a single gene, and in other embodiments, the promoter is operably linked to a cluster of genes (e.g., an operon). In yet other embodiments, a genetic circuit may contain more than one promoter, each linked (e.g., operably linked) to the same gene, the same cluster of genes, or to a different gene or cluster of genes. Herein, a genetic circuit that is "engineered to express" a particular gene product (e.g., a therapeutic molecule) may be a genetic circuit that contains at least the genetic elements required for expression of the particular gene product. For example, a genetic circuit that is engineered to express a monoclonal antibody may contain at least one nucleic acid with at least one promoter operably linked to at least one nucleotide sequence encoding the primary amino acid sequence of the monoclonal antibody. Herein, a genetic circuit that is "engineered to detect" a particular condition (e.g., a disease state) may be a genetic circuit that contains at least the genetic elements required for regulated expression of a reporter molecule or other molecule that can be visualized or quantified. For example, a genetic circuit that is engineered to detect oxidative stress via pOxyS or pSoxS and to respond by expressing a styrene monoxygenase enzyme or an anti-inflammatory gene such as, for example, interleukin 10. Styrene monooxygenase converts indole, present in the gut, to indigo as a visual readout.

The genetic circuits of the present disclosure may be constitutive or regulated. A "constitutive" genetic circuit, as used herein, is active in all circumstances in the bacterial cell, whereas a "regulated" genetic circuit becomes active, or inactive, in response to specific stimuli. A genetic circuit is considered to be "active" when a promoter, described elsewhere herein, initiates transcription of an operably linked nucleotide sequence (e.g., gene sequence). A genetic circuit is considered to be "inactive" when transcription of an operably linked nucleotide sequence is terminated. A constitutive genetic circuit may contain a nucleic acid with a constitutive promoter operably linked to nucleotide sequence encoding a gene product of interest. By contrast, a regulated genetic circuit may contain a nucleic acid with an inducible promoter that activates gene expression in response to specific stimuli or that inactivates gene expression in response to specific stimuli.

Genetic Elements

Genetic circuits of the present disclosure contain at least one genetic element that can regulate gene/protein expression. A "genetic element," as used herein, refers to a nucleotide sequence that has a role in gene expression. For example, nucleic acids (e.g., recombinant nucleic acids) encoding proteins, promoters, enhancers and terminators are considered to be genetic elements.

Nucleic Acids

As used herein, the term "nucleic acid" refers to at least two nucleotides covalently linked together, and in some instances, may contain phosphodiester bonds (e.g., a phosphodiester "backbone"). In some embodiments, a nucleic acid of the present disclosure may be considered to be a nucleic acid analog, which may contain other backbones comprising, for example, phosphoramide, phosphorothioate, phosphorodithioate, O-methylphosphoroamidite linkages, and/or peptide nucleic acids. Nucleic acids of the present disclosure may be naturally occurring, recombinant or synthetic. "Recombinant nucleic acids" may refer to molecules that are constructed by joining nucleic acid molecules and, in some embodiments, can replicate in a living cell. "Synthetic nucleic acids" may refer to molecules that are chemically or by other means synthesized or amplified, including those that are chemically or otherwise modified but can base pair with naturally occurring nucleic acid molecules. Recombinant and synthetic nucleic acids also include those molecules that result from the replication of either of the foregoing.

The nucleic acids may be single-stranded (ss) or double-stranded (ds), as specified, or may contain portions of both single-stranded and double-stranded sequence. The nucleic acid may be DNA, both genomic and cDNA, RNA or a hybrid, where the nucleic acid contains any combination of deoxyribo- and ribonucleotides, and any combination of bases, including uracil, adenine, thymine, cytosine, guanine, inosine, xathanine hypoxathanine, isocytosine, and isoguanine.

Promoters

The genetic circuits of the present disclosure may contain nucleic acids with promoter sequences, or promoters, operably linked to a nucleotide sequence encoding a gene product of interest. As used herein, a "promoter" refers to a control region of a nucleic acid sequence at which initiation and rate of transcription of the remainder of a nucleic acid sequence are controlled. A promoter may also contain subregions at which regulatory proteins and molecules may bind, such as RNA polymerase and other transcription factors. Promoters may be constitutive, inducible, activatable, repressible, tissue-specific or any combination thereof.

A promoter drives expression or drives transcription of the nucleic acid sequence that it regulates. Herein, a promoter is considered to be "operably linked" when it is in a correct functional location and orientation in relation to a nucleic acid sequence it regulates to control ("drive") transcriptional initiation and/or expression of that sequence.

A promoter may be classified as strong or weak according to its affinity for RNA polymerase (and/or sigma factor); this is related to how closely the promoter sequence resembles the ideal consensus sequence for the polymerase. The strength of a promoter may depend on whether initiation of transcription occurs at that promoter with high or low frequency. Different promoters with different strengths may be used to construct genetic circuits with different levels of gene/protein expression (e.g., the level of expression initiated from a weak promoter is lower than the level of expression initiated from a strong promoter).

A promoter may be one naturally associated with a gene or sequence, as may be obtained by isolating the 5' non-coding sequences located upstream of the coding segment and/or exon of a given gene or sequence. Such a promoter can be referred to as "endogenous." Similarly, an enhancer may be one naturally associated with a nucleic acid sequence, located either downstream or upstream of that sequence.

In some embodiments, a coding nucleic acid segment may be positioned under the control of a recombinant or heterologous promoter, which refers to a promoter that is not normally associated with the encoded nucleic acid sequence in its natural environment. A recombinant or heterologous enhancer refers to an enhancer not normally associated with a nucleic acid sequence in its natural environment. Such promoters or enhancers may include promoters or enhancers of other genes; promoters or enhancers isolated from any other prokaryotic cell; and synthetic promoters or enhancers that are not "naturally occurring" such as, for example, those that contain different elements of different transcriptional regulatory regions and/or mutations that alter expression through methods of genetic engineering that are known in the art. In addition to producing nucleic acid sequences of promoters and enhancers synthetically, sequences may be produced using recombinant cloning and/or nucleic acid amplification technology, including polymerase chain reaction (PCR) (see U.S. Pat. No. 4,683,202 and U.S. Pat. No. 5,928,906).

Inducible Promoters

As used herein, an "inducible promoter" is one that is characterized by initiating or enhancing transcriptional activity when in the presence of, influenced by or contacted by an inducer or inducing agent. An "inducer" or "inducing agent" may be endogenous or a normally exogenous condition, compound or protein that contacts a genetic circuit in such a way as to be active in inducing transcriptional activity from the inducible promoter.

Inducible promoters for use in accordance with the present disclosure function in a bacterial cell. Examples of inducible promoters for use herein include, without limitation, bacteriophage promoters (e.g. Pls1con, T3, T7, SP6) and bacterial promoters (e.g. Pbad, PmgrB, PLlacO, Ptrc2, PLtetO, Plac/ara, Ptac, Pm). Examples of bacterial promoters for use in accordance with the present disclosure include, without limitation, positively regulated E. coli promoters such as positively regulated $\sigma^{70}$ promoters (e.g., inducible pBad/araC promoter, Lux cassette right promoter, modified lamdba Prm promote, plac Or2-62 (positive), pBad/AraC with extra REN sites, pBad, P(Las) TetO, P(Las) CIO, P(Rh1), Pu, FecA, pRE, cadC, hns, pLas, pLux), $\sigma^S$ promoters (e.g., Pdps), $\sigma^{32}$ promoters (e.g., heat shock) and $\sigma^{54}$ promoters (e.g., glnAp2); negatively regulated E. coli promoters such as negatively regulated $\sigma^{70}$ promoters (e.g., Promoter (PRM+), modified lamdba Prm promoter, TetR-TetR-4C P(Las) TetO, P(Las) CIO, P(Lac) IQ, RecA_Dlex-O_DLacO1, dapAp, FecA, Pspac-hy, pcI, plux-cI, plux-lac, CinR, CinL, glucose controlled, modified Pr, modified Prm+, FecA, Pcya, rec A (SOS), Rec A (SOS), EmrR_regulated, BetI_regulated, pLac_lux, pTet_Lac, pLac/Mnt, pTet/Mnt, LsrA/cI, pLux/cI, LacI, LacIQ, pLacIQ1, pLas/cI, pLas/Lux, pLux/Las, pRecA with LexA binding site, reverse BBa_R0011, pLacI/ara-1, pLacIq, rrnB P1, cadC, hns, PfhuA, pBad/araC, nhaA, OmpF, RcnR), $\sigma^S$ promoters (e.g., Lutz-Bujard LacO with alternative sigma factor $\sigma^{38}$), $\sigma^{32}$ promoters (e.g., Lutz-Bujard LacO with alternative sigma factor $\sigma^{32}$), and $\sigma^{54}$ promoters (e.g., glnAp2); negatively regulated B. subtilis promoters such as repressible B. subtilis $\sigma^A$ promoters (e.g., Gram-positive IPTG-inducible, Xy1, hyper-spank) and $\sigma^B$ promoters. Other inducible bacterial promoters may be used in accordance with the present disclosure.

The administration or removal of an inducer results in a switch between activation and inactivation of the transcription of the operably linked nucleic acid sequence (e.g., nucleic acid encoding a gene product of interest). Thus, as used herein, the active state of a promoter operably linked to a nucleic acid sequence refers to the state when the promoter is actively driving transcription of the nucleic acid sequence (i.e., the linked nucleic acid sequence is expressed). Conversely, the inactive state of a promoter operably linked to a nucleic acid sequence refers to the state when the promoter is not actively driving transcription of the nucleic acid sequence (i.e., the linked nucleic acid sequence is not expressed).

An inducible promoter for use in accordance with the present disclosure may be induced by (or repressed by) one or more physiological condition(s), such as changes in pH, temperature, radiation, osmotic pressure, saline gradients, cell surface binding, and the concentration of one or more extrinsic or intrinsic inducing agent(s). The extrinsic inducer or inducing agent may comprise, without limitation, amino acids and amino acid analogs, saccharides and polysaccharides, nucleic acids, protein transcriptional activators and repressors, cytokines, toxins, petroleum-based compounds, metal containing compounds, salts, ions, enzyme substrate analogs, hormones or combinations thereof.

Inducible promoters for use in accordance with the present disclosure include any inducible promoter described herein or known to one of ordinary skill in the art. Examples of inducible promoters include, without limitation, chemically/biochemically-regulated and physically-regulated promoters such as alcohol-regulated promoters, tetracycline-regulated promoters (e.g., anhydrotetracycline (aTc)-responsive promoters and other tetracycline-responsive promoter systems, which include a tetracycline repressor protein (tetR), a tetracycline operator sequence (tetO) and a tetracycline transactivator fusion protein (tTA)), steroid-regulated promoters (e.g., promoters based on the rat glucocorticoid receptor, human estrogen receptor, moth ecdysone receptors, and promoters from the steroid/retinoid/thyroid receptor superfamily), metal-regulated promoters (e.g., promoters derived from metallothionein (proteins that bind and sequester metal ions) genes from yeast, mouse and human), pathogenesis-regulated promoters (e.g., induced by salicylic acid, ethylene or benzothiadiazole (BTH)), temperature/heat-inducible promoters (e.g., heat shock promoters), and light-regulated promoters (e.g., light responsive promoters from plant cells).

In some embodiments, the inducer used in accordance with the present disclosure is an N-acyl homoserine lactone (AHL), which is a class of signaling molecules involved in bacterial quorum sensing. Quorum sensing is a method of communication between bacteria that enables the coordination of group based behavior based on population density. AHL can diffuse across cell membranes and is stable in growth media over a range of pH values. AHL can bind to transcriptional activators such as LuxR and stimulate transcription from cognate promoters. In some embodiments, the inducer used in accordance with the present disclosure is anhydrotetracycline (aTc), which is a derivative of tetracycline that exhibits no antibiotic activity and is designed for use with tetracycline-controlled gene expression systems, for example, in bacteria.

Other inducible promoter systems are known in the art and may be used in accordance with the present disclosure.

Enhancers

In some embodiments of the present disclosure, a promoter may or may not be used in conjunction with an "enhancer," which refers to a cis-acting regulatory sequence involved in the transcriptional activation of a nucleic acid sequence downstream of the promoter. The enhancer may be located at any functional location before or after the promoter.

Terminators

In some embodiments, a genetic circuit may contain a terminator sequence, or terminator. A "terminator," as used herein, is a nucleic acid sequence that causes transcription to stop. A terminator may be unidirectional or bidirectional. It is comprised of a DNA sequence involved in specific termination of an RNA transcript by an RNA polymerase. A terminator sequence prevents transcriptional activation of downstream nucleic acid sequences by upstream promoters. Thus, in certain embodiments, a terminator that ends the production of an RNA transcript is contemplated. A terminator may be necessary in vivo to achieve desirable gene/protein expression levels.

The most commonly used type of terminator is a forward terminator. When placed downstream of a nucleic acid sequence that is usually transcribed, a forward transcriptional terminator will cause transcription to abort. In some embodiments, bidirectional transcriptional terminators are provided, which usually cause transcription to terminate on both the forward and reverse strand. In some embodiments, reverse transcriptional terminators are provided, which usually terminate transcription on the reverse strand only.

In prokaryotic systems, terminators usually fall into two categories (1) rho-independent terminators and (2) rho-dependent terminators. Rho-independent terminators are generally composed of palindromic sequence that forms a stem loop rich in G-C base pairs followed by several T bases. Without wishing to be bound by theory, the conventional model of transcriptional termination is that the stem loop causes RNA polymerase to pause, and transcription of the poly-A tail causes the RNA:DNA duplex to unwind and dissociate from RNA polymerase.

Terminators for use in accordance with the present disclosure include any terminator of transcription described herein or known to one of ordinary skill in the art. Examples of terminators include, without limitation, the termination sequences of genes such as, for example, the bovine growth hormone terminator, and viral termination sequences such as, for example, the T0 terminator, the TE terminator, Lambda T1 and the T1T2 terminator found in bacterial systems. In some embodiments, the termination signal may be a sequence that cannot be transcribed or translated, such as those resulting from a sequence truncation.

Other genetic elements are known in the art and may be used in accordance with the present disclosure.

Recombinase-Based Genetic Circuits

In some embodiments of the present disclosure, the endogenous bacterial cells are functionalized with recombinase-based genetic circuits. A "recombinase," as used herein, is a site-specific enzyme that recognizes short DNA sequence(s), which sequence(s) are typically between about 30 base pairs (bp) and 40 bp, and that mediates the recombination between these recombinase recognition sequences, which results in the excision, integration, inversion, or exchange of DNA fragments between the recombinase recognition sequences. For example, in some embodiments, recombinant bacteriophages and/or phagemids of the present disclosure may be engineered to deliver at least two genetic circuits, one containing a nucleic acid with an inducible promoter operably linked to a nucleic acid encoding a recombinase, and the other containing a nucleic acid with a promoter operably linked to a nucleotide sequence encoding a gene product of interest and optionally containing a terminator, wherein at least one of the promoter and terminator is flanked by a forward and a reverse recognition site of the recombinase. In such embodiments, expression of the gene product of interest of one circuit is regulated by recombinase activity, or inactivity, of the other circuit.

Recombinases can be classified into two distinct families: serine recombinases (e.g., resolvases and invertases) and tyrosine recombinases (e.g., integrases), based on distinct biochemical properties. Serine recombinases and tyrosine recombinases are further divided into bidirectional recombinases and unidirectional recombinases. Examples of bidirectional serine recombinases for use herein include, without limitation, β-six, CinH, ParA and γδ; and examples of unidirectional serine recombinases include, without limitation, Bxb1, φC31, TP901, TG1, φBT1, R4, φRV1, φFC1, MR11, A118, U153 and gp29. Examples of bidirectional tyrosine recombinases for use herein include, without limitation, Cre, FLP, and R; and unidirectional tyrosine recombinases include, without limitation, Lambda, HK101, HK022 and pSAM2. The serine and tyrosine recombinase names stem from the conserved nucleophilic amino acid residue that the recombinase uses to attack the DNA and which becomes covalently linked to the DNA during strand exchange.

The outcome of recombination depends, in part, on the location and orientation of two short repeated DNA sequences that are to be recombined, typically less than 30 bp long. Recombinases bind to these repeated sequences, which are specific to each recombinase, and are herein referred to as "recombinase recognition sequences" or "recombinase recognition sites." Thus, as used herein, a recombinase is "specific for" a recombinase recognition site when the recombinase can mediate inversion or excision between the repeat nucleotide sequences. As used herein, a recombinase may also be said to recognize its "cognate recombinase recognition sites," which flank an intervening genetic element (e.g., promoter, terminator, or output nucleic acid sequence). A genetic element is said to be "flanked" by recombinase recognition sites when the element is located between and immediately adjacent to two repeated nucleotide sequences.

Recombinases can also be classified as irreversible or reversible. As used herein, an "irreversible recombinase" (also referred to as a "unidirectional recombinase") refers to a recombinase that can catalyze recombination between two complementary recombination sites, but cannot catalyze recombination between the hybrid sites that are formed by this recombination without the assistance of an additional factor. Thus, an "irreversible recognition site" refers to a recombinase recognition site that can serve as the first of two nucleotide recombination sequences for an irreversible recombinase and that is modified to a hybrid recognition site following recombination at that site. A "complementary irreversible recognition site" refers to a recombinase recognition site that can serve as the second of two nucleotide recognition sequences for an irreversible recombinase and that is modified to a hybrid recombination site following homologous recombination at that site.

Irreversible recombinases, and nucleic acids that encode the irreversible recombinases, are described in the art and can be obtained using routine methods. Examples of irreversible recombinases include, without limitation, phiC31 (φC31) recombinase, coliphage P4 recombinase (Ow & Ausubel, *J. Bacteriol.* 155, 704-713 (1983)), coliphage lambda integrase (Lorbach et al., *J. Mol. Biol.,* 296, 1175-81 (2000)), *Listeria* A118 phage recombinase (Loessner et al., *Mol. Micro.* 35, 324-340 (2000)), and actinophage R4 Sre recombinase (Matsuura et al., *J. Bacteriol.* 178, 3374-3376 (1996)), HK101, HK022, pSAM2, Bxb1, TP901, TG1, φBT1, φRV1, φFC1, MR11, U153 and gp29.

Conversely, a "reversible recombinase" refers to a recombinase that can catalyze recombination between two complementary recombinase recognition sites and, without the assistance of an additional factor, can catalyze recombination between the sites that are formed by the initial recombination event, thereby reversing it. The product-sites generated by recombination are themselves substrates for subsequent recombination. Examples of reversible recombinase systems include, without limitation, the Cre-lox and the Flp-frt systems, R, β-six, CinH, ParA and γδ.

In some embodiments, the recombinase is serine recombinase. Thus, in some embodiments, the recombinase is considered to be irreversible. In some embodiments, the recombinase is a tyrosine recombinase. Thus, in some embodiments, the recombinase is considered to be reversible.

The recombinases provided herein are not meant to be exclusive examples of recombinases that can be used in embodiments of the present disclosure. The complexity of the genetic circuits of the present disclosure can be expanded by mining databases for new orthogonal recombinases or designing synthetic recombinases with defined DNA specificities (Groth, A. C. & Calos, M. P. *J Mol Biol* 335, 667-678, (2004); Gordley, R. M., et al. *Proc Natl Acad Sci USA* 106, 5053-5058 (2009)). Other examples of recombinases that are useful in the genetic circuits described herein are known to those of skill in the art, and any new recombinase that is discovered or generated is expected to be able to be used in the different embodiments of the present disclosure.

Gene Products

The present disclosure contemplates recombinant bacteriophages and/or phagemids delivery of genetic circuits that encode one or more of a variety of gene products. As used herein, a "gene product" may refer to a protein product or RNA product that may be used, for example, as a therapeutic molecule or as a diagnostic or reporter molecule. Representative gene products for genetic circuits of the present disclosure include, without limitation, therapeutic proteins, reporter proteins, transcriptional repressors, transcriptional activators, enzymes, receptor proteins, ligand proteins, RNAs, riboswitches, RNA interference (e.g., shRNA, siRNA, microRNA) molecules and recombinases.

Therapeutic Molecules

Methods of the present disclosure, in some embodiments, may comprise delivering to endogenous bacterial cells a recombinant bacteriophage and/or phagemid that is engineered to contain at least one genetic circuit that expresses a therapeutic molecule. Therapeutic molecules include therapeutic proteins. Therapeutic molecules of the present disclosure may be used to, for example, replace a protein that is deficient or abnormal, augment an existing biological pathway, provide a novel function or activity, interfere with a molecule or organism, and/or deliver other compounds or proteins, such as a radionuclide, cytotoxic drug, or effector proteins. Therapeutic molecule contemplated by the present disclosure include, without limitation, antibodies, antibody-based drugs, Fc fusion proteins, anticoagulants, blood factors, bone morphogenetic proteins, engineered protein scaffolds, enzymes, growth factors, hormones, interferons, interleukins, and thrombolytics. Other examples include those that bind non-covalently to target (e.g., monoclonal antibodies), those that affect covalent bonds (e.g., enzymes), and those that exert activity without specific interactions (e.g., serum albumin).

Also contemplated herein are therapeutic molecules, e.g., recombinant therapeutic proteins, used to treat, for example, cancers, immune disorders, infections and/or other diseases. Engineered proteins, including bispecific mAbs and multi-specific fusion proteins, and proteins with optimized pharmacokinetics are also contemplated by the present disclosure.

In some embodiments, the therapeutic proteins is Etanercept, Bevacizumab, Rituximab, Adalimumab, Infliximab, Trastuzumab, Insulin glargine, Epoetin alfa, Pegfilgrastim, Ranibizumab, Darbepoetin alfa, Interferon beta-1a, Interferon beta-1a. Insulin aspart, Rinsulin, Octocog alfa, Insulin lispro, Cetuximab, Peginterferon alfa-2a, Interferon beta-1b, Eptacog alfa, Insulin aspart, OnabotulinumtoxinA, Epoetin beta, Rec antihemophilic factor, Filgrastin, Insulin detemir, Natalizumab, Insulin (humulin) or Palivizumab.

Examples of antibodies, antibody fragments, and/or Fc fusion proteins that may be encoded by the genetic circuits of the present disclosure include, without limitation, Abagovomab, Abciximab, Actoxumab, Adalimumab, Adecatumumab, Afelimomab, Afutuzumab, Alacizumab pegol, ALD, Alemtuzumab, Alirocumab, Altumomab pentetate, Amatuximab, Anatumomab mafenatox, Anifrolumab, Anrukinzumab, Apolizumab, Arcitumomab, Aselizumab, Atinumab, Atlizumab (or tocilizumab), Atorolimumab, Bapineuzumab, Basiliximab, Bavituximab, Bectumomab, Belimumab, Benralizumab, Bertilimumab, Besilesomab, Bevacizumab, Bezlotoxumab, Biciromab, Bimagrumab, Bivatuzumab mertansine, Blinatumomab, Blosozumab, Brentuximab vedotin, Briakinumab, Brodalumab, Canakinumab, Cantuzumab mertansine, Cantuzumab ravtansine, Caplacizumab, Capromab pendetide, Carlumab, Catumaxomab, Cedelizumab, Certolizumab pegol, Cetuximab, Citatuzumab bogatox, Cixutumumab, Clazakizumab, Clenoliximab, Clivatuzumab tetraxetan, Conatumumab, Concizumab, Crenezumab, Dacetuzumab, Daclizumab, Dalotuzumab, Daratumumab, Demcizumab, Denosumab, Detumomab, Dorlimomab aritox, Drozitumab, Duligotumab, Dupilumab, Dusigitumab, Ecromeximab, Eculizumab, Edobacomab, Edrecolomab, Efalizumab, Efungumab, Eldelumab, Elotuzumab, Elsilimomab, Enavatuzumab, Enlimomab pegol, Enokizumab, Enoticumab, Ensituximab, Epitumomab cituxetan, Epratuzumab, Erlizumab, Ertumaxomab, Etaracizumab, Etrolizumab, Evolocumab, Exbivirumab, Fanolesomab, Faralimomab, Farletuzumab, Fasinumab, FBTA, Felvizumab, Fezakinumab, Ficlatuzumab, Figitumumab, Flanvotumab, Fontolizumab, Foralumab, Foravirumab, Fresolimumab, Fulranumab, Futuximab, Galiximab, Ganitumab, Gantenerumab, Gavilimomab, Gemtuzumab ozogamicin, Gevokizumab, Girentuximab, Glembatumumab vedotin, Golimumab, Gomiliximab, Guselkumab, Ibalizumab, Ibritumomab tiuxetan, Icrucumab, Igovomab, Imciromab, Imgatuzumab, Inclacumab, Indatuximab ravtansine, Infliximab, Intetumumab, Inolimomab, Inotuzumab ozogamicin, Ipilimumab, Iratumumab, Itolizumab, Ixekizumab, Kelixmab, Labetuzumab, Lambrolizumab, Lampalizumab, Lebrikizumab, Lemalesomab, Lerdelimumab, Lexatumumab, Libivirumab, Ligelizumab, Lintuzumab, Lirilumab, Lodelcizumab, Lorvotuzumab mertansine, Lucatumumab, Lumiliximab, Mapatumumab, Margetuximab, Maslimomab, Mavrilimumab, Matuzumab, Mepolizumab, Metelimumab, Milatuzumab Minretumomab, Mitumomab, Mogamulizumab, Morolimumab, Motavizumab, Moxetumomab pasudotox, Muromonab-CD3, Nacolomab tafenatox, Namilumab, Naptumomab estafenatox, Narnatumab, Natalizumab, Nebacumab, Necitumumab, Nerelimomab, Nesvacumab, Nimotuzumab, Nivolumab, Nofetumomab merpentan, Ocaratuzumab, Ocrelizumab, Odulimomab, Ofatumumab, Olaratumab, Olokizumab, Omalizumab, Onartuzumab, Oportuzumab monatox, Oregovomab, Orticumab, Otelixizumab, Oxelumab, Ozanezumab, Ozoralizumab, Pagibaximab, Palivizumab, Panitumumab, Panobacumab, Parsatuzumab, Pascolizumab, Pateclizumab, Patritumab, Pemtumomab, Perakizumab, Pertuzumab, Pexelizumab, Pidilizumab, Pinatuzumab vedotin, Pintumomab, Placulumab, Polatuzumab vedotin, Ponezumab, Priliximab, Pritoxaximab, Pritumumab, PRO, Quilizumab, Racotumomab, Radretumab, Rafivirumab, Ramucirumab, Ranibizumab, Raxibacumab, Regavirumab, Reslizumab, Rilotumumab, Rituximab, Robatumumab, Roledumab, Romosozumab, Rontalizumab, Rovelizumab, Ruplizumab, Samalizumab, Sarilumab, Satumomab pendetide, Secukinumab, Seribantumab, Setoxaximab, Sevirumab, Sibrotuzumab, Sifalimumab, Siltuximab, Simtuzumab, Siplizumab, Sirukumab, Solanezumab, Solitomab, Sonepcizumab, Sontuzumab, Stamulumab, Sulesomab, Suvizumab, Tabalumab, Tacatuzumab tetraxetan, Tadocizumab, Talizumab, Tanezumab, Taplitumomab paptox, Tefibazumab, Telimomab aritox, Tenatumomab, Teneliximab, Teplizumab, Teprotumumab, TGN, Ticilimumab (or tremelimumab), Tildrakizumab, Tigatuzumab, TNX-, Tocilizumab (or atlizumab), Toralizumab, Tositumomab, Tovetumab, Tralokinumab, Trastuzumab, TRBS, Tregalizumab, Tremelimumab, Tucotuzumab celmoleukin, Tuvirumab, Ublituximab, Urelumab, Urtoxazumab, Ustekinumab, Vantictumab, Vapaliximab, Vatelizumab, Vedolizumab, Veltuzumab, Vepalimomab, Vesencumab, Visilizumab, Volociximab, Vorsetuzumab mafodotin, Votumumab, Zalutumumab, Zanolimumab, Zatuximab, Ziralimumab and Zolimomab aritox.

Other examples of Fc fusion proteins that may be encoded by the genetic circuits of the present disclosure include, without limitation, Etanercept, Alefacept, Abatacept, Rilonacept, Romiplostim, Belatacept and Aflibercept.

Examples of anticoagulants and/or blood factors that may be encoded by the genetic circuits of the present disclosure include, without limitation, Protein C, Protein S, and antithrombin, Factors I-VIII, prothrombinase, prothrombin, thrombin von Willebrand Factor (vWF), fibrinogen, fibrin and fibrinopeptides.

Examples of bone morphogenetic proteins (BMPs) that may be encoded by the genetic circuits of the present disclosure include, without limitation, BMP1-BMP7, BMP8a, BMP8b, BMP10, and BMP15.

Examples of enzymes that may be encoded by the genetic circuits of the present disclosure include, without limitation, any of the enzymes assigned an Enzyme Commission Number (EC) number (e.g., EC1-EC6) by the International Union of Biochemistry and Molecular Biology (IUBMB) (Webb, Edwin C. Enzyme nomenclature 1992: recommendations of the Nomenclature Committee of the International Union of Biochemistry and Molecular Biology on the nomenclature and classification of enzymes. San Diego Published for the International Union of Biochemistry and Molecular Biology by Academic Press. ISBN 0-12-227164-5 (1992), incorporated by reference herein). Other examples include: styrene monooxygenase (StyAB), toluene dioxygenase (TODC1C2AB), luciferase and lactase. In some embodiments, the enzyme is toluene dioxygenase. In some embodiments, the enzyme is styrene monoxygenase.

Examples of growth factors that may be encoded by the genetic circuits of the present disclosure include, without limitation, Adrenomedullin (AM), Angiopoietin (Ang), Autocrine motility factor, Bone morphogenetic proteins (BMPs), Brain-derived neurotrophic factor (BDNF), Epidermal growth factor (EGF), Erythropoietin (EPO), Fibroblast growth factor (FGF), Glial cell line-derived neurotrophic factor (GDNF), Granulocyte colony-stimulating factor (G-CSF), Granulocyte macrophage colony-stimulating factor (GM-CSF), Growth differentiation factor-9 (GDF9), Hepatocyte growth factor (HGF), Hepatoma-derived growth factor (HDGF), Insulin-like growth factor (IGF), Migration-stimulating factor, Myostatin (GDF-8), Nerve growth factor (NGF) and other neurotrophins, Platelet-derived growth factor (PDGF), Thrombopoietin (TPO), Transforming growth factor alpha(TGF-α), Transforming growth factor beta(TGF-β), Tumor necrosis factor-alpha (TNF-α), Vascular endothelial growth factor (VEGF), placental growth factor (P1GF), Foetal Bovine Somatotrophin (FBS) and IL-1-IL7.

Examples of peptide hormones that may be encoded by the genetic circuits of the present disclosure include, without limitation, Amylin (or Islet Amyloid Polypeptide), Antimullerian hormone (or Müllerian inhibiting factor or hormone), Adiponectin, Adrenocorticotropic hormone (or corticotropin), Angiotensinogen and angiotensin, Antidiuretic hormone (or vasopressin, arginine vasopressin), Atrial-natriuretic peptide (or atriopeptin), Brain natriuretic peptide, Calcitonin, Cholecystokinin, Corticotropin-releasing hormone, Enkephalin, Endothelin, Erythropoietin, Follicle-stimulating hormone, Galanin, Gastrin, Ghrelin, Glucagon, Gonadotropin-releasing hormone, Growth hormone-releasing hormone, Human chorionic gonadotropin, Human placental lactogen, Growth hormone, Inhibin, Insulin, Insulin-like growth factor (or somatomedin), Leptin, Lipotropin, Luteinizing hormone, Melanocyte stimulating hormone, Motilin, Orexin, Oxytocin, Pancreatic polypeptide, Parathyroid hormone, Prolactin, Prolactin releasing hormone, Relaxin, Renin, Secretin, Somatostatin, Thrombopoietin, Thyroid-stimulating hormone (or thyrotropin), and Thyrotropin-releasing hormone.

Examples of interferons (IFNs) that may be encoded by the genetic circuits of the present disclosure include, without limitation, IFN-α, IFN-β, IFN-ω and IFN-γ.

Examples of interleukins that may be encoded by the genetic circuits of the present disclosure include, without limitation, interleukin 1-17. In some embodiments, the interleukin is Interleukin-4, Interleukin-6, Interleukin-10, Interleukin-11 or Interleukin-13.

Other examples of therapeutic proteins that may be encoded by the genetic circuits of the inventionpresent disclosure include, without limitation, Insulin (blood glucose regulator), Pramlintide acetate (glucose control), Growth hormone GH (growth failure), Pegvisoman (growth hormone receptor antagonist), Mecasermin (IGF1, growth failure), Factor VIII (coagulation factor), Factor IX (coagulation factor, Protein C concentrate (anti-coagulation), α1-proteinase inhibitor (anti-trypsin inhibitor), Erythropoietin (stimulates erythropoiesis), Filgrastim (granulocyte colony-stimulating factor, G-CSF; stimulates neutrophil proliferation), Sargramostim36, 37 (granulocytemacrophage colony-stimulating factor, GM-CSF), Oprelvekin (interleukin11, IL11), Human follicle-stimulating hormone (FSH), Human chorionic gonadotropin (HCG), Lutropin-α (human luteinizing hormone), Interleukin 2 (IL2), Interleukin-1 Receptor Agonist, Denileukin diftitox (fusion of IL2 and Diphtheria toxin), Interferon alfacon 1 (consensus interferon), Interferon-α2a (IFNα2a), Interferon-α2b (IFNα2b), Interferon-αn3 (IFNαn3), Interferon-β1a (rIFN-β), Interferon-β1b (rIFN-β), Interferon-γ1b (IFNγ), Salmon calcitonin (32-amino acid linear polypeptide hormone), Teriparatide (part of human parathyroid hormone 1-34 residues), Exenatide (Incretin mimetic with actions similar to glucagon-like peptide 1), Octreotide (octapeptide that mimics natural somatostatin), Dibotermin-α (recombinant human bone morphogenic protein 2), Recombinant human bone morphogenic protein 7, Histrelin acetate (gonadotropin-releasing hormone; GnRH), Palifermin (Keratinocyte growth factor, KGF), Becaplermin (platelet-derived growth factor, PDGF), Nesiritide (recombinant human B-type natriuretic peptide), Lepirudin (recombinant variant of hirudin, another variant is Bivalirudin), Anakinra (interleukin 1 (IL1) receptor antagonist), Enfuviritide (an HIV-1 gp41-derived peptide), β-Glucocerebrosidase (hydrolyzes to glucose and ceramide), Alglucosidase-α (degrades glycogen), Laronidase (digests glycosaminoglycans within lysosomes), Idursulfase (cleaves O-sulfate preventing GAGs accumulation), Galsulfase (cleave terminal sulphage from GAGs), Agalsidase-β (human α-galactosidase A, hydrolyzes glycosphingolipids), Lactase (digest lactose), Pancreatic enzymes (lipase, amylase, protease; digest food), Adenosine deaminase (metabolizes adenosine), Tissue plasminogen activator (tPA, serine protease involved in the breakdown of blood clots), Factor VIIa (serine protease, causes blood to clot), Drotrecogin-α (serine protease, human activated protein C), Trypsin (serine protease, hydrolyzes proteins), Botulinum toxin type A (protease, inactivates SNAP-25 which is involved in synaptic vesicle fusion), Botulinum toxin type B (protease that inactivates SNAP-25 which is involved in synaptic vesicle fusion), Collagenase (endopeptidase, digest native collagen), Human deoxyribonuclease I (endonuclease, DNase I, cleaves DNA), Hyaluronidase (hydrolyzes hyaluronan), Papain (cysteine protease, hydrolyzes proteins), L-Asparaginase (catalyzes the conversion of L-asparagine to aspartic acid and ammonia), Rasburicase (urate oxidase, catalyzes the conversion of uric acid to allantoin), Streptokinase (Anistreplase is anisoylated plasminogen streptokinase activator complex (APSAC)), and Antithrombin III (serine protease inhibitor).

Reporter Molecules

In some embodiments, the genetic circuits of the present disclosure may encode a "reporter." As used herein, a reporter refers to a protein that can be used to measure gene expression and generally produce a measurable signal such as fluorescence, luminescence or color. The presence of a reporter in a cell or organism is readily observed. For example, fluorescent proteins (e.g., green fluorescent protein (GFP)) cause a cell to fluoresce when excited with light of a particular wavelength, luciferases cause a cell to catalyze a reaction that produces light, and enzymes such as β-galactosidase convert a substrate to a colored product. In some embodiments, reporters may be used to quantify the strength or activity of the input received by the systems of the present disclosure. In some embodiments, reporters can be fused in-frame to other protein coding sequences to identify where a protein is located in a cell or organism. Reporters for use in accordance with the present disclosure include any reporter described herein or known to one of ordinary skill in the art.

There are several different ways to measure or quantify a reporter depending on the particular reporter and what kind of characterization data is desired. In some embodiments, microscopy can be a useful technique for obtaining both spatial and temporal information on reporter activity, particularly at the single cell level. In some embodiments, flow cytometers can be used for measuring the distribution in reporter activity across a large population of cells. In some embodiments, plate readers may be used for taking population average measurements of many different samples over time. In some embodiments, instruments that combine such various functions, may be used, such as multiplex plate readers designed for flow cytometers, and combination microscopy and flow cytometric instruments.

Fluorescent proteins may be used for visualizing or quantifying gene product expression. Fluorescence can be readily quantified using a microscope, plate reader or flow cytometer equipped to excite the fluorescent protein with the appropriate wavelength of light. Several different fluorescent proteins are available, thus multiple gene expression measurements can be made in parallel. Examples of genes encoding fluorescent proteins that may be used in accordance with the present disclosure include, without limitation, those proteins provided in U.S. Patent Application No. 2012/0003630 (see Table 59), incorporated herein by reference.

Luciferases may also be used for visualizing or quantifying gene product expression, particularly for measuring low levels of gene expression, as cells tend to have little to no background luminescence in the absence of a luciferase. Luminescence can be readily quantified using a plate reader or luminescence counter. Examples of genes encoding luciferases for that may be used in accordance with the present disclosure include, without limitation, dmMyD88-linker-Rluc, dmMyD88-linker-Rluc-linker-PEST191, luxAB, NanoLuc, *Renilla reniformis* luciferase, and firefly luciferase (from *Photinus pyralis*).

Enzymes that produce colored substrates ("colorimetric enzymes") may also be used for visualizing or quantifying gene product expression. Enzymatic products may be quantified using spectrophotometers or other instruments that can take absorbance measurements including plate readers. Like luciferases, enzymes such as β-galactosidase can be used for measuring low levels of gene expression because they tend to amplify low signals. Examples of genes encoding colorimetric enzymes that may be used in accordance with the present disclosure include, without limitation, lacZ alpha fragment, lacZ (encoding beta-galactosidase, full-length), and xylE.

Transcriptional Activators and/or Repressors

In some embodiments, the genetic circuits of the present disclosure may encode a transcriptional activator or repressor, the production of which can result in a further change in state of the cell, and provide additional input signals to subsequent or additional genetic circuits. Transcriptional regulators either activate or repress transcription from cognate promoters. Transcriptional activators typically bind nearby to transcriptional promoters and recruit RNA polymerase to directly initiate transcription. Repressors bind to transcriptional promoters and sterically hinder transcriptional initiation by RNA polymerase. Other transcriptional regulators serve as either an activator or a repressor depending on where it binds and cellular conditions. Transcriptional regulators for use in accordance with the present disclosure include any transcriptional regulator described herein or known to one of ordinary skill in the art. Examples of genes encoding transcriptional regulators that may be used in accordance with the present disclosure include, without limitation, those regulators provided in U.S. Patent Application No. 2012/0003630 (see Table 63), incorporated herein by reference.

Enzymes

In some embodiments, the genetic circuits of the present disclosure may encode an enzyme. In some embodiments, an enzyme is used as a response to a particular input. For example, in response to a particular input received by a genetic circuit of the present disclosure, such as a certain range of toxin concentration present in the environment, the system may activate transcription of nucleic acid sequence that encodes an enzyme that can degrade or otherwise destroy the toxin. In some embodiments, enzymes may be "biosynthetic enzymes" that catalyze the conversion of substrates to products. For example, such biosynthetic enzymes can be used in accordance with the present disclosure to assemble pathways that produce or degrade useful chemicals and materials, in response to specific signals. These combinations of enzymes can reconstitute either natural or synthetic biosynthetic pathways. Enzymes for use in accordance with the present disclosure include any enzyme described herein or known to one of ordinary skill in the art. Examples of genes encoding enzymes that may be used in accordance with the present disclosure include, without limitation, those provided in U.S. Patent Application No. 2012/0003630, incorporated herein by reference.

Receptors, Ligands, and Lytic Proteins

In some embodiments, the genetic circuits of the present disclosure may encode a receptor, ligand or lytic protein. Receptors tend to have three domains: an extracellular domain for binding ligands such as proteins, peptides or small molecules, a transmembrane domain and an intracellular or cytoplasmic domain, which frequently can participate in some sort of signal transduction event such as phosphorylation. In some embodiments, transporters, channels or pumps are used as output products. Transporters are membrane proteins responsible for transport of substances across the cell membrane. Channels are made up of proteins that form transmembrane pores through which selected to ions can diffuse. Pumps are membrane proteins that can move substances against their gradients in an energy-dependent process known as active transport. In some embodiments, nucleic acid sequences encoding proteins and protein domains whose primary purpose is to bind other proteins, ions, small molecules, and other ligands may be used in accordance with the present disclosure. Receptors, ligands and lytic proteins for use in accordance with the present disclosure include any receptor, ligand and lytic protein, described herein or known to one of ordinary skill in the art. Examples of genes encoding receptors, ligands and lytic proteins that may be used in accordance with the present disclosure include, without limitation, those provided in U.S. Patent Application No. 2012/0003630 (see Table 73), incorporated herein by reference.

Antimicrobial Proteins/Peptides

In some embodiments, the at least one genetic circuit may express an antimicrobial protein and/or peptide. However, it is to be understood that such antimicrobial proteins and/or peptides may be specifically excluded from the genetic circuits of the present disclosure. Thus, in some embodiments, the at least one genetic circuit does not express an antimicrobial protein or peptide. Examples of antimicrobial proteins and/or peptides contemplated herein include gene modules that encode instructions for cell death, or bactericidal proteins. Examples of such gene modules include pemI-pemK genes of plasmid R100, the phd-doc genes of phage P1, the ccdA-ccdB genes of plasmid F, mazE-mazF (or chpAI-chpAK), sof-gef, kicA-kicB, relB-relE, chpBI-chpBK and gef. Other examples of antimicrobial proteins and/or peptides include, without limitation, bacteriocins, hydramacin-1, cecropins, moricins, papiliocins, poneratoxins, mastoparansi, melittins, spinigerins, cupiennins, oxyopinins, magainins, dermaseptins, cathelicidins, defensins and protegrins. Other antimicrobial proteins and/or peptides are also contemplated by the present disclosure.

Engineering Genetic Circuits

The genetic circuits of the present disclosure may be engineered using, for example, standard molecular cloning methods (see, e.g., *Current Protocols in Molecular Biology*, Ausubel, F. M., et al., New York: John Wiley & Sons, 2006; Gibson, D. G., et al., *Nature Methods* 6(5):343-345 (2009), the teachings of which relating to molecular cloning are herein incorporated by reference).

Uses of Functionalized Bacteria

A genetic circuit, in accordance with the present disclosure, may be engineered to impart to endogenous bacteria a variety of functions such as, for example, the ability to express therapeutic molecules, to modify cellular functions, to create cellular responses to environmental conditions, and/or influence cellular development. By providing a method of delivering rational, controllable genetic circuits to bacterial cells of a microbiome in vivo, in some embodiments, the present disclosure permits the use of such cells as engineered systems to perform a vast range of useful functions that may greatly benefit the host organism.

The functionalized endogenous bacterial cells of the present disclosure may be used for a variety of applications, including, without limitation, bioremediation, biosensing and biomedical therapeutics. In some embodiments, the genetic circuits may be used to build in the endogenous bacterial cells multiplexed cellular switches for gene expression or synthetic differentiation cascades. In some embodiments, the genetic circuits may be used to regulate (e.g., activate and/or deactivate) in the same cell, at the same time or sequentially, transcription of various molecules of interest.

In some embodiments, the methods of the present disclosure may be used to deliver molecules that treat, or alleviate the symptoms associated with, a condition such as, for example, cancer (e.g., gastrointestinal cancer), immune disorders, infections and/or other diseases (e.g., gastrointestinal disease). Thus, in some embodiments, the present disclosure provides methods of delivering to a subject a recombinant bacteriophage (e.g., coliphage) and/or phagemid engineered to contain at least one genetic circuit. In some embodiments, the genetic circuit comprises a nucleic acid with a promoter operably linked to a nucleotide sequence encoding a therapeutic molecule. The therapeutic molecule may be, for example, an antibody, antibody-based drug, Fc fusion protein, anticoagulant, blood factor, bone morphogenetic protein, engineered protein scaffold, enzyme, growth factor, hormone, interferon, interleukin or thrombolytic.

Examples of gastrointestinal cancers include, without limitation, cancers of the esophagus, gallbladder, liver, pancreas, stomach, small intestine, large intestine (colon) and rectum.

Examples of immune diseases include, without limitation, Acute Disseminated Encephalomyelitis (ADEM), Acute necrotizing hemorrhagic leukoencephalitis, Addison's disease, Agammaglobulinemia, Alopecia greata, Amyloidosis, Ankylosing spondylitis, Anti-GBM/Anti-TBM nephritis, Antiphospholipid syndrome (APS), Autoimmune angioedema, Autoimmune aplastic anemia, Autoimmune dysautonomia, Autoimmune hepatitis, Autoimmune hyperlipidemia, Autoimmune immunodeficiency, Autoimmune inner ear disease (AIED), Autoimmune myocarditis, Autoimmune oophoritis, Autoimmune pancreatitis, Autoimmune retinopathy, Autoimmune thrombocytopenic purpura (ATP), Autoimmune thyroid disease, Autoimmune urticaria, Axonal & neuronal neuropathies, Balo disease, Behcet's disease, Bullous pemphigoid, Cardiomyopathy, Castleman disease, Celiac disease, Chagas disease, Chronic fatigue syndrome**, Chronic inflammatory demyelinating polyneuropathy (CIDP), Chronic recurrent multifocal ostomyelitis (CRMO), Churg-Strauss syndrome, Cicatricial pemphigoid/benign mucosal pemphigoid, Crohn's disease, Cogans syndrome, Cold agglutinin disease, Congenital heart block, Coxsackie myocarditis, CREST disease, Essential mixed cryoglobulinemia, Demyelinating neuropathies, Dermatitis herpetiformis, Dermatomyositis, Devic's disease (neuromyelitis optica), Discoid lupus, Dressler's syndrome, Endometriosis, Eosinophilic esophagitis, Eosinophilic fasciitis, Erythema nodosum, Experimental allergic encephalomyelitis, Evans syndrome, Fibromyalgia, Fibrosing alveolitis, Giant cell arteritis (temporal arteritis), Giant cell myocarditis, Glomerulonephritis, Goodpasture's syndrome, Granulomatosis with Polyangiitis (GPA) (formerly called Wegener's Granulomatosis), Graves' disease, Guillain-Barre syndrome, Hashimoto's encephalitis, Hashimoto's thyroiditis, Hemolytic anemia, Henoch-Schonlein purpura, Herpes gestationis, Hypogammaglobulinemia, Idiopathic thrombocytopenic purpura (ITP), IgA nephropathy, IgG4-related sclerosing disease, Immunoregulatory lipoproteins, Inclusion body myositis, Interstitial cystitis, Juvenile arthritis, Juvenile diabetes (Type 1 diabetes), Juvenile myositis, Kawasaki syndrome, Lambert-Eaton syndrome, Leukocytoclastic vasculitis, Lichen planus, Lichen sclerosus, Ligneous conjunctivitis, Linear IgA disease (LAD), Lupus (SLE), Lyme disease, chronic, Meniere's disease, Microscopic polyangiitis, Mixed connective tissue disease (MCTD), Mooren's ulcer, Mucha-Habermann disease, Multiple sclerosis, Myasthenia gravis, Myositis, Narcolepsy, Neuromyelitis optica (Devic's), Neutropenia, Ocular cicatricial pemphigoid, Optic neuritis, Palindromic rheumatism, PANDAS (Pediatric Autoimmune Neuropsychiatric Disorders Associated with *Streptococcus*), Paraneoplastic cerebellar degeneration, Paroxysmal nocturnal hemoglobinuria (PNH), Parry Romberg syndrome, Parsonnage-Turner syndrome, Pars planitis (peripheral uveitis), Pemphigus, Peripheral neuropathy, Perivenous encephalomyelitis, Pernicious anemia, POEMS syndrome, Polyarteritis nodosa, Type I, II, & III autoimmune polyglandular syndromes, Polymyalgia rheumatica, Polymyositis, Postmyocardial infarction syndrome, Postpericardiotomy syndrome, Progesterone dermatitis, Primary biliary cirrhosis, Primary sclerosing cholangitis, Psoriasis, Psoriatic arthritis, Idiopathic pulmonary fibrosis, Pyoderma gangrenosum, Pure red cell aplasia, Raynauds phenomenon, Reactive Arthritis, Reflex sympathetic dystrophy, Reiter's syndrome, Relapsing polychondritis, Restless legs syndrome, Retroperitoneal fibrosis, Rheumatic fever, Rheumatoid arthritis, Sarcoidosis, Schmidt syndrome, Scleritis, Scleroderma, Sjogren's syndrome, Sperm & testicular autoimmunity, Stiff person syndrome, Subacute bacterial endocarditis (SBE), Susac's syndrome, Sympathetic ophthalmia, Takayasu's arteritis, Temporal arteritis/Giant cell arteritis, Thrombocytopenic purpura (TTP), Tolosa-Hunt syndrome, Transverse myelitis, Type 1 diabetes, Ulcerative colitis, Undifferentiated connective tissue disease (UCTD), Uveitis, Vasculitis, Vesiculobullous dermatosis, Vitiligo and Wegener's granulomatosis (also referred to as Granulomatosis with Polyangiitis (GPA)).

The methods of the present disclosure may be used to deliver molecules that treat, or alleviate the symptoms associated with, gastrointestinal diseases. Examples of gastrointestinal diseases include, without limitation, Crohn's disease, ulcerative colitis and colon cancer.

Crohn's disease is a condition of chronic inflammation potentially involving any location of the gastrointestinal tract, but it frequently affects the end of the small bowel and the beginning of the large bowel. In Crohn's disease, all layers of the intestine may be involved, and there can be normal healthy bowel in between patches of diseased bowel. Symptoms include persistent diarrhea (loose, watery, or frequent bowel movements), cramping abdominal pain, fever, and, at times, rectal bleeding. Loss of appetite and weight loss also may occur. However, the disease is not always limited to the gastrointestinal tract; it can also affect the joints, eyes, skin and liver. Fatigue is another common symptom. In some embodiments, the methods of the present disclosure are used to deliver to endogenous bacterial cells a genetic circuit that expresses gene(s) encoding the monoclonal antibody, infliximab, Interleukin-4, Interleukin-6, Interleukin-10, Interleukin-11, Interleukin-13, or Interleukin-1 Receptor Antagonist. In some embodiments, the present disclosure provides methods of delivering to a subject having Crohn's disease a recombinant bacteriophage (e.g., coliphage) and/or phagemid engineered to contain at least one genetic circuit. In some embodiments, the genetic circuit comprises a nucleic acid with a promoter operably linked to a nucleotide sequence encoding a monoclonal antibody (e.g., infliximab), Interleukin-4, Interleukin-6, Interleukin-10, Interleukin-11, Interleukin-13, or Interleukin-1 Receptor Antagonist.

Ulcerative colitis is a chronic gastrointestinal disorder that is limited to the large bowel (the colon). Ulcerative colitis does not affect all layers of the bowel, but only affects the top layers of the colon in an even and continuous distribution. The first symptom of ulcerative colitis is a progressive loosening of the stool. The stool is generally bloody and may be associated with cramping abdominal pain and severe urgency to have a bowel movement. The diarrhea may begin slowly or quite suddenly. Loss of appetite and subsequent weight loss are common, as is fatigue. In cases of severe bleeding, anemia may also occur. In addition, there may be skin lesions, joint pain, eye inflammation and liver disorders. Children with ulcerative colitis may fail to develop or grow properly. In some embodiments, the methods of the present disclosure are used to deliver to endogenous bacterial cells a genetic circuit that expresses gene(s) encoding Interleukin-4, Interleukin-6, Interleukin-10, Interleukin-11, Interleukin-13, or Interleukin-1 Receptor Antagonist. In some embodiments, the present disclosure provides methods of delivering to a subject having ulcerative colitis a recombinant bacteriophage (e.g., coliphage) and/or phagemid engineered to contain at least one genetic circuit. In some embodiments, the genetic circuit comprises a nucleic acid with a promoter operably linked to a nucleotide sequence encoding a monoclonal antibody (e.g., infliximab), Interleukin-4, Interleukin-6, Interleukin-10, Interleukin-11, Interleukin-13, or Interleukin-1 Receptor Antagonist.

In some embodiments, the present disclosure provides methods of delivering to a subject having colon cancer a recombinant bacteriophage (e.g., coliphage) and/or phagemid that is engineered to contain at least one genetic circuit.

EXAMPLES

Example 1

Indigo Networks on Plasmids

Two different oxidative enzymes were chosen for the purpose of converting indole, a metabolite of Tryptophan, to indigo, an insoluble dye. The first enzyme, toluene dioxygenase, is found in the organism *Pseudomonas putida* and is responsible for catalyzing the oxygenation of various ethenes, butenes, and propenes (Woo et al. *Journal of Microbiological Methods* 40, 181-191 (2000)). Toulene dioxygenase (e.g., TODC1C2AB) is a multicomponent enzyme that primarily converts indole to indolediol, which is then dimerized spontaneously to indigo. Styrene monooxygenase is also found in *Pseudomonas putida* and is responsible for degrading various styrene molecules (O'Connor et al. *Applied and Environmental Microbiology* 63, 4287-4291 (1997)). Styrene monooxygenase is made up of two components, StyA and StyB. StyA slowly catalyzes the conversion of indole to indole oxide, which can naturally form 2-oxindole before dimerizing to indigo. StyB converts indole oxide to indoxyl, which forms indigo at a much faster pace. Both enzymes are capable of oxidizing indole and subsequently catalyzing its dimerization to form indigo in vivo. Once formed, the indigo can diffuse through the cell membrane and into the extracellular fluid, where at high enough concentrations it aggregates (Pinero-Fernandez et al. *Journal of Bacteriology* 193:1793-1798 (2011)).

The indole networks were designed to be either constitutive or inducible. The PltetO promoter is constitutive unless inhibited by the tetR protein, which is not expressed in wild type *E. coli*. The Pbad promoter is induced by the small molecule arabinose in a dose-dependent manner. Ribosomal binding sites (RBSs) were optimized for high expression by using a RBS calculator.

Cloning

Cloning was accomplished through standard methods. The oxidative enzymes were obtained by PCR amplification from published strains, using primers specific for the 5' and 3' ends. The 5' primer included the designed RBS. Promoter and terminator elements were obtained by PCR from published library plasmids described by Litcofsky et al. (*Nat Meth* 9(11):1077-1080 (2012). These purified components were then digested and ligated into the multiple cloning site of the pKE2-MCS cloning plasmid also described by Litcofsky et al. The ligated plasmid was then transformed into the test strain MgPro, which is designed to overexpress the tetR and lacI cassettes.

Indigo Production

Indigo networks were grown overnight in lysogeny broth (LB), then diluted 1:1000 in M9 minimal media (e.g., M9 salts, $MgSO_4$, $CaCl_2$, carbon source such as, e.g., glycerol, or glucose). At OD ~0.2-0.3, 0.5 µM indole and the respective inducer were added to the media, and samples were collected every hour for four hours. The samples were spun down for one minute at 13 k rpm, aspirated and brought up in dimethyl sulfoxide (DMSO). After vortexing, the samples were spun again at 13 k rpm before being read on a plate reader at 610 nm Pbad was induced with 0.01% arabinose. PltetO was induced with 0.5 µg/mL aTe.

Results

Figure 2:
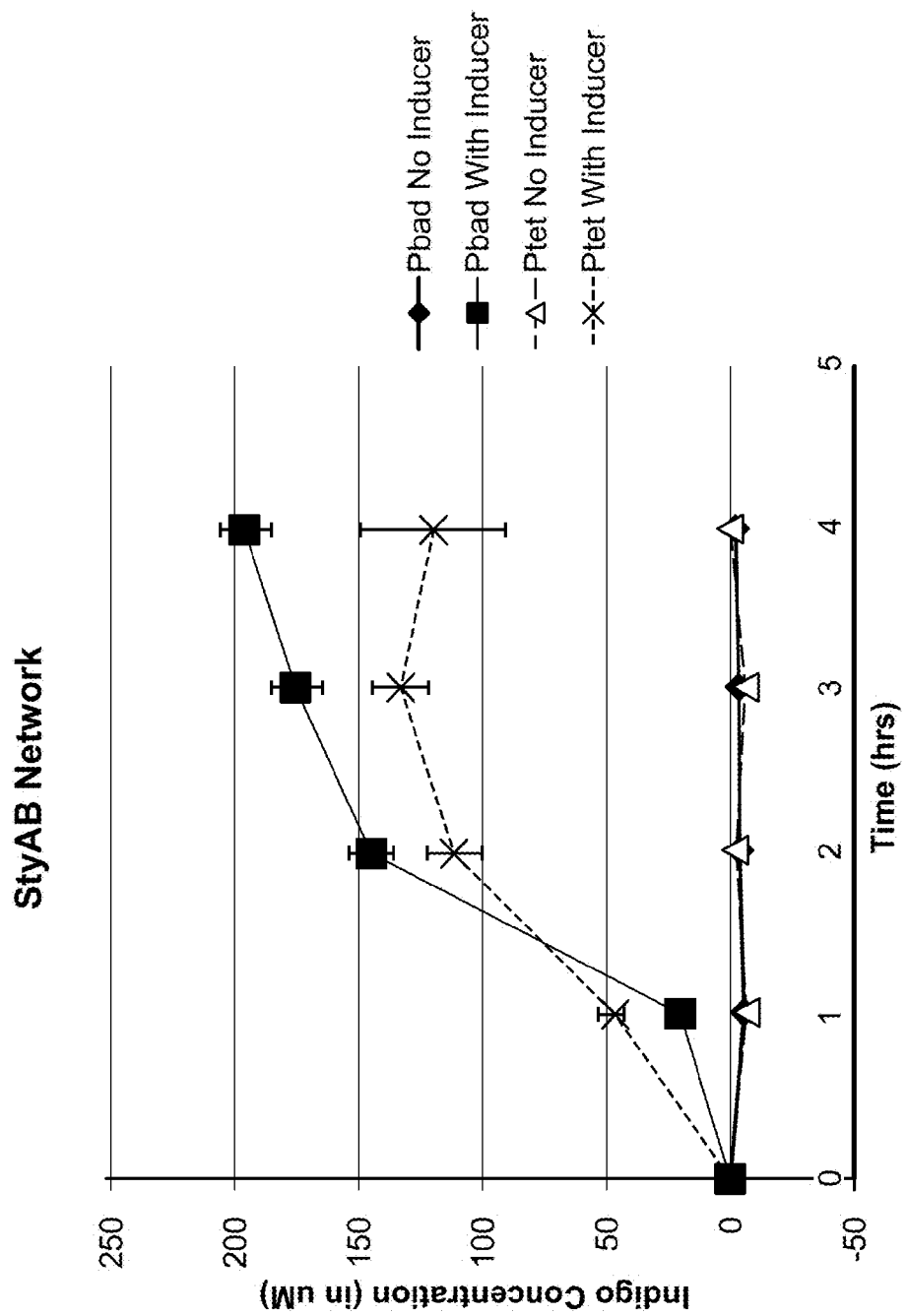
FIG. 2 shows a graph of indigo concentration over time for the constitutive PLtet0 and the inducible Pbad promoter networks used to express styrene monooxygenase. Styrene monooxygenase (and, thus, indigo) is produced in the presence of the Pbad inducer and in the presence of the Ptet inducer.
Figure 3:
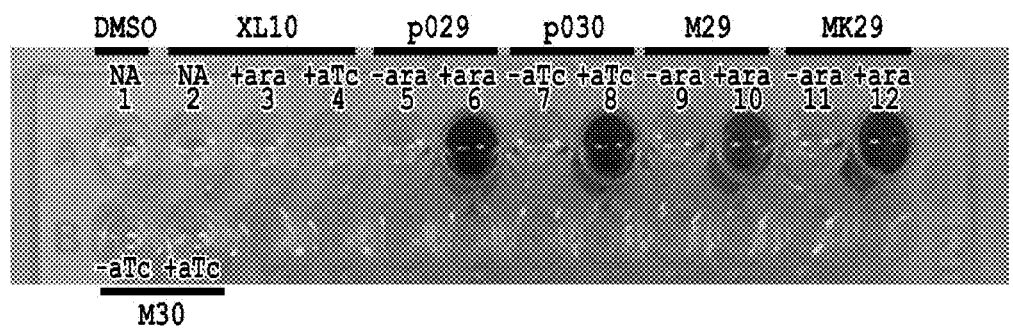
FIG. 3 depicts a graph of indigo measurements after overnight infection of bacteria with recombinant M13 bacteriophage harboring different plasmids.
Figure 3:
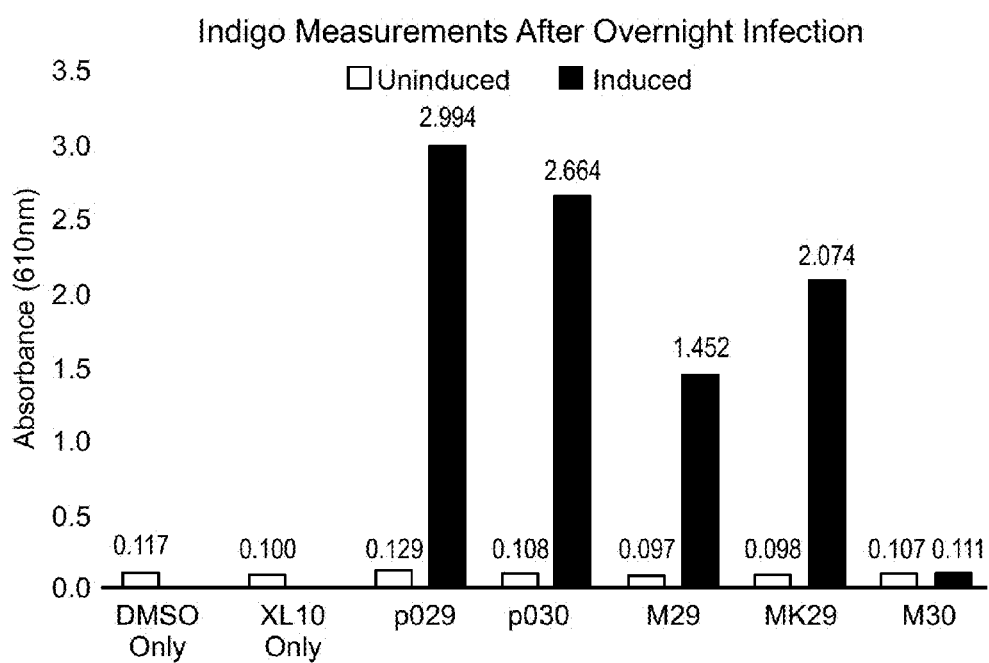
Figure 4:
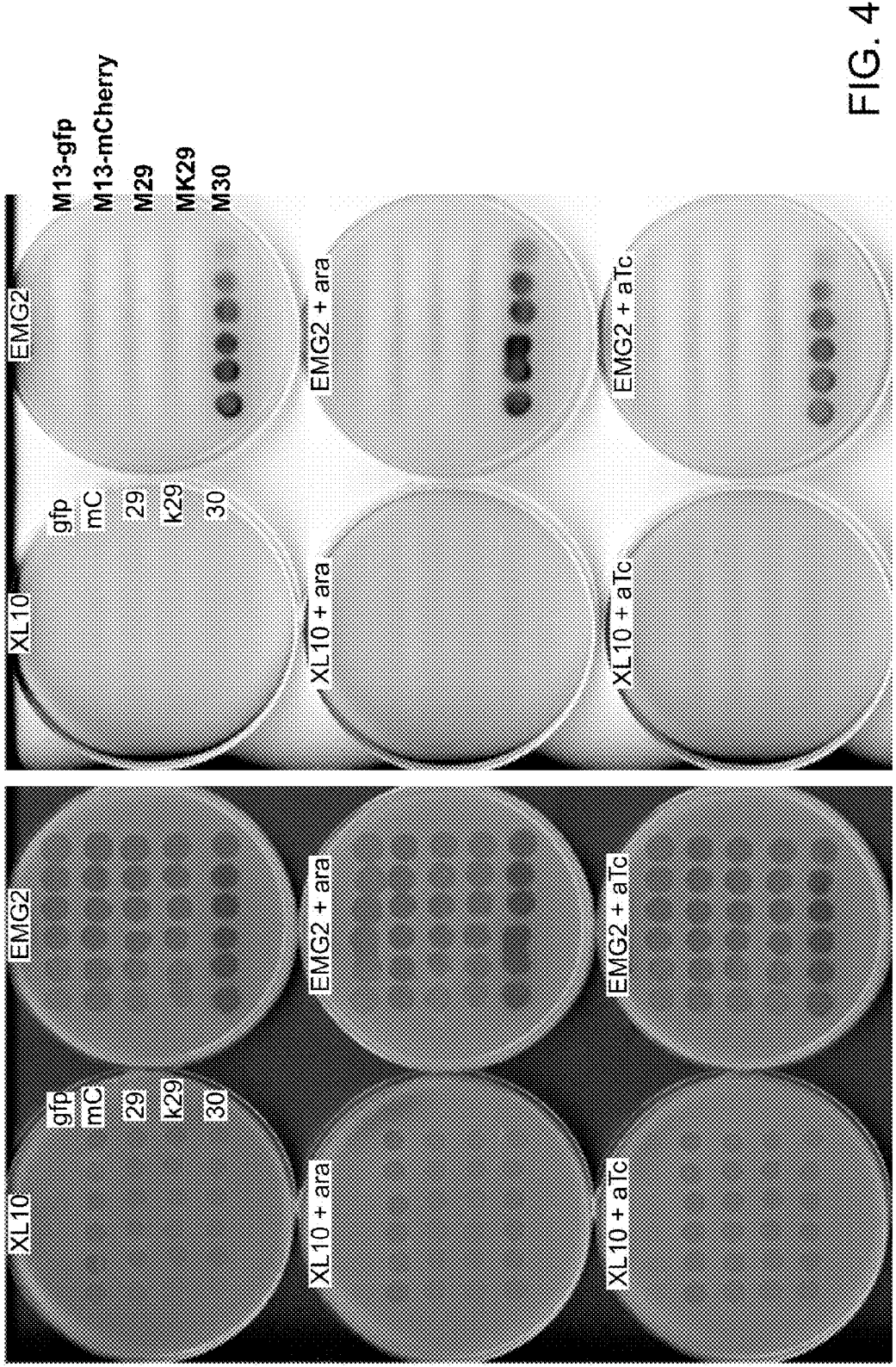
FIG. 4 shows images of plates from an overnight spot test of M13-pBAD-029, M13-kan-029 and M13-pTet-030. Image on the left is with a black backdrop; image on the right is with a white backdrop. For each plate, the spots from top to bottom are: M13-gfp, M13-mCherry, M13-pBAD-styAB, M13-kan-pBAD-styAB, and M13-pTet-styAB. Spots represent a 1:10 dilution series from right to left, starting with 7.5 μL of stock.

As shown in FIGS. 1A and 1B, indigo was produced using both the constitutive PLtet0 and the inducible Pbad promoter systems for the production of toluene dioxygenase, TODC1C2AB. Similarly, as shown in FIGS. 2A and 2B, indigo was produced using both the constitutive PLtet0 and the inducible Pbad promoter systems for the production of styrene monooxygenase, StyAB. By contrast, as shown in FIG. 2C, little indigo was produced using both the constitutive PLtet0 and the inducible Pbad promoter systems for the production of StyA.

Example 2

Transducible Expression of styAB Using Engineered M13 Phage

One important aspect of engineering genetic circuits that has yet to be thoroughly explored is the ability to deliver and introduce functioning circuits into cells under in situ or in vivo conditions. Embodiments of the present disclosure provide engineered M13 bacteriophage for delivery of such circuits into a target population. The recombinant bacteriophages provided herein are used to deliver genetic circuits in vivo by targeting bacteria in the intestines of mice. This technology has broad applications as a platform for circuit delivery in order to apply some of the exciting creations of synthetic biology such as intricate biosensors to real-life animal models.

M13mp18 replicative form DNA was acquired from NEB (#N4018S) and used for the genetic manipulations of M13 phage. *E. coli* XL10, a cloning strain of bacteria harboring the F plasmid required for M13 infection, was used for cloning and M13 propagation and was grown in LB with 25 µg/mL chloramphenicol. Briefly, the desired genetic circuits were amplified from template plasmid and cloned in vitro into the multiple cloning site of M13mp18. The ligation products were transformed and plated in 0.7% LB top agar along with 200 µL of additional bacteria from overnight culture to generate a bacterial lawn with plaques corresponding to M13 infection foci. Plaques were picked into a 1:3 dilution of overnight XL10 culture in fresh LB and grown for 4 hours to overnight at 37° C. Culture supernatants were sterile-filtered to collect crude phage preparations, and pellets were subjected to alkaline lysis using QIAGEN® Miniprep Kits for sequencing.

For initial phenotype verification, an overnight culture of *E. coli* EMG2 (F+) was washed once and subsequently resuspended in M9 plus glucose. Cultures of *E. coli* MG1655Pro harboring the template plasmids used for cloning into M13 were prepared as positive controls in the same manner. Washed cell suspensions were diluted four-fold into fresh M9 plus glucose with 10 mM arabinose (ara), 250 ng/µL anhydrotetracycline (aTc), or neither. Phage supernatants as prepared above were added at 1:100, and cultures were incubated at 37° C. with shaking. After 4 hours, indole was supplemented to a final concentration of 0.25 mM, and cultures were returned to incubate overnight. Indigo production was visualized the following day by spinning down cultures and resuspending in DMSO.

Next, phage spot testing was performed to test for the generation of visibly indole-converting plaques. Briefly, 0.25 mM indole and 10 mM ara or 250 ng/µL aTc (or neither) was added to 3 mL of top agar along with 300 µL of EMG2 cells or XL10 cells overnight culture. After solidification, 7.5 µL of test phage and a 1:10 dilution series were added onto the top agar. Plates were incubated overnight at 37° C. and imaged/read one day late (Table 1).

5. Cultures grown for 4 hrs at 37° C. in shaking incubator.
6. Indole added to a final concentration of 500 µM, grown for 2 hours, then assessed for Indigo production.

TABLE 1

| | 1 | 2 | 3 | 4 | 5 | 6 | 7 | 8 | 9 | |
|---|---|---|---|---|---|---|---|---|---|---|
| F | 0.041 M9 | 1.533 p29 + ara | 1.349 p30 + aTc | 0.494 M29 | 1.256 M29 + ara | 0.482 Mk29 | 1.292 Mk29 + ara | 1.041 M30 | 0.991 M30 + aTc | 610 |

Figure 5:
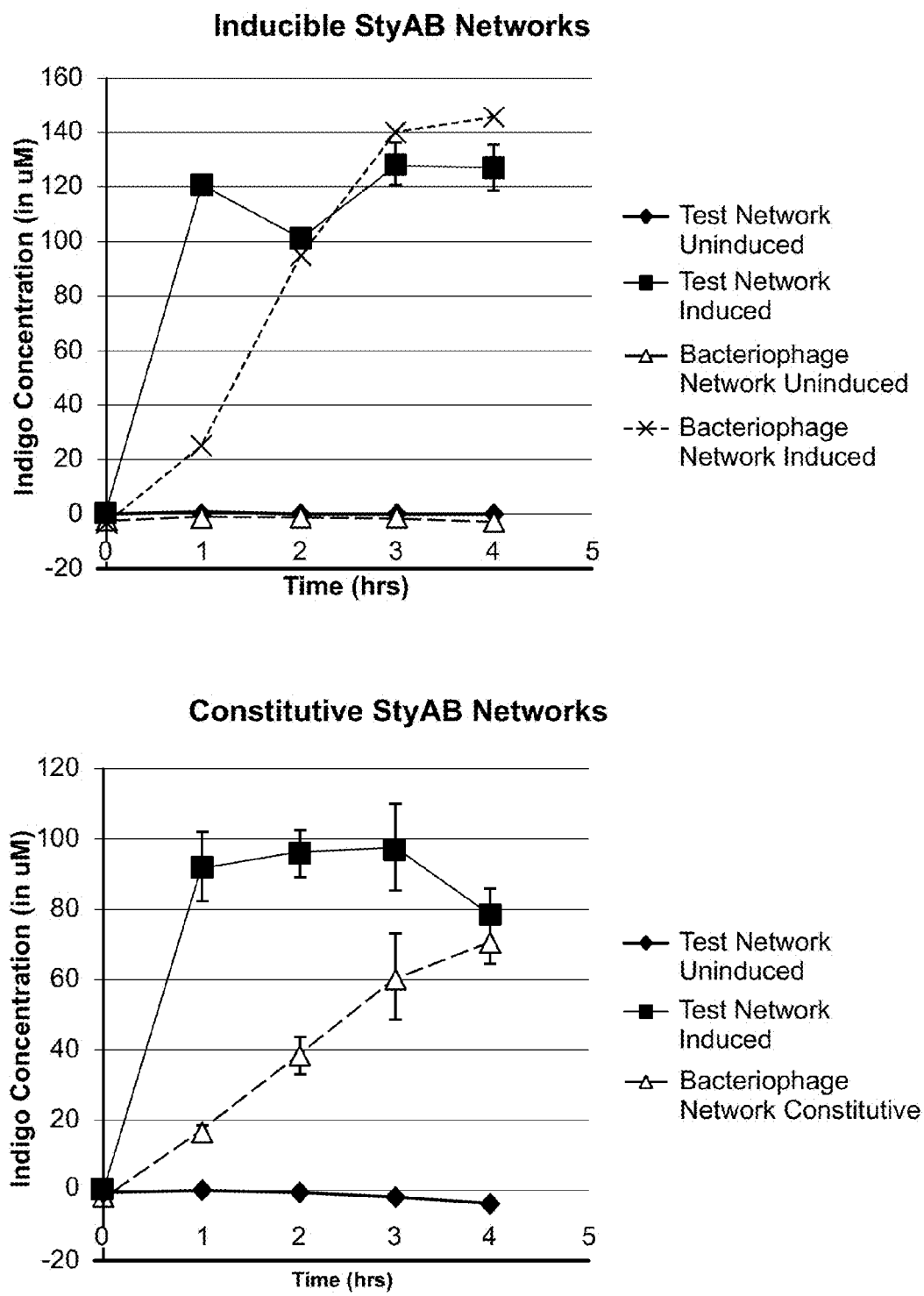
FIG. 5 shows a graph of indigo concentration over time produced by bacteria transformed with the inducible Pbad promoter network expressing styrene monooxygenase ("test network") or infected with recombinant M13 bacteriophage harboring the inducible Pbad promoter network expressing styrene monooxygenase ("bacteriophage network") (top).
Figure 6:
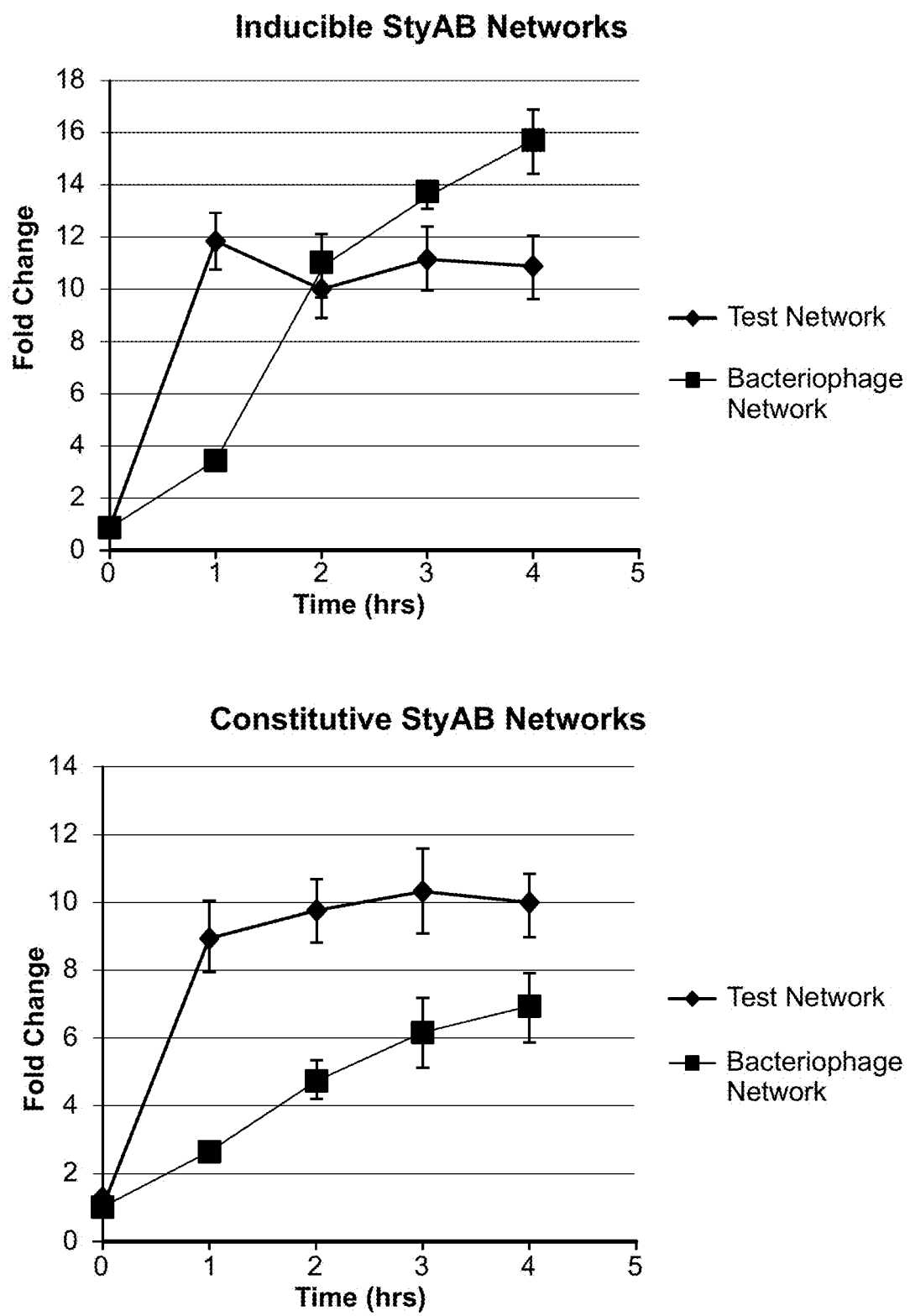
FIG. 6 shows a graph of the fold change of the concentration of indigo produced over time by bacteria transformed with the inducible Pbad test network versus bacteria infected with the inducible Pbad bacteriophage network (top).

This experiment revealed inducible expression of the indole-converting circuit for pBAD-styAB and pITetO-styAB constructs carried on the engineered M13 bacteriophages (FIGS. 5 and 6).

Strains:
pRJK029=MG1655Pro harboring a plasmid carrying pBAD-driven styAB;
pRJK030=MG1655Pro harboring a plasmid carrying pTet-driven styAB;
M029=EMG2 infected with M13 phage carrying pBAD-driven styAB;
M-k29=EMG2 infected with M13 phage carrying pBAD-driven styAB and a kanamycin resistance cassette; and
M030=EMG2 infected with M13 phage carrying pTet-driven styAB.

Inducers:
+ara=with 10 mM arabinose
+aTc=with 2.5 µg/mL anhydrotetracycline
M13-Indole Overnight Induction Repeat The initial infection assay was repeated using XL10 as the recipient strain for M13 infection instead of EMG2.

The cultures were spun down at 4000 rpm for 15 min, and the pellets were resuspended in 500 µL DMSO. The resuspended pellet was transferred to 1.5 mL tubes and incubated at 60° C. with mixing for 5 min to dissolve the indigo. The dissolved indigo was spun at 10,000×g for 5 min. 300 µL of the supernatant was collected for an absorbance reading at 610 nm.

This experiment revealed inducible expression of the indole-converting circuit for both pBAD-styAB constructs carried on the engineered M13 bacteriophages. The XL10 recipient failed to show indole conversion with the M13-pTet-styAB construct, however. Since only one inducer concentration was tested, this should be optimized for M13-pTet-styAB, which was previously verified as functional using EMG2 as the recipient strain. EMG2 infected with M13-pTet-styAB looked darker than other spots when held against a white background. They looked less dark towards more concentrated phage treatment. Without being bound by theory, it is possible that the growth of bacteria is too slowed to visualize a phenotype at the higher concentrations of phage.

Example 3

Dose-Response Study of Indigo Production in Bacterial Cells Infected with Bacteriophage M029

Phage Delivery:
1. EMG2 or XL10 cells grown to stationary phase overnight.
2. Cultures washed 2× in M9 minimal media.
3. Cultures diluted 1:4 into experimental conditions.
4. Phage preps added 1:100 as well as dilutions of 10% arabinose (no inducer, 1:400, 1:200, 1:100, 1:50, 1:25, 1:12.5).
5. Cultures grown for 4 hrs at 37° C. in shaking incubator.
6. Indole added to a final concentration of 500 µM, grown for 2 hours, then assessed for Indigo production.

Indigo Collection:
1. Indigo collected from culture by spinning sample at 15 k rpm for 2 min.
2. Supernatant removed.
3. DMSO added back to recover original volume amount.
4. Pellet resuspended and mixed.
5. Samples incubated at 70° C. for 10 min to ensure all indigo dissolves into solution.
6. Samples spun down again at 15 k for 2 min.
7. 300 µL of sample added to a 96 well plate and read on a plate reader at 610 nm for OD.

Figure 7:
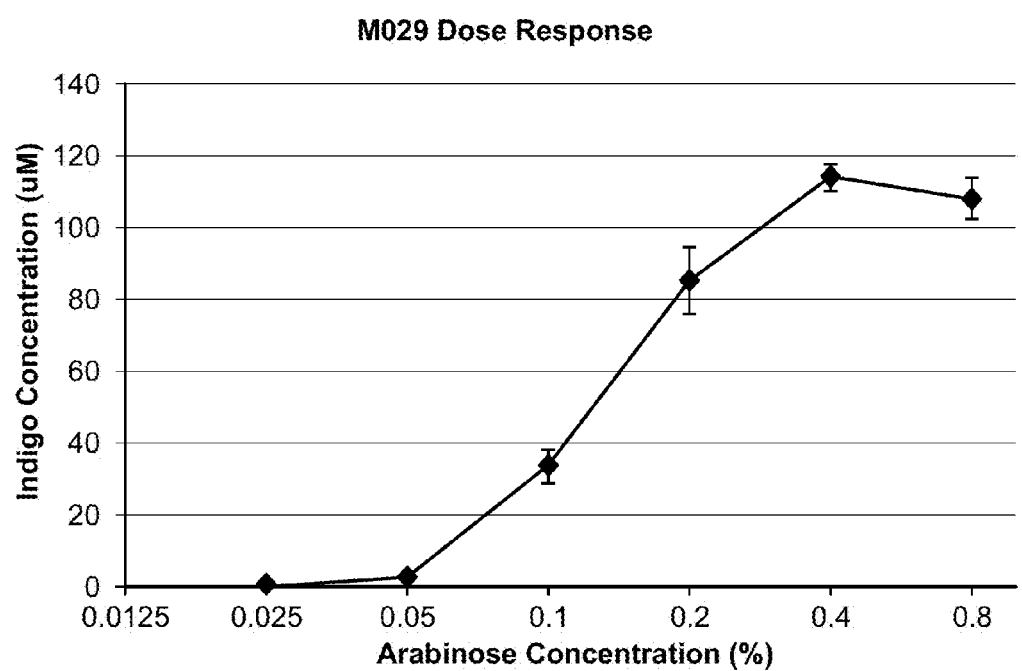
FIG. 7 shows a graph of indigo concentration as a function of arabinose inducer dosage. EMG2 cells were infected with M13 bacteriophage carrying the inducible Pbad promoter network expressing styrene monooxygenase (M029).
Figure 8A:
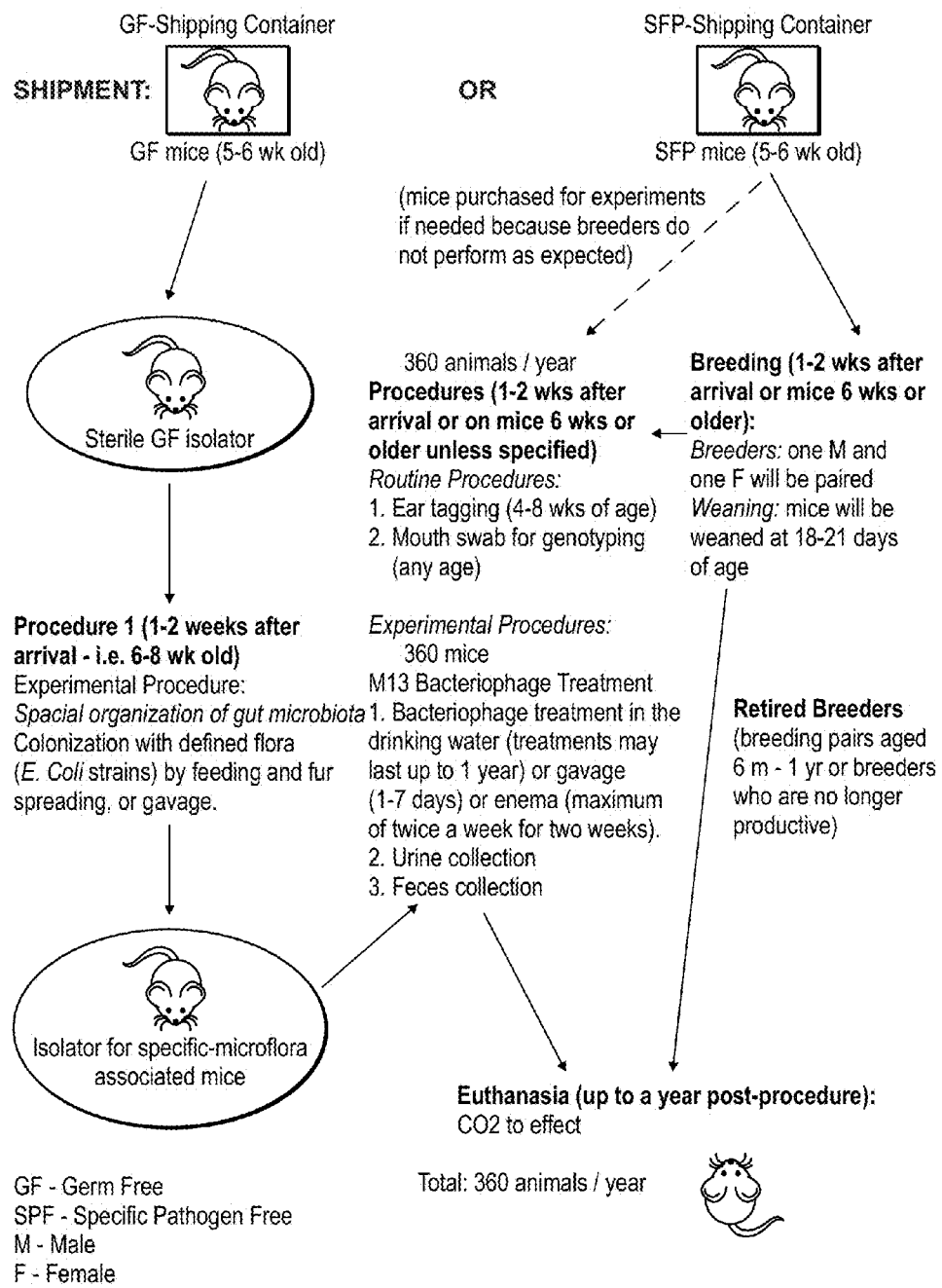
FIG. 8A depicts a schematic of a general in vivo model of the present disclosure.
Figure 8B:
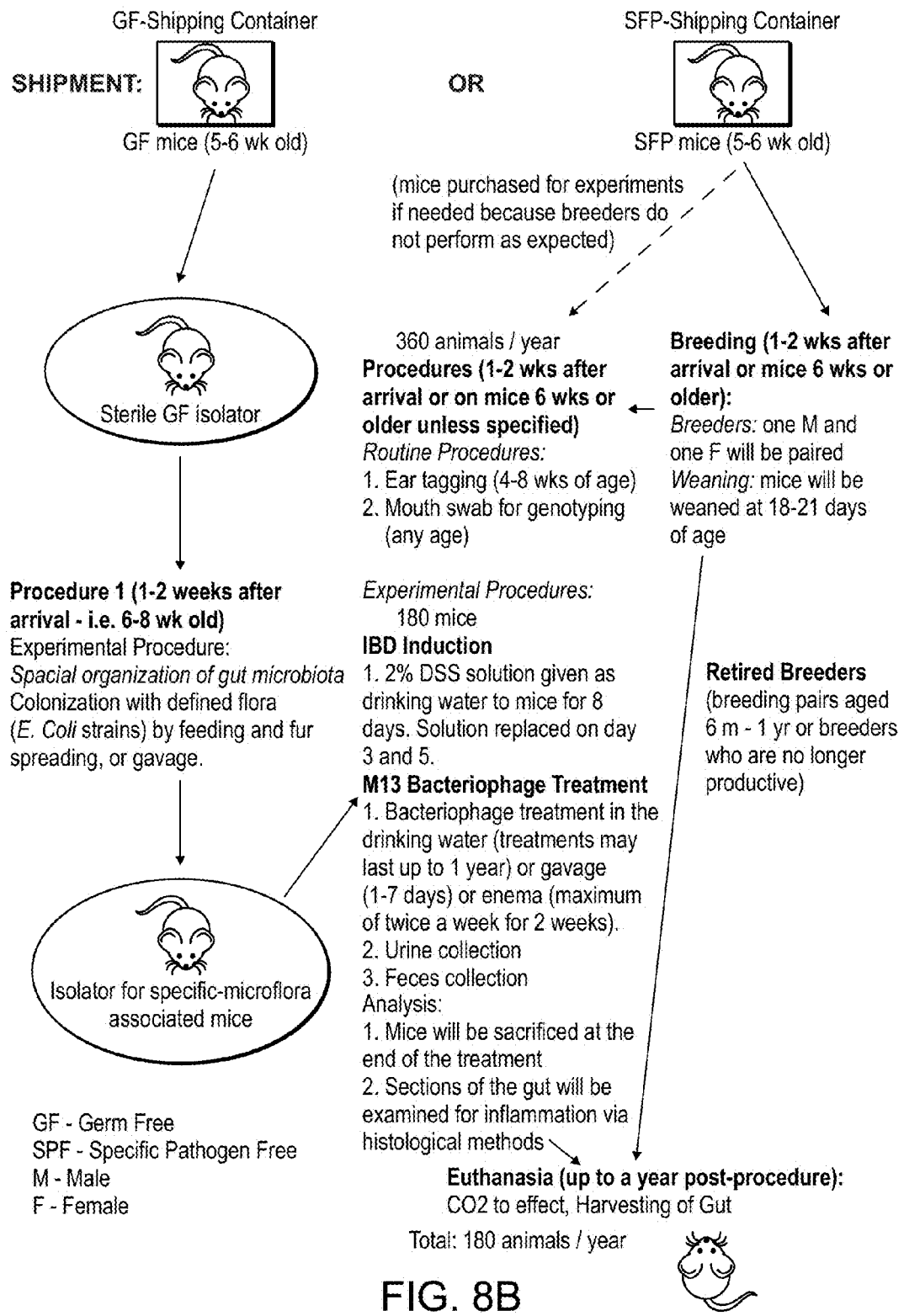
FIG. 8B depicts a general in vivo Inflammatory Bowel Disease model of the present disclosure.
Figure 9:
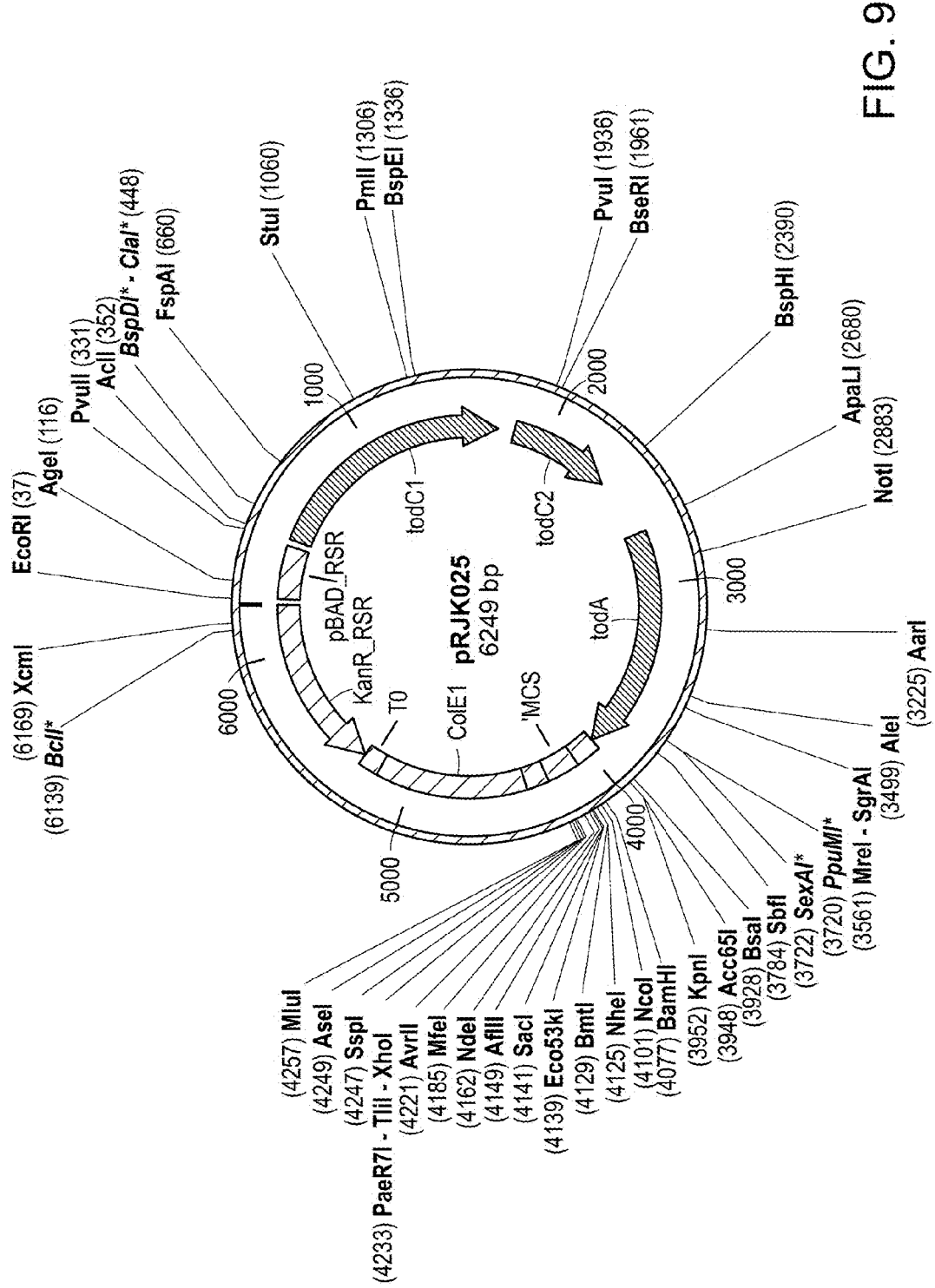
FIG. 9 depicts an inducible version of toluene dioxygenase on a test plasmid (pRJK025).
Figure 10:
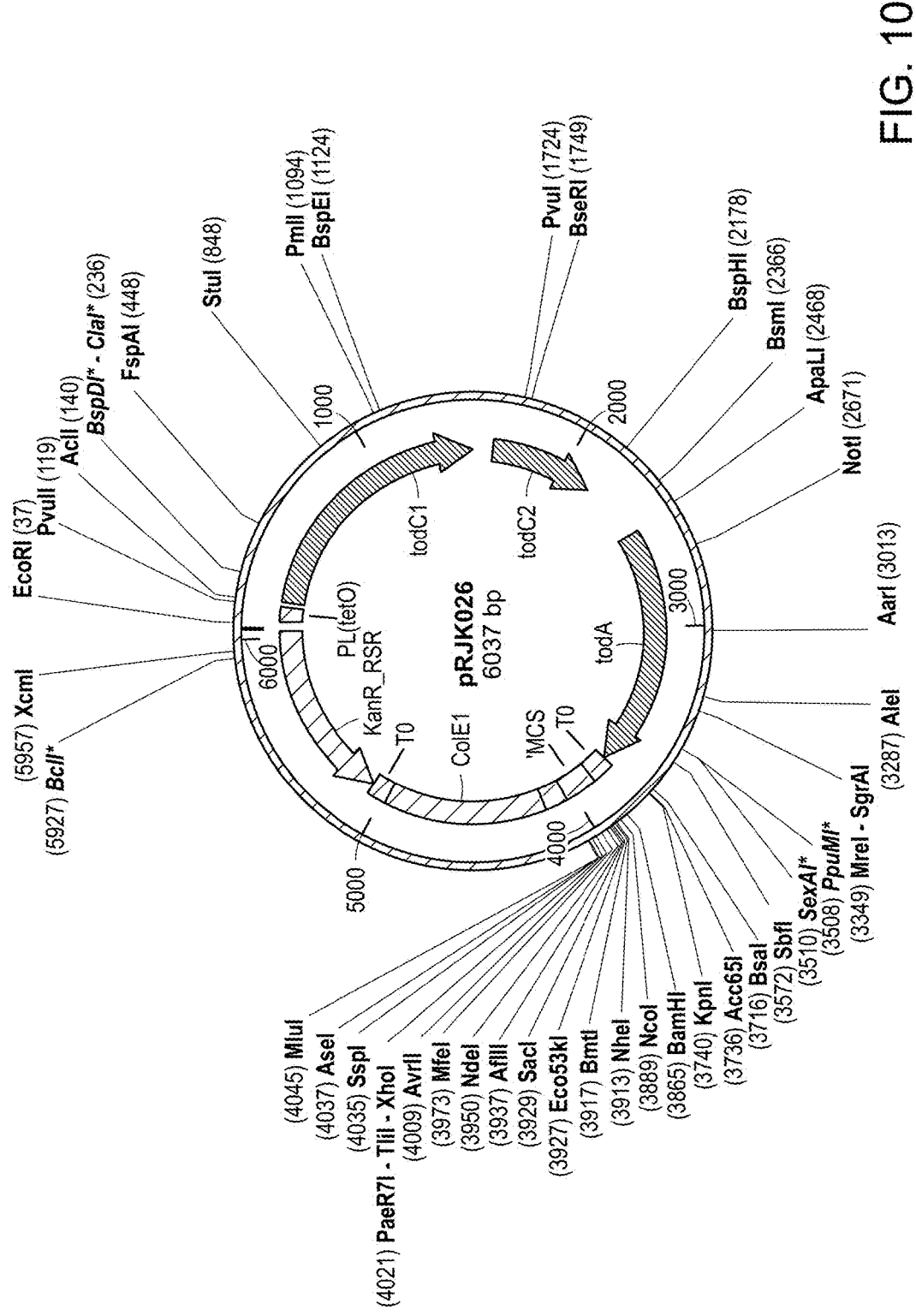
FIG. 10 depicts a constitutive version of toluene dioxygenase on a test plasmid (pRJK026).
Figure 11:
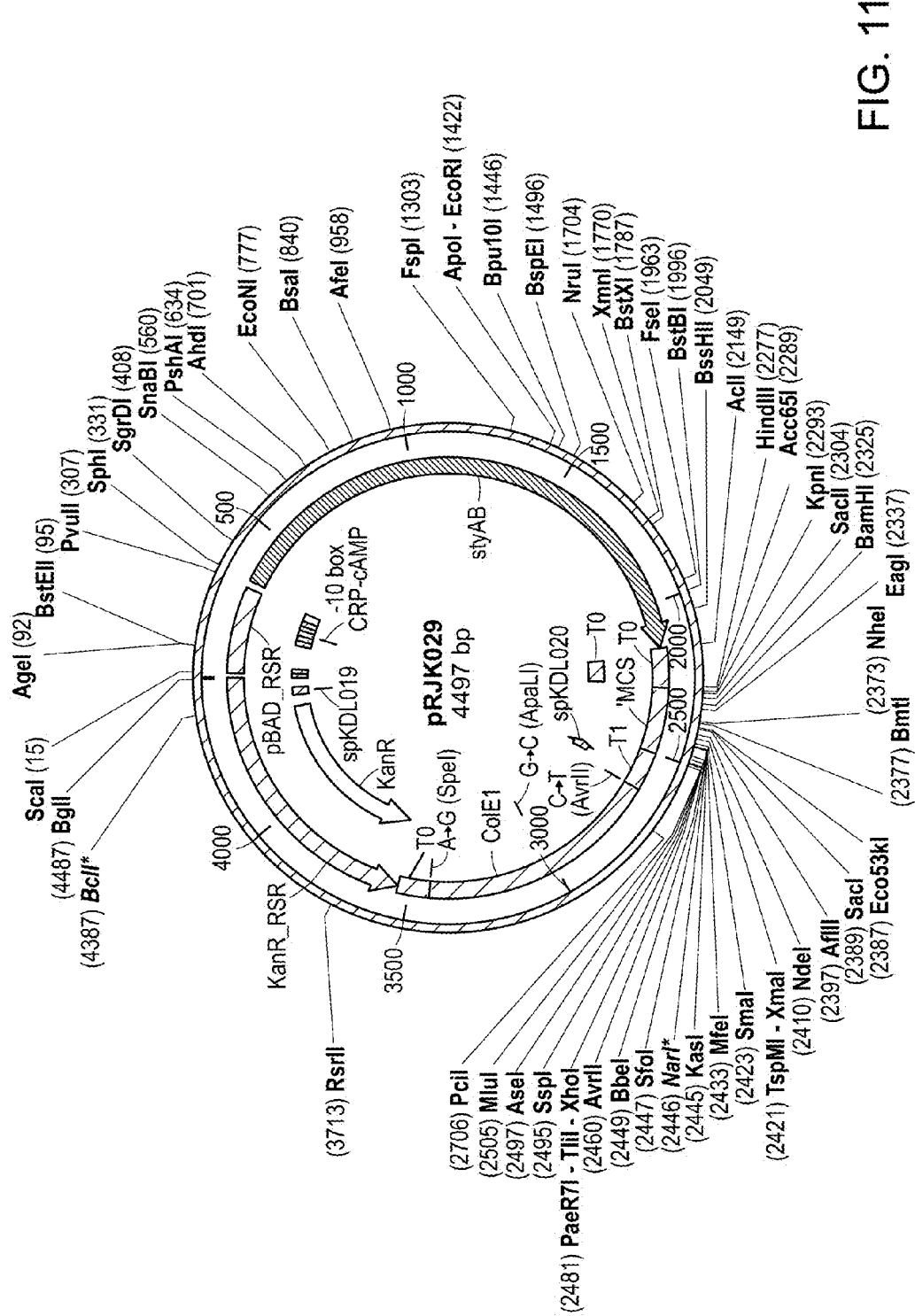
FIG. 11 depicts an inducible version of styrene monooxygenase on a test plasmid (pRJK029).
Figure 12:
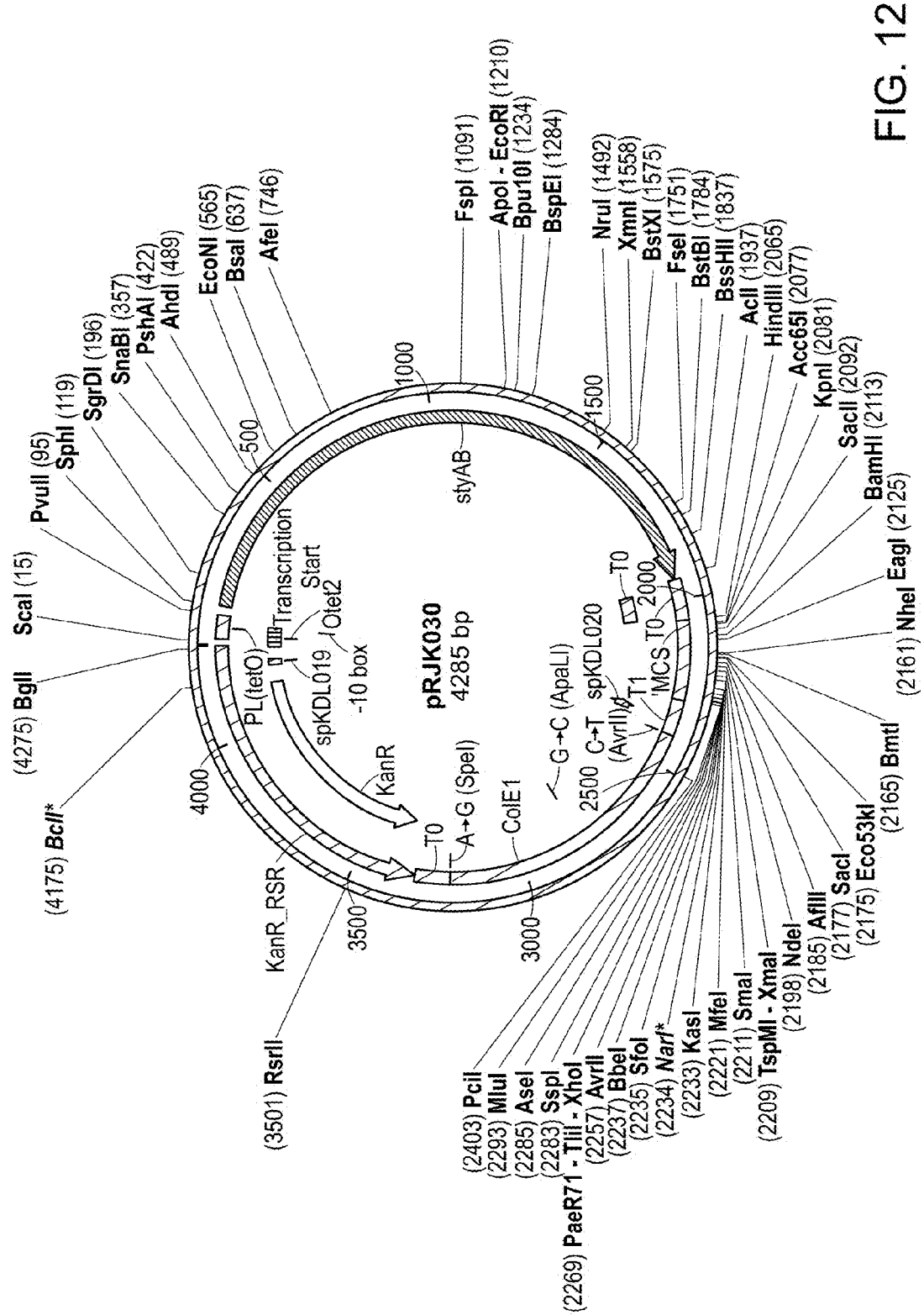
FIG. 12 depicts a constitutive version of styrene monooxygenase on a test plasmid (pRJK030).
Figure 13:
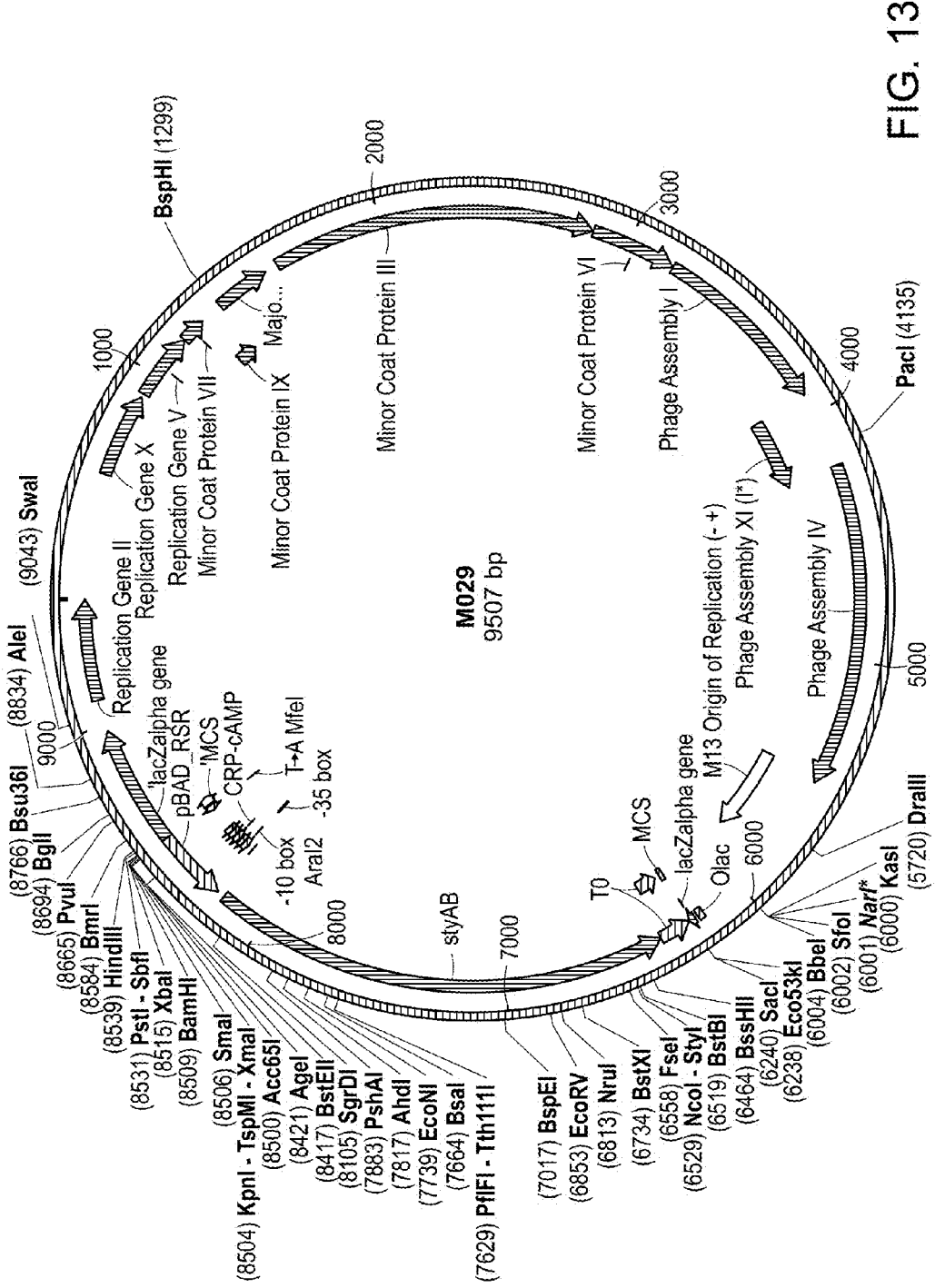
FIG. 13 depicts an inducible version of styrene monooxygenase on an M13 plasmid (M029).
Figure 14:
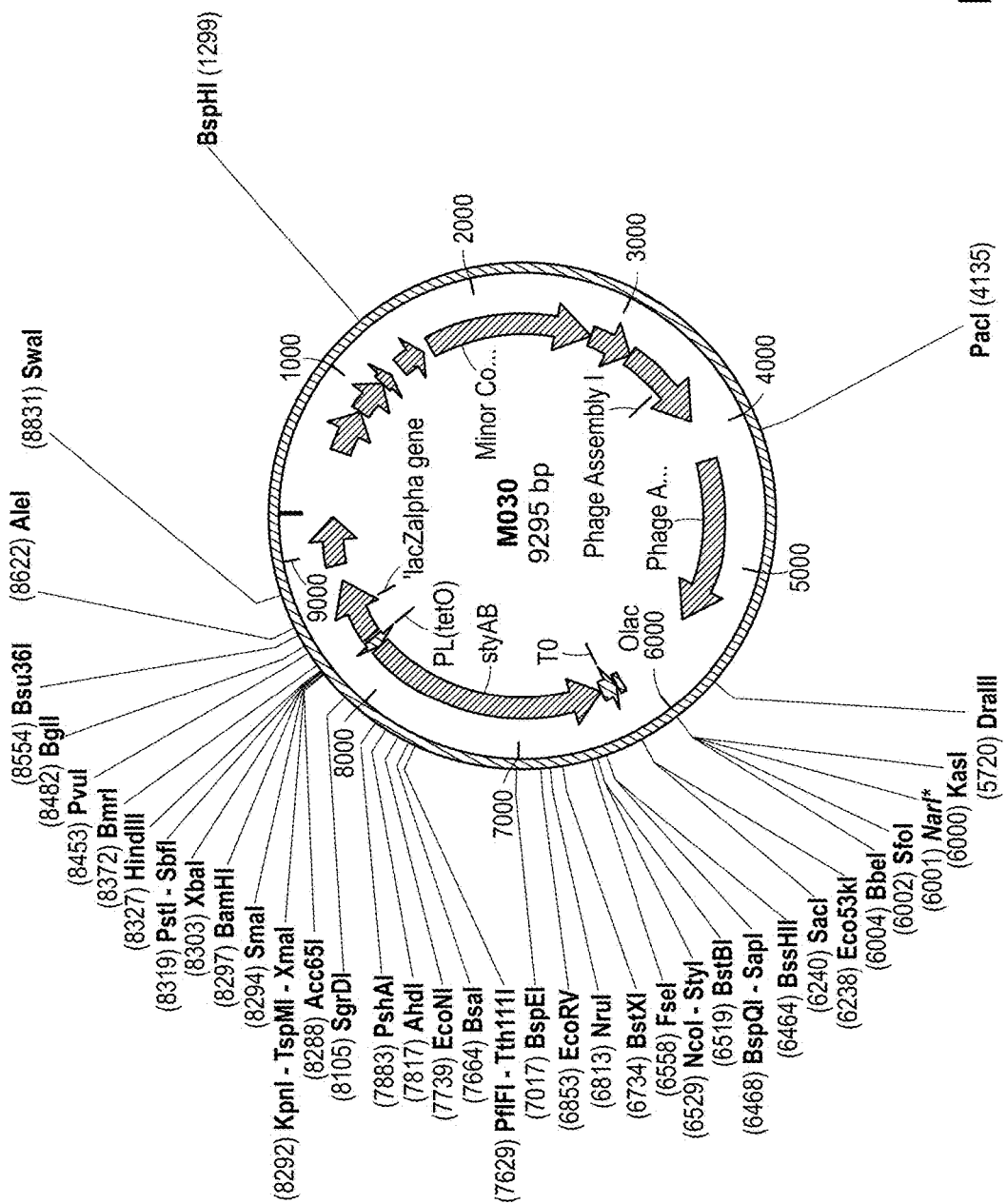
FIG. 14 depicts a constitutive version of styrene monooxygenase on an M13 plasmid (M030).

FIG. 7 shows a graph of indigo concentration as a function of the increasing doses of arabinose inducer (e.g., 1:400, 1:200, 1:100, 1:50, 1:25, 1:12.5).

Example 4

Inflammatory Bowel Disease (IBD) In Vivo Model

Mice are given 2% DSS solution in place of their regular drinking water for the course of 8 days. The mice receive approximately 5 ml of DSS solution per day and the solution is replaced on days 3 and 5. After 8 days of treatment, the DSS solution is replaced with regular drinking water or drinking water that contains the therapeutic bacteriophage particles for 7 days. This protocol provides a consistent model for the inflammatory reaction of inflammatory bowel disease (Pizarro et al. *Trends in Mol. Med.* 2003; Wirtz et al. *Nature Protocols.* 2007). An overview of the IBD model is shown in FIG. 5.

Example 5

Bacteriophage and Phagemid Networks In Vitro

Figure 15A:
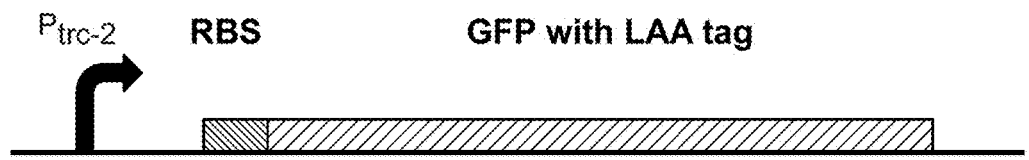
FIG. 15A depicts an example of a genetic circuit of the present disclosure, which includes a $P_{TRC-2}$ promoter operably linked to a ribosomal binding site and a nucleotide sequence encoding green fluorescent protein (GFP) with a LAA protein tag.
Figure 15B:
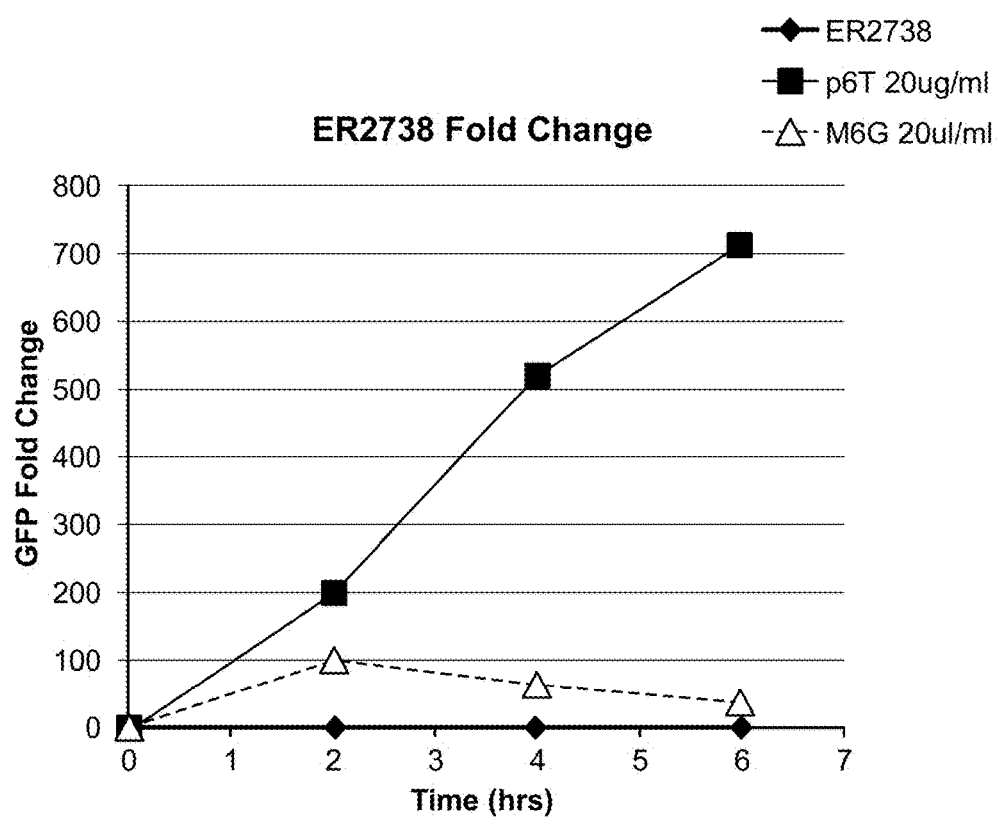
FIG. 15B depicts a graph showing the change in GFP fluorescence over time obtained from (1) ER2738 *Escherichia coli* (*E. coli*) cells transformed with a bacteriophage engineered to contain the genetic circuit depicted in FIG. 15A (referred to as a M6G bacteriophage), (2) ER2738 *E. coli* cells transformed with a phagemid engineered to contain the genetic circuit depicted in FIG. 15A (referred to as a p6T phagemid), and (3) ER2738 *E. coli* negative control cells (bacteria only).

*Escherichia coli* (*E. coli*) ER2738 bacterial cells were diluted 1:100 in media and grown for 90 minutes or until $OD_{600}$=0.2-0.3. Next, the bacterial cells were transduced with a 1:50 dilution of bacteriophage (designated M6G bacteriophage) or phagemid (designated p6T phagemid) stock. The bacteriophages and phagemids were engineered to comprise a genetic circuit that contains a nucleic acid with a constitutively active $P_{TRC-2}$ promoter operably linked to a nucleotide sequence encoding GFP (FIG. 15A). Bacterial cells without bacteriophages and phagemids served as a negative control. The bacterial cells were then incubated with shaking at 37° C., with fluorescence measurements being taken every 2 hours by flow cytometry. Results are shown in FIG. 15B. Notably, by 6 hours, there was a 700 fold increase in GFP expression in cells transfected with the phagemids, relative to the negative control.

Example 6

Bacteriophage and Phagemid Networks In Vivo

Figure 16:
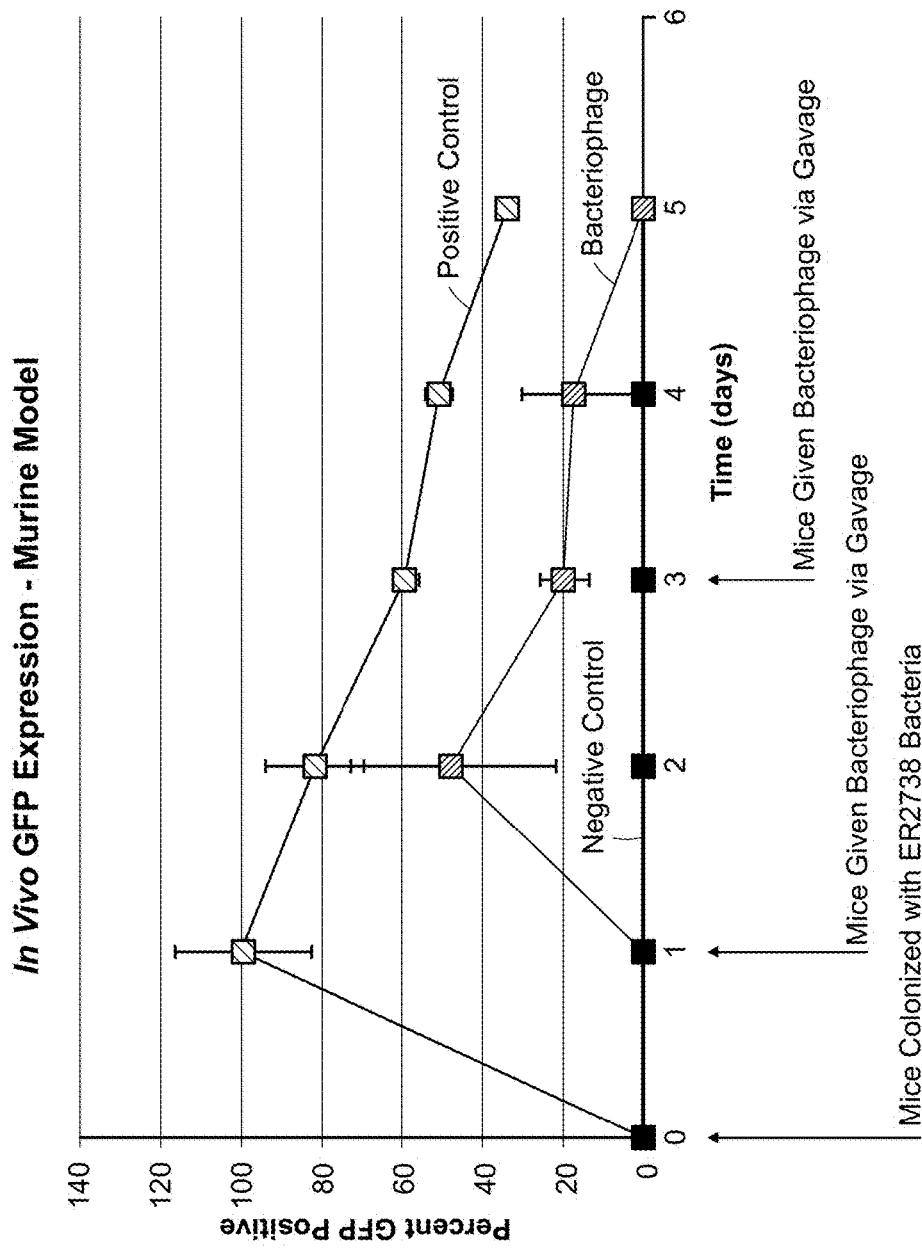
FIG. 16 depicts a graph showing the percentage of GFP positive cells in gnotobiotic mice colonized with (1) M6G bacteriophages, (2) ER2738 *E. coli* cells transformed with pLT006 plasmids containing the genetic circuit depicted in FIG. 15A (positive control), and (3) ER2738 *E. coli* negative control cells.

Gnotobiotic mice (a negative control group, a positive control group and a test group) were first colonized with ER2738 E. coli bacterial cells (e.g., by spreading the bacteria on the fur of the mice and by gavage). The ER2738 E. coli bacterial cells of the positive control group contained a pLT006 plasmid carrying the genetic circuit depicted in FIG. 15A. The test group was administered 200 µl of M6G bacteriophage containing carrying the genetic circuit depicted in FIG. 15A in SM buffer via gavage one day post-colonization and three days post-colonization. The positive control group and the negative control group were given 200 µl of SM buffer only (50 mM Tris-HCl (pH 7.5), 100 mM NaCl, 10 mM $MgSO_4$)) (blank control). The mice were fed water containing tetracycline to select for ER2738 E. coli bacterial cells (which are tetracycline resistant) for a total of 5 days. On days 0 to 5, fecal samples were collected from all mice and stored at −80° C. until ready for GFP characterization. Upon GFP characterization, fecal samples were dissolved in 1 ml of phosphate buffered saline (PBS), spun down for 3 minutes at 3.4 k rpm, and analyzed for GFP expression by FACS (1,000,000 events recorded; gate set up to distinguish GFP from $GFP^-$; "GFP Fluorescence geomean" and "% population $GFP^+$" values recorded). Percent $GFP^+$ data was used to track expression. All data scaled so that the peak GFP expression of the positive control registered as 100. This technique was used to reduce sample background. FIG. 16 shows that by day two post-colonization, 50% of the cells in the test group were positive for GFP, demonstrating successful in vivo delivery of bacteriophage engineered to contain a genetic circuit and expression of a molecule encoded by that circuit.

Methods
In Vitro Protocols
Phage Delivery
1. EMG2 or XL10 cells grown to stationary phase overnight.
2. Cultures washed 2× in M9 minimal media.
3. Cultures diluted 1:4 into experimental conditions.
4. Phage preps added 1:100 as well as any required inducers (e.g., 1:100 of 10% arabinose).
5. Cultures grown for 4 hours at 37° C. in shaking incubator.
6. Cultures read as needed on a fluorescence-activated cell sorting (FACS) or plate reader.
Indigo Production
1. Using the protocol described above.
2. After 4 hours of growth, indole added to a final concentration of 200-1000 µM (normal human physiological range).
3. Indole collected at desired time points as described and the concentration determined.
Indigo Collection
1. Indigo collected from culture by spinning sample at 15 k rpm for 2 min.
2. Supernatant removed.
3. DMSO added back to recover original volume amount.
4. Pellet resuspended and mixed.
5. Samples incubated at 70° C. for 10 min to ensure all indigo dissolves into solution.
6. Samples spun down again at 15 k for 2 min.
7. 300 µL of sample added to a 96 well plate and read on a plate reader at 610 nm for OD.
Cloning Methods
Standard cloning methods used, as described elsewhere herein.
In Vivo Protocols
Phage Delivery Protocol
Both wild-type and gnotobiotic mice colonized with E. coli are fed bacteriophage particles carrying synthetic networks in the drinking water. Bicarbonate may be given concordantly in order to ensure phage survival through the stomach. Phage or Test networks are induced by Arabinose or aTc in the drinking water as well. Treatments are administered to mice 6 weeks or older and may be given for up to one year.

The method mentioned above may be technically challenging as mice must consume the liquid containing the bacteriophages voluntarily. As an alternative method, the bacteriophage particles (and optionally, bicarbonate) are delivered directly to (e.g., inserted directly into) the stomach through gavage. Arabinose or aTc can also be introduced into the stomach by gavage.

An enema strategy may also be used. 6-9 week old mice are first anesthetized using continuous isoflurane inhalation or intraperitoneal injection of ketamine-zylasine. Using a sterile and lubricated small gavage needle and a 1 mL syringe, 50 µL of bacteriophage particles suspended in LB or M9 minimal media are slowly injected into the colon of anesthetized mice. Air bubbles are removed from the syringe prior to the procedure. The gavage needle is inserted only deep enough to ensure the liquid remains in the colon, then the needle is withdrawn. This procedure typically takes 2-5 minutes per mouse. The infected animal is then placed back inside its cage and monitored for any signs of distress. This procedure can be done a maximum of twice a week for a maximum of 2 weeks. Any mice showing signs of severe gastrointestinal distress are euthanized.

Feces and urine (if possible) are collected from the mice and tested for signs of phage infection. Sections of the gut are examined for signs of inflammation at the end of the experiment.

Mice are monitored at least twice per week for any signs of gastrointestinal or kidney distress from the bacteriophage treatment. Mice showing signs of severe distress (hunched posture, ruffled appearance, decreased activity, etc.) are euthanized by $CO_2$ inhalation to effect.

An overview of the general model is shown in FIG. 6.

SEQUENCES (pRJK025)

SEQ ID NO: 1

```
gacgtctgtgcaagtactactgttctgcagtcacttgaattcaagaaaccaatagtccatattgcatcagacattgccgtcactgcg
tcttttactggctcactcgctaaccaaaccggtaacccgcttattaaaagcattctgtaacaaagcgggaccaaagccatgaca
aaagcgcgtaacaaaagtgtctataatcacggcagaaaagtccacattgattatttgcacggcgtcacactttgctatgccatagc
attttatccataagattagcggatcatacctgacgcttttttatcgcaactctctactgtttctccatacagctgaaaagcttacgggag
gaacgttatgaatcagaccgacacatcacctatcaggctgcgcaggagctggaacaccagcgagatagaagcgctctttgacg
agcatgccggacgtatcgatccgcgcatttataccgatgaggatctgtaccaactcgaactggagcgtgtcttcgcccggtcctg
gctgctgttggggcatgaaacccagattcgcaagccgggcgattacatcacgacctacatgggtgaagaccctgtcgtggtcgt
ccggcagaaagacgccagcattgccgtgttcctgaaccagtgccgccaccgtggcatgcgcatctgccgcgcggatgccgg
aaacgcgaaggcgttcacttgcagctaccacgggtgggcttacgacaccgccggcaatcttgtcaatgtgccttacgaggccg
aatccttcgcgtgcctgaacaagaaggaatggagcccgctgaaggcccgggtagaaacctacaagggcctgattttcgccaac
tgggatgagaacgctgtagacctcgacacgtatctgggcgaggcgaagttctacatggaccacatgctcgaccgcaccgagg
ccggcaccgaagcgatcccgggcgtgcagaagtgggtcattccctgtaactggaaattgccgcagagcagttttgcagcgac
```

-continued

SEQUENCES

```
atgtaccatgccgggacgacctcgcatctgtctggcatcctggcaggcctgccagaagaccttgaaatggccgaccttgctccg
ccgacagttggcaagcagtaccgtgcgtcatggggcggacatggaagtggcttctatgtcggcgaccccaatctgatgcttgcc
atcatggggcaaaggtcaccagctactggaccgaaggccccgcgtcggaaaaggcggccgaacgtctgggtagcgtgga
gcgcggctcgaaactcatggtcgagcacatgaccgtcttccccacgtgttccttcctcccaggtatcaatacggtccggacatgg
catccgcgcgggccgaacgaggtcgaggtatgggcgtttacggtggtcgatgctgatgctcctgacgatatcaaggaagagtt
ccggcgccagacgctgcgcaccttctctgccggtggcgtgttcgagcaggacgacggggagaactgggtcgagatccagca
catcctgcgaggccacaaggcgcggagccgcccttcaatgccgagatgagcatggaccagaccgtcgacaacgacccggt
ttaccccgggcggatcagcaacaacgtctacagcgaggaagctgcccgcgggctctatgcccattggctgcggatgatgacat
cccccgactgggacgcgctgaaggcgacacgctgaatccagagacagcttgcgccacgcagtggcgccggccagaggcc
gcatttgacttcgacccaggttggatgcgtggaccttgtccatttgaaatctacaaggaacgaccatgattgattcagccaacag
agccgacgtctttctccgcaagccggcaccgtagccgccgaactgcagcacgaagtcgagcagttctactattgggaggcca
agcttctcaacgatcgccgcttcgaggagtggttcgcgctgctgcgcggaagacattcactacttcatgcccattcgcaccacgcg
gatcatgcgggactcgcgccttgaatactcaggctcccgagagtacgcgcacttcgatgacgacgccacgatgatgaaggga
cgcttgcgcaagatcacgtccgacgtgagctggtccgagaacccgcatcgcggacccggcatctcgtgagcaacgtgatga
tcgtcggcgcagaggcagaaggggagtacgaaatctcaagcgccttcattgtgtaccgcaatcgtctggagcggcagctcga
catctttgccggtgagcgtcgcgatacgttgcgccgtaacacgagcgaggccgggttcgagatcgtcaatcgaccatcctgat
cgaccagagcaccatcctggccaataacctcagtttcttcttctaggtgatgtcatgacttggacatacatattgcggcagggtga
cctgccaccggtgagatgcagcgctacgaaggcgggcccggaacctgtgatggtctgcaacgtcgatggcgagttcttcgcg
gtgcaggatacctgcacgcatggggactgggcgttgtcggatggttacctggacggtgatattgtcgaatgcacgttgcatttcg
gcaagttctgcgtgcggaccgggaaggtgaaggcgctgctgcctgcttgcaaacctatcaaggtattcccaatcaaggtcgaaggc
gatgaagtgcacgtcgatctcgacaacggggagttgaagtgatggctacccatgtggcgatcatccggcaatggcgtgggtggc
ttcacgaccgcgcaggcctacgtgccgagggcttcgaggggagaatctcgctgattggggacgaaccgcatctcccctatga
ccgaccatccttgtccaaggcggttctcgacggcagccttgagcggccgcccatactggccgaggccgattggtacggcgag
gcccgcatgacatgctgaccggcccggaagtcactgcccttgatgtgcagacaaggacgatcagtctggatgatggcacca
cgctctctgcggacgccatcgtcatcgcgacgggcagtcgagcgcggacgatggcgttgcccggcagccaactgccggtag
tcgtaacgctgcgcacctacggtgacgtgcaggtattgcgcgatagttggacttccgcgacgcggctgctgattgtgggtggcg
gattgatcggctgcgaggtcgcgacgacggcgcgcaagctcggcctgtcggtcacgatcctggaggcaggtgatgaactgct
ggtccgagtacttgggcggcgtatcggtgcctggctgcgcggccgtgctgacagaactggtggtgcaggtcgagttgggaacg
ggtgtcgtaggtttttctggtgagggccagctcgaacaagtcatggccagcgatgggcgagcttcgtagccgatagcgcactc
atttgcgtcggcgcggagcccgcggatcaacttgcgcgtcaagcgggcttggcatgtgaccgcggcgtcattgtcgatcactg
cggtgcgacgcttgccaaaggcgtattcgccgtcggagatgtggccagttggccgctgcgcgccggcggccggcgttcgctc
gaaacctatatgaacgcgcagcgccaagccgcgcggtggctgcggccattctgggggaaaaacgtatcggcaccgcaactg
cccgtgtcctggacggagatcgctgggcatcgatgcagatggcgggcgatatcgaaggaccttgttgattctgtctcgcgcgg
catgcccggtagtggcgctgccctgttgttccgcctgcaggagcgaaggattcaggcggtcgtcgcggtcgatgcaccccgtg
acttcgcgcttgcaacccgattggtagaagcccgcgcggcaatcgagccagcacggctggcagatctttcaaacagtatgcgc
gattttgttcgtgcgaatgaaggagacctaacgtgaggtaccccgagaattggcttggactcctgttgatagatccagtaatgacct
cagaactccatctggatttgttcagaacgctcggttgccgccgggcgtttttttattggtgagaatccaagcagtagtcaggatcctc
aagtcggccgcccgttccatggatactcgtcgaccattacgctagccgtctggactcggactgcttaagtcgctccatatgctc
gttcccgggactacacaattgtccccggcgccagggttgatatctatcgccctagggaccgtctcgagagaatcaatattaatc
caacgcgtggcatcaaataaaacgaaaggctcagtcgaaagactgggcctttcgtttttatctgttgtttgtcggtgaacgctctcct
gagtaggacaaatccgccgcctagacttaggcgttcggctgcggcggtgatcagctcactcaaaggcggtaatacggtt
atccacagaatcaggggataacgcaggaaagaacatgtgagcaaaaggccagcaaaaggccaggaaccgtaaaaaggccg
cgttgctggcgtttttccataggctccgcccccctgacgagcatcacaaaaatcgacgctcaagtcagaggtggcgaaaccga
caggactataaagataccaggcgtttccccctggaagctccctcgtgcgctctcctgttccgaccctgccgcttaccggatacct
gtccgccttctcccttcgggaagcgtggcgctttctcatagctcacgctgtaggtatctcagttcggtgtaggtcgttcgctccaa
gctgggctgtctgcacgaaccccccgttcagcccgaccgctgcgccttatccggtaactatcgtcttgagtccaacccggtaag
acacgacttatcgccactggcagcagccactggtaacaggattagcagagcgaggtatgtaggcggtgctacagagttcttga
agtggtggcctaactacggctacactagaaggacagtatttggtatctgcgctctgctgaagccagttaccttcggaaaaagagtt
ggtagctcttgatccggcaaacaaaccaccgctggtagcggtggtttttttgttgcaagcagcagattacgcgcagaaaaaaag
gatctcaagaagatcctttgatcttttctacggggtctgacgctcagtggaacgaaaactcacgttaagggattttggtcatggcta
gtgcttggattctcaccaataaaaaacgcccggcggcaaccgagcgttctgaacaaatccagatggagttctgaggtcattactg
gatctatcaacaggagtccaagccaattctcgaaccccagagtcccgctcagaagaactcgtcaagaaggcgatagaaggcg
atgcgctgcgaatcgggagcgggcggataccgtaaagcacgaggaagcggtcagcccattcgccgccaagctcttcagcaatat
cacgggtagccaacgctatgtcctgatagcggtccgccacacccagccggccacagtcgatgaatccagaaaagcggccatt
ttccaccatgatattcggcaagcaggcatcgccgtgggtcacgacgagatcctcgccgtcgggcatacgcgccttgagcctgg
cgaacagttcggctggcgcgagcccctgatgctcttcgtccagatcatcctgatcgacaagaccggcttccatccgagtacgtg
ctcgctcgatgcgatgtttcgcttggtggtcgaatgggcaggtagccggatcaagcgtatgcagccgccgcattgcatcagcca
tgatggatactttctcggcaggagcaaggtgagatgacaggagatcctgccccggcacttcgcccaatagcagccagtccctt
ccgcttcagtgacaacgtcgagcacagcgcgcaaggaacgcccgtcgtggccagccacgatagccgcgctgcctcgtcttg
cagttcattcagggcaccggacaggtcggtcttgacaaaaagaaccgggcgaccctgcgctgacagccggaacacgcggc
atcagagcagccgattgtctgttgtgcccagtcatagccgaatagcctctccacccaagcgccggagaacctgcgtgcaatcc
atcttgttcaatcatgcgaaacgatcctcatcctgtctcttgatcagatcttgatccctgcgccatcagatccttggcggcaagaaaa
gccatccagtttactttgcagggcttcccaaccttaccagagggcgggcccaactggcaattcc
```

(pRJK026)

SEQ ID NO: 2

```
gacgtctgtgcaagtactactgttctgcagtcacttgaattctccctatcagtgatagagattgacatccctatcagtgatagagata
ctgagcacatcagcaggacgcactgacccagctgaaaagcttacgggaggaacgttatgaatcagaccgacacatcacctatc
aggctgcgcaggagctggaacaccagcgagatagaagcgctctttgacgagcatgccggacgtatcgatccgcgcatttatac
cgatgaggatctgtaccaactcgaactggagcgtgtcttcgcccggtcctggctgctgttggggcatgaaacccagattcgcaa
gccgggcgattacatcacgacctacatgggtgaagaccctgtcgtggtcgtccggcagaaagacgccagcattgccgtgttcc
tgaaccagtgccgccaccgtggcatgcgcatctgccgcgcggatcgccgcaggtgccggaaacgcgaaggcgttcacttgcagctaccacg
ggtgggcttacgacaccgccgcaatcttgtcaatgcgcttacgaggccgaatccttcgcgtgcctgaacaagaaggaatgg
agcccgctgaaggcccgggtagaaacctacaaggcgctgattttcgccaactgggatgagaacgctgtagacctcgacacgt
atctgggcgaggcgaagttctacatggaccacatgctcgaccgcaccgaggccggcaccgaagcgatcccgggcgtgcaga
agtgggtcattccctgtaactggaaattcgccgcagagcagttttgcagcgacatgtaccatgccgggacgacctcgcatctgtc
tggcatcctggcaggcctgccagaagaccttgaaatggccgaccttgctccgccgacagttggcaagcagtaccgtgcgtcat
```

SEQUENCES ggggcggacatggaagtggcttctatgtcggcgaccccaatctgatgcttgccatcatggggccaaaggtcaccagctactgg
accgaaggccccgcgtcggaaaaggcggccgaacgtctgggtagcgtggagcgcggctcgaaactcatggtcgagcacat
gaccgtcttccccacgtgttccttcctcccaggtatcaatacggtcggacatggcatccgcgcgggccgaacgaggtcgaggt
atgggcgtttacggtggtcgatgctgatgctcctgacgatatcaaggaagagttccggcgccagacgctgcgcaccttctctgc
cggtggcgtgttcgagcaggacgacggggagaactgggtcgagatccagcacatcctgcgaggccacaaggcgcggagcc
gcccttcaatgccgagatgagcatggaccagaccgtcgacaacgacccggtttaccccgggcggatcagcaacaacgtcta
cagcgaggaagctgcccgcgggctctatgcccattggctgcggatgatgacatccccgactgggacgcgctgaaggcgac
acgctgaatccagagacagcttgcgccacgcagtggcgccggccagaggccgcatttgacttcgacccaggttggatgcggt
ggaccttgtccatttgaaatctacaaggaacgaccatgattgattcagccaacagagccgacgtctttctccgcaagccggcacc
cgtagcgcccgaactgcagcacgaagtcgagcagttctactattgggaggccaagcttctcaacgatcgccgcttcgaggagt
ggttcgcgctgctcgcggaagacattcactacttcatgcccattcgcaccacgcggatcatgcgggactcgcgccttgaatactc
aggctcccgagagtacgcgcacttcgatgacgacgccacgatgatgaaggacgcttgcgaagatcacgtccgacgtgag
ctggtccgagaaccccgcatcgcggacccggcatctcgtgagcaacgtgatgatcgtcggcgcagaggcagaagggagta
cgaaatctcaagcgccttcattgtgtaccgcaatcgtctggagcggcagctcgacatctttgccggtgagcgtcgcgatacgttg
cgccgtaacacgagcgaggccgggtcgagatcgtcaatcggaccatcctgatcgaccagagcaccatcctggccaataacc
tcagtttcttcttctaggtgatgtcatgacttggacatacatattgcggcagggtgacctgccaccccggtgagatgcagcgctacg
aaggcggcccgaacctgtgatggtctgcaacgtcgatggcgagttcttcgcggtgcaggatacctgcacgcatggggactg
ggcgttgtcggatggttacctggacggtgatattgtcgaatgcacgttgcatttcggcaagtctgcgtgcggaccgggaaggtg
aaggcgctgcctgcttgcaaacctatcaaggtattcccaatcaaggtcgaaggcgatgaagtgcacgtcgatctcgacaacgg
ggagttgaagtgatggctacccatgtgcgatcatcggcaatggcgtgggtggcttcacgaccgcgcaggccctacgtgccg
agggcttcgaggggagaatctcgctgattgggacgaaccgcatctcccctatgaccgaccatccttgtccaaggcggttctcg
acggcagccttgagcggccgcccatactggccgaggccgattggtacggcgaggcccgcatcgacatgctgaccggcccg
gaagtcactgcccttgatgtgcagacaaggacgatcagtctggatgatggcaccacgctctctgcggacgccatcgtcatcgcg
acgggcagtcgagcgcgacgatggcgttgcccggcgacccaactgctgcagtcgggggtcgtaacgctgcgcacctacggtgacgt
gcaggtattgcgcgatagttggactttccgcgacgcggctgctgattgtgggtggcggattgatcggctgcgaggtcgcgacga
cggcgcgcaagctcggcctgtcggtcacgatcctggaggcaggtgatgaactgctggtccgagtacttgggcggcgtatcgg
tgcctggctgcgcggcctgctgacagaacttggtgtgcaggtcgagttgggaacgggtgtcgtaggttttctggtgagggcca
gctcgaacaagtcatggccagcgatgggcgcagcttcgtagccgactgcactcattttgcgtcggcgggcggagcccgcggat
caacttgcgcgtcaagcgggcttggcatgtgaccgcggcgtcattgtcgatcactgcggtgcgacgcttgccaaaggcgtattc
gccgtcggagatgtggccagttggccgctgcgcgccggcggccggcgttcgctcgaaacctatatgaacgcgcagcgccaa
gccgccgcggtggctgcggccattctggggaaaaacgtatcggcaccgcaactgcccgtgtcctggacggagatcgctggg
catcgcatgcagatggcgggcgatatcgaaggacctggtgatttcgtctcgcgcggcatgcccggtagtggcgctgccctgtt
gttccgcctgcaggagcgaaggattcaggcggtcgtcgcggtcgatgcacccccgtgacttcgcgcttcgcaacccgattggtag
aagcccgcgcggcaatcgagccagcacggctggcagatctttcaaacagtatgcgcgattttgttcgtgcgaatgaaggagac
ctaacgtgaggtacccgagaattggcttggactcctgttgatagatccagtaatgacctcagaactccatctggatttgttcagaac
gctcggttgccgccgggcgttttttattggtgagaatccaagcagtagtcaggatcctcaagtcggccgcccgttccatggatact
cgtcgaccattacgctagccgtctggagctcggactgcttaagtcgctccatatgctcgttcccgggactacacaattgtcccccg
gcgccagggttgatatctatcgccctagggaccgtctcgagagaatcaatattaatccaacgcgtggcatcaaataaaacgaaa
ggctcagtcgaaagactgggcctttcgttttatctgttgtttgtcggtgaacgctctcctgagtaggacaaatccgccgcctagac
ttaggcgttcggctgcggcgagcggtatcagctcactcaaaggcggtaatacggttatccacagaatcagggggataacgcagg
aaagaacatgtgagcaaaaggccagcaaaaggccaggaaccgtaaaaaggccgcttgctggcgtttttccataggctccgc
ccccctgacgagcatcacaaaaatcgacgctcaagtcagaggtggcgaaacccgacaggactataaagataccaggcgttc
ccctggaagctccctcgtgcgctctcctgttccgaccctgccgcttaccggatacctgtccgcctttctcccttcgggaagcgtg
gcgctttctcatagctcacgctgtaggtatctcagttcggtgtaggtcgttcgctccaagctgggctgtctgcacgaaccccccgtt
cagcccgaccgctgcgccttatccggtaactatcgtcttgagtccaaacccggtaagacacgacttatcgccactggcagcagcc
actggtaacaggattagcagagcgaggtatgtaggcggtgctacagagttcttgaagtggtggcctaactacggctacactaga
aggacagtatttggtatctgcgctctgctgaagccagttaccttcggaaaaagagttggtagctcttgatccggcaaacaaacca
ccgctggtagcggtggtttttttgtttgcaagcagcagattacgcgcagaaaaaaaggatctcaagaagatcctttgatcttttctac
ggggtctgacgctcagtggaacgaaaactcacgttaagggattttggtcatgactagtgcttggattctcaccaataaaaaacgc
ccggcggcaaccgagcgttctgaacaaatccagatggagttctgaggtcattactggatctatcaacaggagtccaagccaatt
ctcgaacccagagtcccgctcagaagaactcgtcaagaaggcgatagaaggcgatgcgctgcgaatcgggagcggcgata
ccgtaaagcacgaggaagcggtcagcccattcgccgccaagctcttcagcaatatcacgggtagccaacgctatgtcctgata
gcggtccgccacacccagccggccacagtcgatgaatccagaaaagcggccattttccaccatgatattcggcaagcaggcat
cgccatgggtcacgacgagatcctcgccgtcgggcatacgcgccttgagcctggcgaacagttcggctggcgcgagcccct
gatgctcttcgtccagatcatcctgatcgacaagaccggcttccatccgagtacgtgctcgctcgatgcgatgtttcgcttggtggt
cgaatgggcaggtagccggatcaagcgtatgcagccgccgcattgcatcagccatgatggatactttctcggcaggagcaag
gtgagatgacaggagatcctgccccggcacttcgcccaatagcagccagtccttcccgcttcagtgacaacgtcgagcacag
ccgcgcaaggaacgcccgtcgtggccagccacgatagccgcgctgcctcgtcttgcagttcattcagggcaccggacaggtc
ggtcttgacaaaaagaaccgggcgaccctgcgctgacagccggaacacggcggcatcagagcagccgattgtctgttgtgcc
cagtcatagccgaatagcctctccacccaagcggccggagaacctgcgtgcaatccatcttgttcaatcatgcgaaacgatcctc
atcctgtctcttgatcagatcttgatccctgcgccatcagatccttggcggcaagaaagccatccagtttactttgcagggcttcc
caaccttaccagagggcggcccaactggcaattcc (pRJK029)

SEQ ID NO: 3 gacgtctgtgcaagtactaagaaaccaatagtccatattgcatcagacattgccgtcactgcgtcttttactggctcttctcgctaac
caaaccggtaaccccgcttattaaaagcattctgtaacaaagcgggaccaaagccatgacaaaagcgcgtaacaaaagtgtct
ataatcacggcagaaaagtccacattgattatttgcacggcgtcacactttgctatgccatagcatttttatccataagattagcgga
tcataccctgacgcttttttatcgcaactctctactgtttctccatacagctgaaggattaaggaggtagcatgcatgaaaaagcgtatc
ggtattgttggtgcaggcactgccggcctccatcttggcctcttcctccgccagcatgacgtcgacgtcactgtgtacactgatcg
taagcccgatgagtacagtggactgcggctcctgaataccgttgctcacacgcggtgacggtgcagcgggaggttgccctcg
acgtcaatgagtggcgtctgagggagtttggctgtatttcggccactactacgtaggtgggccgcagcccatgcgtttctacggt
gatctcaaggctcccagccgtgcagtggactaccgtctctacctgccgatgctgatgcgtgcactggaagcaggggcggcaa
gttctgctacgacgccgtgtctgccgaagatctgaagggctgtcggagcagtatgatctgctggttgtgtgcactggtaaatac
gccctcggcaaggtgttcgagaagcagtccgaaaactcgcccttcgagaagccgaacgggcactgtgcgttggtctcttcaa
gggcatcaaggaagcaccgattcgcgcggtgactatgtccttctcgccagggcatggcgagctgattgagattccaaccctgtc
gttcaatggcatgagcacagcgctggtgctcgaaaaccatattggtagcgatctggaagtcctcgcccacaccaagtatgacga -continued

SEQUENCES tgacccgcgtgcgttcctcgatctgatgctggagaagctgcgtaagcatcatccttccgttgccgagcgcatcgatccggctgag
ttcgacctggccaacagttctctggacatcctccagggcggtgttgtgccagtattccgcgacggtcatgcgaccctcaataacg
gcaaaaccatcatcgggctgggcgacatccaggcaactgtcgatccggtcttgggccagggcgcgaacatggcgtcctatgc
ggcatggattctgggcgaggaaatccttgcgcactctgtctacgacctgcgcttcagcgaacacctggagcgtcgccgccagg
atcgcgtgctgtgcgccacccgctggaccaacttcactctgagcgccttcacggaacttccgccggaattcctcaccttccttca
gatcctgagccagagccgtgaaatggctgatgagttcacggacaacttcaactatccggaacttcagtgggatcgcttctccagc
ccggaacgtatcggtcagtggtgcagccagtacgcaccccactattgcggcctgacgctattgctccgctggtcaaggccagcg
gagccctaacctctgggtgattcaaatgacgttaaaaaaagatgtggtggtggatatcgactccaccagcttccgccaggcggtt
gcactgttcgcgacgggaattgcggttctcagcgcggagactgacgagggcgaagtgcatggcatgacggtgaacagcttca
cctccatcagtctggacccgccgactgtgatggtgtccctgaagtcgggccgtatgcatgagctgctgactcaaggcggacgct
tcggcgtcagcctcctgggtgaaagtcagaagatgttatcggcattcttcagcaagcgtgtgatcgatggcactcctcctcctgct
ttcacagttcaggccggcctccccactctgcgggacgcgttaatggcctggttcgaatcggccgacgttctgacggagcacggttgaagtaca
cgaccacacgctcttcattgcgcgcgttagcgcctgtggagtgccggaggcgaatgccccccagccgctgctgttctttgccag
ccgttatcacggcaacccgttgccgctgaattgaaacgttcgagaattggcttggactcctgttgatagatccagtaatgacctca
gaactccatctggatttgttcagaacgctcggttgccgcgggcgtttttattggtgagaatccaagcagtagtcaaagcttccgc
aaggtaccacttttgccgcggagtatttgtacatttgaaggatcctcaagtcggccgcccgttccatggatactcgtcgaccattac
gctagccgtctggagctcggactgcttaagtcgctccatatgctcgttcccgggactacacaattgtccccggcgccagggttg
atatctatcgccctagggaccgtctcgagagaatcaatattaatccaacgcgtggcatcaaataaaacgaaaggctcagtcgaa
agactgggccttcgttttatctgttgtttgtcggtgaacgctctcctgagtaggacaaatccgccgccctagacttaggcgttcgg
ctgcggcgagcggtatcagctcactcaaaggcggtaatacggttatccacagaatcagggaataacgcaggaaagaacatgt
gagcaaaaggccagcaaaaggccaggaaccgtaaaaaggccgcgttgctggcgtttttccataggctccgcccccctgacga
gcatcacaaaaatcgacgctcaagtcagaggtggcgaaacccgacaggactataaagataccaggcgtttccccctggaagct
ccctcgtgcgctctcctgttccgaccctgccgcttaccggatacctgtccgcctttctcccttcgggaagcgtggcgctttctcata
gctcacgctgtaggtatctcagttcggtgtaggtcgttcgctccaagctgggctgtgcacgaacccccgttcagcccgaccg
ctgccgcttatccggtaactatcgtcttgagtccaacccggtaagacacgacttatcgccactggcagcagccactggtaacag
gattagcagagcgaggtatgtaggcggtgctacagagttcttgaagtggtggcctaactacggctacactagaaggacagtattt
ggtatctgcgctctgctgaagccagttaccttcggaaaaagagttggtagctcttgatccggcaaacaaaccaccgctggtagc
ggtggtttttttgtttgcaagcagcagattacgcgcagaaaaaaaggatctcaagaagatcctttgatcttttctacggggtctgac
gctcagtggaacgaaaactcacgttaaggggattttggtcatggctagtgcttggattctcaccaataaaaaacgcccgcggcaa
ccgagcgttctgaacaaatccagatggagttctgaggtcattactggatctatcaacaggagtccaagccaattctcgaacccca
gagtcccgctcagaagaactcgtcaagaaggcgatagaaggcgatgcgctgcgaatcgggagcggcgataccgtaaagcac
gaggaagcggtcagcccattcgccgccaagctcttcagcaatatcacgggtagccaagctatgtcctgatagcggtccgcca
cacccagccggccacagtcgatgaatccagaaaagcggccatttttccaccatgatattcggcaagcaggcatcgccatgggtc
acgacgagatcctcgccgtcgggcatacgcgccttgagcctggcgaacagttcggctggcgcgagcccctgatgctcttcgtc
cagatcatcctgatcgacaagaccggcttccatccgagtacgtgctcgctcgatgcgatgtttcgcttggtggtcgaatgggcag
gtagccggatcaagcgtatgcagccgccgcattgcatcagccatgatggatactttctcggcaggagcaaggtgagatgacag
gagatcctgccccggcacttcgcccaatagcagccagtccctttcccgcttcagtgacaacgtcgagcacagcgcgcaagga
acgcccgtcgtggccagcacgatagccgcgctgcctcgtcttgcagttcattcagggcaccggacaggtcggtcttgacaaa
aagaaccgggcgaccctgcgctgacagccggaacacggcggcatcagagcagccgattgtctgttgtgcccagtcatagcc
gaatagcctctccacccaagccgccggagaacctgcgtgcaatccatcttgttcaatcatgcgaaacgatcctcatcctgtctctt
gatcagatcttgatccctgcgccatcagatccttggcggcaagaaagccatccagtttactttgcagggcttcccaaccttacca
gagggcgccccaactggcaattcc (pRJK030)

SEQ ID NO: 4 gacgtctgtgcaagtacttccctatcagtgatagagattgacatccctatcagtgatagagatactgagcacatcagcaggacgc
actgaccccagctgaaggattaaggaggtagcatgcatgaaaaagcgtatcggtattgttggtgcaggcactgccggcctccatc
ttggcctcttcctccgccagcatgacgtcgacgtcactgtgtacactgatcgtaagcccgatgagtacagtggactgcggctcct
gaataccgttgctcacaacgcggtgacggtgcaggaggttgcctcgacgtcaatgagtggccgtctgaggagtttggct
atttcggccactactactacgtaggtgggccgcagcccatgcgtttctacggtgatctcaaggctcccagccgtgcagtggacta
ccgtctctacctgccgatgctgatgcgtgcactggaagccaggggcggcaagttctgctacgacgccgtgtctgccgaagatct
ggaagggctgtcggagcagtatgatctgctggagtgtgcactggtaaatacgccctcggcaaggtgacgagaagcagtccg
aaaactcgcccttcgagaagccgcaacgggcactgtgcgttggtctctcaagggcatcaaggaagcaccgattcgcgcggtg
actatgtccactcgccaggcatggcgagctgattgagattccaaccctgtcgttcaatggcatgagcacagcgctggtgctcg
aaaaccatattggtagcgatctggaagtcctcgcccacaccaagtatgacgatgacccgcgtgcgacctcgatctgatgctgga
gaagctgcgtaagcatcatccaccgagccgagcgcatcgatccggctgagttcgacctggccaacagactctggacatcctc
cagggcggtgagtgcagtattccgcgacggtcatgcgaccctcaataacggcaaaaccatcatcgggctgggcgacatcca
ggcaactgtcgatccggtcagggcagggcgaacatggcgtcctatgcggcatggattctgggcgaggaaatccttgcgc
actctgtctacgacctgcgcttcagcgaacacctggagcgtcgccgccaggatcgcgtgctgtgcgccacccgctggaccaac
ttcactctgagcgcatcacggaacttccgccggaattcctcaccaccacagatcctgagccagagccgtgaaatggctgatga
gttcacggacaacttcaactatccggaacttcagtgggatcgatctccagcccggaacgtatcggtcagtggtgcagccagtac
gcacccactattgcggcctgacgctattgctccgctggtcaaggccagcggagccctaacctctgggtgattcaaatgacgttaa
aaaaagatgtggtggtggatatcgactccaccagcaccgccaggcggagcactgacgcgacgggaattgcggactcagcg
cggagactgacgagggcgaagtgcatggcatgacggtgaacagcttcacctccatcagtctggacccgccgactgtgatggt
gtccctgaagtcgggccgtatgcatgagctgctgactcaaggcggacgcttcggcgtcagcctcctgggtgaaagtcagaaga
tgttatcggcattcttcagcaagcgtgtgatcgatggcactcctcctcctgcatcacagttcaggccggcctccccactctgcggg
acgccatggcctggacgaatgcgaggtggacaggagatacacgaccacacgctcttcattgcgcgcgttagcgcc
tgtggagtgccggaggcgaatgccccccagccgctgctgactagccagccgttatcacggcaacccgttgccgctgaattga
aacgttcgagaattggcaggactcctgagatagatccagtaatgacctcagaactccatctggatttgacagaacgctcggag
ccgcgggcgttattattggtgagaatccaagcagtagtcaaagatccgcaaggtaccactagccgcggagtatagtacattt
gaaggatcctcaagtcggccgcccgaccatggatactcgtcgaccattacgctagccgtctggagctcggactgcttaagtcg
ctccatatgctcgacccgggactacacaattgtcccccggcgccagggttgatatctatcgccctagggaccgtctcgagagaa
tcaatattaatccaacgcgtggcatcaaataaaacgaaaggctcagtcgaaagactgggccatcgattatctgagtagtcggtg
aacgctctcctgagtaggacaaatccgccgccctagacttaggcgttcggctgcggcgagcggtatcagctcactcaaaggcg
gtaatacggttatccacagaatcagggataacgcaggaaagaacatgtgagcaaaaggccagcaaaaggccaggaaccgt
aaaaaggccgcgagctggcgtattccataggctccgcccccctgacgagcatcacaaaaatcgacgctcaagtcagaggtg
gcgaaacccgacaggactataaagataccaggcgtttccccctggaagctccctcgtgcgctctcctgttccgaccctgccgctt -continued

SEQUENCES accggatacctgtccgcctactccatcgggaagcgtggcgattctcatagctcacgctgtaggtatctcagttcggtgtaggtc
gttcgctccaagctgggctgtctgcacgaaccccccgttcagcccgaccgctgcgccttatccggtaactatcgtcttgagtcca
acccggtaagacacgacttatcgccactggcagcagccactggtaacaggattagcagagcgaggtatgtaggcggtgctac
agagttcttgaagtggtggcctaactacggctacactagaaggacagtatttggtatctgcgctctgctgaagccagttaccttcg
gaaaaagagaggtagctcttgatccggcaaacaaaccaccgctggtagcggtggatattgatgcaagcagcagattacgcg
cagaaaaaaggatctcaagaagatcattgatcattctacggggtctgacgctcagtggaacgaaaactcacgttaagggattt
tggtcatggctagtgcttggattctcaccaataaaaaacgcccggcggcaaccgagcgttctgaacaaatccagatggagttctg
aggtcattactggatctatcaacaggagtccaagccaattctcgaaccccagagtcccgctcagaagaactcgtcaagaaggc
gatagaaggcgatgcgctgcgaatcgggagcggcgataccgtaaagcacgaggaagcggtcagcccattcgccgccaagc
tcttcagcaatatcacgggtagccaacgctatgtcctgatagcggtccgccacacccagccggccacagtcgatgaatccaga
aaagcggccattaccaccatgatattcggcaagcaggcatcgccgtgggtcacgacgagatcctcgccgtcgggcatacgcg
ccttgagcctggcgaacagttcggctggcgcgagccctcgatgctatcgtccagatcatcctgatcgacaagaccggcttccat
ccgagtacgtgctcgctcgatgcgatgtttcgcttggtggtcgaatgggcaggtagccggatcaagcgtatgcagccgccgcat
tgcatcagccatgatggatacttctcggcaggagcaaggtgagatgacaggagatcctgccccggcacttcgcccaatagca
gccagtcccttccccgcttcagtgacaacgtcgagcacagccgcgcaaggaacgcccgtcgtggccagccacgatagccgcg
ctgcctcgtcttgcagttcattcagggcaccggacaggtcggtcttgacaaaaagaaccgggcgacccctgcgctgacagccgg
aacacgcggcatcagagcagccgattgtctgttgtgcccagtcatagccgaatagcctctccacccaagccgccggagaac
ctgcgtgcaatccatctgacaatcatgcgaaacgatcctcatcctgtctcttgatcagatcttgatccctgcgccatcagatccttt
ggcggcaagaaagccatccagatactagcagggcttcccaaccttaccagagggcggcccaactggcaattcc (MO29)

SEQ ID NO: 5 aatgctactactattagtagaattgatgccaccattcagctcgcgccccaaatgaaaatatagctaaacaggttattgaccatttgc
gaaatgtatctaatggtcaaactaaatctactcgttcgcagaatttgggaatcaactgttatatggaatgaaacttccagacaccgta
catagagcatatttaaaacatgagagctacagcattatattcagcaattaagctctaagccatccgcaaaaatgacctcttatcaa
aaggagcaattaaaggtactctctaatcctgacctgttggagtttgcttccggtctggttcgctttgaagctcgaattaaaacgcgat
atttgaagtattcgggcacctcttaatcatttgatgcaatccgctagcttctgactataatagtcagggtaaagacctgatattgatt
tatggtcattctcgttactgaactgataaagcatttgagggggattcaatgaatatttatgacgattccgcagtattggacgctatcc
agtctaaacatatactattaccccctctggcaaaacttcattgcaaaagcctctcgctattagttattatcgtcgtctggtaaacga
gggttatgatagtgagctcttactatgcctcgtaattccattggcgttatgtatctgcattagttgaatgtggtattcctaaatctcaac
tgatgaatctttctacctgtaataatgttgttccgttagttcgttttattaacgta-
gattttcttcccaacgtcctgactggtataatgagc
cagacttaaaatcgcataaggtaattcacaatgattaaagttgaaattaaaccatctcaagcccaatttactactcgactggtgatc
tcgtcagggcaagccttattcactgaatgagcagctagttacgttgataggtaatgaatatccggacttgtcaagattactatg
atgaaggtcagccagcctatgcgcctggtctgtacaccgttcatctgtcctctttcaaagttggtcagttcggttccctttatgattgac
cgtctgcgcctcgttccggctaagtaacatggagcaggtcgcggatttcgacacaatttatcaggcgatgatacaaatctccgttg
tactagatcgcgcttggtataatcgctggggtcaaagatgagtgattagtgtattatttgcctattcgattaggaggtcgatc
gtagtggcattacgtatatacccgataatggaaacttcctcatgaaaaagtattagtcctcaaagcctctgtagccgagctaccc
tcgaccgatgctgtattcgctgctgagggtgacgatcccgcaaaagcggccataactccctgcaagcctcagcgaccgaata
tatcggttatgcgtgggcgatggttgagtcattgtcggcgcaactatcggtatcaagctgtttaagaaatttcacctcgaaagcaag
ctgataaaccgatacaattaaaggctcataggagccattattggagattacaacgtgaaaaaattattattcgcaattcattagtt
gacctactattctcactccgctgaaactgagaaagttgatagcaaatcccatacagaaaattcatttactaacgtctggaaaga
cgacaaaactttagatcgttacgctaactatgagggctgtctgtggaatgctacaggcgagtagtagtactggtgacgaaactca
gtgttacggtacatgggaccattgggcttgctatccctgaaaatgagggtggtggctctgagggtggcggctcgagggtggc
ggactgagggtggcggtactaaacctcctgagtacggtgatacacctattccgggctatacttatatcaacctctcgacggcac
ttatccgcctggtactgagcaaaaccccgctaatcctaatccactcttgaggagtctcagcctcttaatactacatgatcagaata
ataggttccgaaataggcaggggcattaactgtttatacgggcactgttactcaaggcactgaccccgttaaaacttattaccag
tacactcctgtatcatcaaaagccatgtatgacgcttactggaacggtaaattcagagactgcgctaccattctggattaatgagg
atttatttgatgtgaatatcaaggccaatcgtctgacctgcctcaacctcctgtcaatgctggcggcggctctggtggtggctggtgg
tggcggctctgaggtggtggctctgaggtggcggttctgaggtggcggctctgagggaggcggttccggtggtggctct
ggttccggtgatttgattatgaaaagatggcaaacgctaataaggggctatgaccgaaatgccgatgaaaacgcgctacag
tctgacgctaaaggcaaacttgattctgtcgctactgattacggtgctgctatcgatggatcattggtgacgtaccggcagctaa
tggtaatggtgctactggtgattttgctggctctaattcccaaatggctcaaggtcggtgacggtgataaattcaccataatgaataatt
tccgtcaatatttaccaccctccctcaatcggttgaatgtcgcccattgtctaggcgctggtaaaccatatgaattactattgattgt
gacaaaataaacttattccgtggtgtattgcgatcattatatgagccaccatatgtatgtattactacgtagctaacatactgcgta
ataaggagtcttaatcatgccagacttagggtattccgttattattgcgtacctcggtaccactggtaactagttcggctatctgct
tacttacttaaaaagggcttcggtaagatagctattgctatttcattgatcagctcttattattgggcttaactcaattcagtgggttat
ctctctgatattagcgctcaattaccctctgactttgttcagggtgttcagttaattctc-
ccgtctaatgcgcttccctgttttatgttatt
ctctctgtaaaggctgctattacatattgacgttaaacaaaaaatcgtacttataggattgggataaaataatatggctgatattgt
aactggcaaattaggctctggaaagacgctcgttagcgttggtaagattcaggataaaattgtagctgggtgcaaaatagcaact
aatcttgatttaaggcttcaaaacctcccgcaagtcgggaggacgctaaaacgcctcgcgacttagaataccggataagccact
atatctgatttgcttgctattgggcgcggtaatgattcctacgatgaaaataaaaacggcttgcttgactcgatgagtcggtactt
ggataatacccgttcaggaatgataaggaaagacagccgattattgattggtactacatgctcgtaaattaggatgggatattatt
tacttgacaggactatctattgagataaacaggccgactgcttagctgaacatgactcgtcgtctggacagaatta
cataccattgtcggtacttttatattctcttattactggctcgaaaatgcctctgcctaaattacatgaggcgagttaaatatggcgatt
ctcaattaagccctactgagagcgaggattatactggtaagaatagtataacgcatatgatactaaacaggattactagtaatta
tgattccggtgatattcttatttaacgccttatttcatcacacggtcggtatttcaaaccattaaatttaggtcagaagatgaaattaacta
aaatatatttgaaaaagattctcgcgactagtatgcgattggattttgcatcagcatttacatatagttatataaccccaacctaagcc
ggaggttaaaaaggtagtctctcagacctatgattagatataattcactattgactatctcagcgtcttaatctaagctatcgctatga
ttcaaggattctaagggaaaattaattaatagcgacgatttacagaagcaaggttattcactcacatatattgatttatgtactgatcc
attaaaaaaggtaattcaaatgaaattgttaaatgtaattaattagattcttgatgatgatcatcatatatttgctcaggtaattgaaa
tgaataattcgcctctgcgcgattagtaacttggtatttcaaagcaatcaggcgaatccgttattgtttctcccgatgtaaaaggtact
gttactgtatattcatctgacgttaaacctgaaaatctacgcaatttattatactactacgtgcaaatattagatgaaaaccatcattatt
aaccatccattattcagaagtataatccaaacaatcaggattatattgatgaattgccatcatctgataatcaggaatatgatgataa
accgctccactggtggatattgaccgcaaaatgataatgttactcaaactataaaattaataacgttcgggcaaaggattttaata
cgagagtcgaattgatgtaaagtctaatacactaaatcctcaaatgtattatctattgacggctctaatctattagagttagtgctcct
aaagatattttagataaccttcctcaattcctttcaactgttgatttgccaactgaccagatattgattgagggtttgatatttgaggttc -continued

SEQUENCES agcaaggtgatgctttagattttttcatttgctgctggctctcagcgtggcactgttgcaggcggtgttaatactgaccgcctcacctc
tgttttatcttctgctggtggttcgttcggtattttaatggcgatgttttagggctatcagttcgcgcattaaagactaatagccattca
aaaatattgtctgtgccacgtattcttacgattcaggtcagaagggactatctctgaggccagaatgtcccattattactggtcgt
gtgactggtgaatctgccaatgtaaataatccatttcagacgattgagcgtcaaaatgtaggtataccatgagcgtattcctgagc
aatggctggcggtaatattgactggatattaccagcaaggccgatagatgagacttctactcaggcaagtgatgttattactaatc
aaagaagtattgctacaacggttaatttgcgtgatggacagactcattactcggtggcctcactgattataaaaacacactcagga
actggcgtaccgacctgtctaaaatcccataatcggcctcctgatagctcccgctctgattctaacgaggaaagcacgttatacg
tgctcgtcaaagcaaccatagtacgcgccctgtagcggcgcattaagcgcggcgggtgtggtggttacgcgcagcgtgaccg
ctacacttgccagcgccctagcgcccgctccatcgattcaccatcctactcgccacgttcgccggctaccccgtcaagctcta
aatcgggggctccattagggaccgatttagtgattacggcacctcgaccccaaaaaacttgatagggtgatggacacgtagt
gggccatcgccctgatagacgtattcgccattgacgaggagtccacgttattaatagtggactcttgaccaaactggaacaa
cactcaaccctatctcgggctattcattgatttataagggattagccgatttcggaaccaccatcaaacaggattacgcctgctgg
ggcaaaccagcgtggaccgcttgctgcaactctctcagggccaggcggtgaagggcaatcagctgagcccgtctcactggtg
aaaagaaaaaccaccctggcgcccaatacgcaaaccgcctctccccgcgcgaggccgattcattaatgcagctggcacgaca
ggtttcccgactggaaagcgggcagtgagcgcaacgcaattaatgtgagttagctcactcattaggcacccaggctttacactt
tatgatccggctcgtatgagtgtggaattgtgagcggataacaatttcacacaggaaacagctatgaccatgattacgaattcga
gctctgactactgatggattctcaccaataaaaaacgcccggcggcaaccgagcgactgaacaaatccagatggagactga
ggtcattactggatctatcaacaggagtccaagccaattctcgaacgatcaattcagcggcaacgggagccgtgataacggct
ggcaaagaacagcagcggctgggggggcattcgcctccggcactccacaggcgctaacgcgcgcaatgaagagcgtgtggt
cgtgtacttcaaccgtgctctccacctcgcattcgaaccaggccatggcgtcccgcagagtggggaggccggcctgaactgtg
aaagcaggaggaggagtgccatcgatcacacgcttgctgaagaatgccgataacatcactgactacacccaggaggctgac
gccgaagcgtccgccttgagtcagcagctcatgcataccgcccgacttcagggacaccatcacagtcggcgggtccagactg
atggaggtgaagctgacaccgtcatgccatgcacttcgccctcgtcagtctccgcgctgagaaccgcaattcccgtcgcgaac
agtgcaaccgcctggcggaagctggtggagtcgatatccaccaccacatattaacgtcatttgaatcacccaggagttagg
gctccgctggccttgaccagcggagcaatagcgtcaggccgcaatagtgggtgcgtactggctgcaccactgaccgatacgtt
ccgggctggagaagcgatcccactgaagaccggatagttgaagagtccgtgaactcatcagccatttcacggctctggctcag
gatctgaaggaaggtgaggaattccggcggaagttccgtgaaggcgctcagagtgaagttggtccagcgggtggcgcacag
cacgcgatcctggcggcgacgctccaggtgttcgctgaagcgcaggtcgtagacaggtgcgcaaggatttcctcgcccaga
atccatgccgcataggacgccatgacgcgccctggcccaagaccggatctgacagagcctggatgtcgcccagcccgatgat
ggattgccgttattgagggtcgcatgaccgtcgcggaatactggcacaacaccgccctggaggatgtccagagaactgaggc
caggtcgaactcagccggatcgatgcgctcggcaacggaaggatgatgcttacgcagatctccagcatcagatcgaggaac
gcacgcgggtcatcgtcatacttggtgtgggcgaggacttccagatcgctaccaatatgattcgagcaccagcgctgtgctca
tgccattgaacgacagggaggaatctcaatcagctcgccatgccctggcgagaaggacatagtcaccgccgaatcggtgctt
ccttgatgcccttgaagagaccaacgcacagtgcccgttgcggcttctcgaagggcgagattcggactgcttctcgaacacctt
gccgagggcgtatttaccagtgcacacaaccagcagatcatactgctccgacagccatccagatatcggcagacacggcgt
cgtagcagaacttgccgcccctggcttccagtgcacgcatcagcatcggcaggtagagacggtagtccactgcacggctggg
agccttgagatcaccgtagaaacgcatgggctgcggcccacctacgtagtagtggtggccgaaatagccaaactcctcagacg
gccactcattgacgtcgagggcaaccctcccgctgcaccgtcaccgcgagtgagcaacggtattcaggagccgcagtccactg
tactcatcgggcttacgatcagtgtacacagtgacgtcgacgtcatgctggcggaggaagaggccaagatggaggccggcag
tgcctgcaccaacaataccgatacgctattcatgcatgctacctccttaatcatcagctgtatggagaaacagtagagagagcg
ataaaaagcgtcaggtatgatcccgctaatcttatggataaaaatgctatggcatagcaaagtgacgccgtgcaaataatcaatg
tggacttactgccgtgattatagacacttagttacgcgcattgtcatggctaggtcccgctagttacagaatgatttaataagcg
gggttaccggtttggttagcgagaagagccagtaaaagacgcagtgacggcaatgtctgatgcaatatggactattggtttcttg
gtacccggggatcctctagagtcgacctgcaggcatgcaagcaggcactggccgtcgattacaacgtcgtgactgggaaaac
cctggcgttacccaacttaatcgccagcagcacatcccccattcgccagctggcgtaatagcgaagaggcccgcaccgatcgc
ccacccaacagagcgcagcctgaatggcgaatggcgcgtagcctggatccggcaccagaagcggtgccggaaagctggct
ggagtgcgatcacctgaggccgatactgtcgtcgtccctcaaactggcagatgcacggttacgatgcgcccatctacaccaa
cgtgacctatcccattacggtcaatccgccgatgacccacggagaatccgacgggagttactcgctcacatttaatgagatgaa
agctggctacaggaaggccagacgcgaattatattgatggcgacctattggttaaaaaatgagctgatttaacaaaaatttaatg
cgaattttaacaaaatattaacgatacaatttaaatatttgcttatacaatcacctgataggggcattctgattatcaaccggggtac
atatgattgacatgctagattacgattaccgttcatcgattctcttgatgctccagactctcaggcaatgacctgatagcattgtag
atctctcaaaaatagctaccctctccggcattaatttatcagctagaacggagaatatcatattgatggtgatttgactgtctccggc
catctcacccattgaatcatacctacacattactcaggcattgcatttaaaatatatgagggactaaaaattatatccagcgagaa
ataaaggcactcccgcaaaagtattacagggtcataatgataggtacaaccgatttagattatgctctgaggcatattgcttaatt
ttgctaattctttgccttgcctgtatgatttattggatgtt (M030)

SEQ ID NO: 6 aatgctactactattagtagaattgatgccaccattcagctcgcgccccaaatgaaaatatagctaaacaggttattgaccatttgc
gaaatgtatctaatggtcaaactaaatctactcgttcgcagaattgggaatcaactgttatatggaatgaaacttccagacaccgta
catagagcatatttaaaacatgagagctacagcattatattcagcaattaagctctaagccatccgcaaaaatgacctcttatcaa
aaggagcaattaaaggtactctctaatcctgacctgttggagtttgcttccggtctggttcgcttttgaagctcgaattaaaacgcgat
atttgaagtattcgggcacctcttaatcatttgatgcaatccgctgacttctgactataatagtcaggtaaagaccgatattgatt
tatggtcattctcgttactgaactgataaagcattgagggggattcaatgaatatttatgacgattccgcagtattggacgctatcc
agtctaaacatatactattaccccctctggcaaaacttcattgcaaaagcctctcgctattaggtattatcgtcgtctggtaaacga
gggttatgatagtgagctcttactatgcctcgtaattccattggcgtatctgcattagttgaatgtggtattcctaaatctcaac
tgatgaatctttctacctgtaataatgttgttccgttagttcgtttttattaacgta-
gattttcttcccaacgtcctgactggtataatgagc
cagacttaaaatcgcataaggtaattcacaatgattaaagttgaaattaaaccatctcaagcccaatttactactcgactggtgatc
tcgtcagggcaagccttattcactgaatgagcagctagttacgttgatagggtaatgaatatccggacttgtcaagattactatg
atgaaggtcagccagcctatgcgcctggtctgtacaccgttcatctgtcctctttcaaagttggtcagttcggttcccttatgattgac
cgtctgcgcctcgaccggctaagtaacatggagcaggtcgcggatttcgacacaatttatcaggcgatgatacaaatctccgag
tactagatcgcgcttggtataatcgctgggggtcaaagatgagtgattagtgtattatttgcctattcgattaggaggtgcatc
gtagtggcattacgtatataccgataagtggaaacttcctcatgaaaaagtattagtcctcaaagcctctgtagcgagctaccc
tcgaccgatgctgtattcgctgctgagggtgacgatcccgcaaaagcggccataactccctgcaagcctcagcgaccgaata
tatcggttatgcgtgggcgatggagagtcattgtcggcgcaactatcggtatcaagctgataagaaattcacctcgaaagcaag
ctgataaaccgatacaattaaaggctcataggagccattattggagattacaacgtgaaaaaattattattcgcaattcattagtt
gacctactattctcactccgctgaaactgagaaagttgatagcaaaatcccatacagaaaattcatttactaacgtctggaaaga -continued

SEQUENCES

```
cgacaaaactttagatcgttacgctaactatgagggctgtctgtggaatgctacaggcgagtagtagtactggtgacgaaactca
gtgttacggtacatgggacctattgggcttgctatccctgaaaatgagggtggtggctctgagggtggcggactgagggtggc
ggactgagggtggcggtactaaacctcctgagtacggtgatacacctattccggctatacttatatcaaccctctcgacggcac
ttatccgcctggtactgagcaaaaccccgctaatcctaatccactcttgaggagtctcagcctcttaatactacatgatcagaata
ataggttccgaaataggcaggggggcattaactgtttatacgggcactgttactcaaggcactgaccccgttaaaacttattaccag
tacactcctgtatcatcaaaagccatgtatgacgcttactggaacggtaaattcagagactgcgctaccattctggattaatgagg
atttatttgatgtgaatatcaaggccaatcgtctgacctgcctcaacctcctgtcaatgctggcggcggctctggtggtggactgg
tggcggctctgagggtggtggctctgagggtggcggttctgagggtggcggctctgagggaggcggttccggtggtggctct
ggttccggtgattttgattatgaaaagatggcaaacgctaataaggggggctatgaccgaaaatgccgatgaaaacgcgctacag
tctgacgctaaaggcaaacttgattctgtcgctactgattacggtgctgctatcgatggatcattggtgacgtaccggccagctaa
tggtaatggtgctactggtgattttgctggctctaattcccaaatggctcaagtcggtgacggtgataattcaccataatgaataatt
tccgtcaatatttaccaccctcccctcaatcggttgaatgtcgcccattgtctaggcgctggtaaaccatatgaattactattgattgt
gacaaaataaacttattccgtggtgtattgcgatcattatatgagccaccatatgtatgtattactacgtagctaacatactgcgta
ataaggagtcttaatcatgccagacttagggtattccgttattattgcgtacctcggtaccactggtaactagttcggctatctgct
tacttacttaaaaagggcttcggtaagatagctattgctatttcattgatcagctctttattattgggcttaactcaattcagtgggttat
ctctctgatattagcgctcaattaccctctgactttgttcagggtgttcagttaattctc-
ccgtctaatgcgcttccctgttttttatgttatt
ctctctgtaaaggctgctattacatattgacgttaaacaaaaaatcgtacttataggattgggataaataatatggctgatattagt
aactggcaaattaggctctggaaagacgctcgttagcgttggtaagattcaggataaaattgtagctgggtgcaaaatagcaact
aatcttgatttaaggcttcaaaacctcccgcaagtcgggaggacgctaaaacgcctcgcgacttagaataccggataagccact
atatctgatttgcttgctattgggcgcggtaatgattcctacgatgaaaataaaaacggcttgcttgactcgatgagtgcggtactt
ggataatacccgttcaggaatgataaggaaagacagccgattattgattggtactacatgctcgtaaattaggatgggatattatt
tacttgacaggacttatctattgagataaacaggcgcgactgcattagctgaacatgagatattgtcgtcgtctggacagaatta
cataccattgtcggtactttatattctcttattactggctcgaaaatgcctctgcctaaattacattacatgaggcggttaaatatggcgatt
ctcaattaagccctactgagagcgaggattatactggtaagaataagtataacgcatatgatactaaacaggattactagtaatta
tgattccggtgatattcttatttaacgccttatttatcacacggtcggtatttcaaaccattaaatttaggtcagaagatgaaattaacta
aaatatatttgaaaagattctcgcgactagtatgcgattggatttgcatcagcatttacatatagtttatataaccaacctaagcc
ggaggttaaaaaggtagtctctcagacctatgattagataaattcactattgactatctcagcgtcttaatctaagctatcgctatga
ttcaaggattctaagggaaaattaattaatagcgacgatttacagaagcaaggttattcactcacatatattgatttatgtactgatcc
attaaaaaaggtaattcaaatgaaattgttaaatgtaattaattagattcttgatgatgatcatcatatatttgctcaggtaattgaaa
tgaataattcgcctctgcgcgattagtaacttggtattcaaagcaatcaggcgaatccgttattgatctcccgatgtaaaaggtact
gttactgtatattcatctgacgttaaacctgaaaatctacgcaaatttattatactgattacgtgcaaataattagatatggtaggact
aaccatccattattcagaagtataatccaaacaatcaggattatattgatgaattgccatcatctgataatcaggaatatgatgataa
accgctccactggtggatattgaccgcaaaatgataatgttactcaaactataaaattaataacgttcgggcaaaggatttaata
cgagagtcgaattgatgtaaagtctaatacactaaatcctcaaatgtattatctattgacggctctaatctattagagttagtgctcct
aaagtatttttagataaccttcctcaattcctttcaactgttgatttgccaactgaccagatattgattgagggtttgatatttgaggttc
agcaaggtgatgctttagattttcatttgctgctggctctcagcgtggcactgttgcaggcggtgttaatactgaccgcctcacctc
tgtttatcttctgctggtggttcgttcggtattttaatggcgatgttttagggctatcagttcgcgcattaaagactaatagccattca
aaaatattgtctgtgccacgtattcttacgattcaggtcagaagggactatctctgaggccagaatgtcccattattactggtcgt
gtgactggtgaatctgccaatgtaaataatccattcagacgattgagcgtcaaaatgtaggtataccatgagcgtattcctgagc
aatggctggcggtaatattgactggatattaccagcaaggccgatagatgagactttctactcaggcaagtgatgttattactaatc
aaagaagtattgctacaacggttaatttgcgtgatggacagactcattactcggtggcctcactgattataaaaacacactcagga
actggcgtaccgacctgtctaaaatcccataatcggcctcctgatagctcccgctctgattctaacgaggaaagcacgttatacg
tgctcgtcaaagcaaccatagtacgcgccctgtagcggcgcattaagcgcggcgggtgtggtggttacgcgcagcgtgaccg
ctacacttgccagcgccctagccgccgctccatcgattcaccatcctactcgccacgttcgccggctacccgtcaagctcta
aatcgggggctccattagggaccgatttagtgattacggcacctcgaccccaaaaaacttgataggggtgatggacacgtagt
gggcatcgccctgatagacggtattcgccattgacgaggagtccacgttattaatagtggactcttgaccaaactggaacaa
cactcaaccctatctcgggctattcattgatttataagggattagccgatttcggaaccaccatcaaacaggattacgcctgctgg
ggcaaaccagcgtggaccgcttgctgcaactctctcagggccaggcggtgaagggcaatcagctgagcccgtctcactggtg
aaaagaaaaaccaccctggcgcccaatacgcaaaccgcctctccccgcgcgaggccgattcattaatgcagctggcacgaca
ggtttccgactggaaagcgggcagtgagcgcaacgcaattaatgtgagttagctcactcattaggcaccccaggctttacactt
tatgatccggctcgtatgagtgtggaattgtgagcggataacaatttcacacaggaaacagctatgaccatgattacgaattcga
gctctgactactgatggattctcaccaataaaaaacgcccggcgcaaccgcctttccccctgtgacgtcttcccatcatggcagtg
gtcattactggatctatcaacaggagtccaagcaattctcgaacgatcaattcagcggcaacgggagccgtgataacggct
ggcaaagaacagcagcggctgggggcattcgcctccggcactccacaggcgctaacgcgcgcaatgaagagcgtgtggt
cgtgtacttcaaccgtgctctccacctcgcattcgaaccaggccatggcgtcccgcagagtggggaggccggcctgaactgtg
aaagcaggaggaggagtgccatcgatcacacgcttgctgaagaatgccgataacatcactgactacaccaggaggctgac
gccgaagcgtccgccttgagtcagcagctcatgcatacgcccgacttcagggacaccatcacagtcggcgggtccagactg
atggaggtgaagctgacaccgtcatgccatgcacttcgccctcgtcagtctccgcgctgagaaccgcaattcccgtcgcgaac
agtgcaaccgcctggcggaagctggtggagtcgatatccaccaccacatattattaacgtcatttgaatcacccaggagttagg
gctccgctggccttgaccagcggagcaatagcgtcaggccgcaatagtgggtgcgtactggctgcaccactgaccgatacgtt
ccgggctggagaagcgatcccactgaagaccggatagttgaagatccgtgaactcatcagccatttcacggctctggctcag
gatctgaaggaaggtgaggaattccggcgaagttccgtgaaggcgctcagagtgaagttggtccagcgggtggcgcacag
cacgcgatcctggcggcgacgtccaggtgttcgctgaagcgcaggtcgtagacagagtgcgcaaggatttcctcgcccaga
atccatgccgcataggacgccatgacgcgccctggcccaagaccggatcggaggcctggatgtcgcccagcccgatgat
ggattgccgttattgagggtcgcatgaccgtcgcggaatactggcacaacaccgccctggaggatgtccagagaactgaggc
caggtcgaactcagccggatcgatgcgctcggcaacggaaggatgatgcttacgcagatctccagcatcagatcgaggaac
gcacgcgggtcatcgtcatacttggtgtgggcgaggacttccagatcgctaccaatatggattcgagcaccagcgctgtgctca
tgccattgaacgacagggaggaatctcaatcagctcgccatgccctggcgagaaggacatagtcaccgcgcgaatcggtgctt
ccttgatgcccttgaagagaccaacgcacagtgccccgttgcggttctctcgaagggcgagattcggactgcttctctcgaaccctt
gccgagggcgtatttaccagtgcacacaaccagcagatcatactgctccgacagccatccagatatcggcacgcacgcgt
cgtagcagaacttgccgcccctggcttccagtgcacgcatcagcatcggcaggtagacggtagtccactgcacggctggg
agccttgagatcaccgtagaaacgcatgggctgcggcccacctacgtagtagtagtggccgaaatagccaaactcctcagacg
gccactcattgacgtcgagggcaacctcccgctgcaccgtcaccgcggtgcaacggtattcaggagccgcagtccactg
tactcatcgggcttacgatcagtgtacacagtgacgtcgacgtcatgctggcggaggaagaggccaagatggaggccgcag
tgcctgcaccaacaataccgatacgctattcatgcatgctacctcctaatccttcagctgggtcagtcgctcctgctgatgtgctc
agtatctctatcactgatagggatgtcaatctctatcactgatagggaggtacccggggatcctctagagtcgacctgcaggcatg
caagcaggcactggccgtcgattacaacgtcgtgactgggaaaaccctggcgttacccaacttaatcgccagcagcacatcc
```

-continued

SEQUENCES ccattcgccagctggcgtaatagcgaagaggcccgcaccgatcgccatcccaacagagcgcagcctgaatggcgaatggc
gctagcctggtaccggcaccagaagcggtgccggaaagctggctggagtgcgatatcctgaggcgatactgtcgtcgtcc
cctcaaactggcagatgcacggttacgatgcgcccatctacaccaacgtgacctatcccattacggtcaatccgccgatgaccc
acggagaatccgacgggagttactcgctcacatttaatgagatgaaagctggctacaggaaggccagacgcgaattatattga
tggcgacctattggttaaaaaatgagctgatttaacaaaaatttaatgcgaatataacaaaatattaacgatacaatttaaatatttg
cttatacaatcacctgatagggggcattctgattatcaacggggtacatatgattgacatgctagattacgattaccgttcatcgat
tctcttgatgctccagactctcaggcaatgacctgatagcctagtagatctctcaaaaatagctaccctctccggcattaatttatca
gctagaacggttgaatatcatattgatggtgatttgactgtctccggcctttctcacccttttgaatctttacctacacattactcaggc
attgcattaaaatatatgagggactaaaaattatatcatgcgagaaataaaggcttctcccgcaaaagtattacagggtcataat
gataggtacaaccgatttagattatgctctgaggattattgcttaattagctaattattgccagcctgtatgatttattggatga (pLT006)

SEQ ID NO: 7 gacgtctgtgcaagtactactgactgcagtcacttgaattcgatacccagctgggtggagtgcaccaaggagcatgcgaagga
aacgatcgcagaagatccgcaaggtaccactagccgcggagtatagtacatttgaaggatcctcaagtcggccgcccgttcc
atggatactcgtcgaccattacgctagccgtctggagctcggactgcttaagtcgctccatatgctgaaatgagctgagacaatta
atcatccggctcgtataatgtgtggaattgtgagcggataacaatttcacaccccgggataaggaggacaattgatgcgtaaagg
agaagaactatcactggagagtcccaattcttgagaattagatggtgatgttaatgggcacaaattactgtcagtggagagggt
gaaggtgatgcaacatacgaaaacttaccctaaattatttgcactactggaaaactacctgaccgtggccaacacttgtcact
actacggttatggtgacaatgctagcgagataccagatcacatgaaacagcatgactattcaagagtgccatgcccgaaggt
tacgtacaggaaagaactatattatcaaagatgacgggaactacaagacacgtgctgaagtcaagatgaaggtgatacccagt
taatagaatcgagttaaaaggtattgatataaagaagatggaaacattcaggacacaaattggaatacaactataactcacacaa
tgtatacatcatggcagacaaacaaaagaatggaatcaaagttaacttcaaaattagacacaacattgaagatggaagcgttcaa
ctagcagaccattatcaacaaaatactccgattggcgatggccctgtccattaccagacaaccattacctgtccacacaatctgcc
catcgaaagatcccaacgaaaagagagaccacatggtccacttgagtgtaaccgctgctgggattacacatggcatggatg
aactatacaaataaggcgccagggttgatatctatcgccctagggaccgtctcgagagaatcaatattaatccaacgcgtggcat
caaataaaacgaaaggctcagtcgaaagactgggccatcgattatctgagtagtcggtgaacgctctcctgagtaggacaaat
ccgccgccctagacttaggcgttcggctgcggcgagcggtatcgatcactcaaaggcggtaatacggttatccacagaatca
gggggataacgcaggaaagaacatgtgagcaaaaggccagcaaaaggccaggaaccgtaaaaaggccgcgttgctggcgttt
ttccataggctccgcccccctgacgagcatcacaaaaatcgacgctcaagtcagaggtggcgaaacccgacaggactataaa
gataccaggcgtttccccctggaagctccctcgtgcgctctcctgttccgaccctgccgcttaccggatacctgtccgcctttctcc
cacgggaagcgtggcgctttcatagctcacgctgtaggtatctcagttcggtgtaggtcgttcgctccaagctgggctgtgtgtg
cacgaaccccccgttcagcccgaccgctgcgccttatccggtaactatcgtcttgagtccaacccggtaagacacgacttatcg
ccactggcagcagccactggtaacaggattagcagagcgaggtatgtaggcggtgctacagagttcttgaagtggtggcctaa
ctacggctacactagaaggacagtataggtatctgcgctctgctgaagccagttaccacggaaaaagagaggtagctcttgat
ccggcaaacaaaccaccgctggtagcggtggtttttttgtttgcaagcagcagattacgcgcagaaaaaaaggatctcaagaag
atcattgatatactacggggtctgacgctcagtggaacgaaaactcacgttaagggattttggtcatgagattatcaaggatctt
caccaataaaaaacgcccggcggcaaccgagcgactgaacaaatccagatggagactgaggtcattactggatctatcaaca
ggagtccaagccaattctcgaaccccagagtcccgctcagaagaactcgtcaagaaggcgatagaaggcgatgcgctgcga
atcgggagcggcgataccgtaaagcacgaggaagcggtcagcccattcgccgccaagctcttcagcaatatcacgggtagcc
aacgctatgtcctgatagcggtccgccacacccagccggccacagtcgatgaatccagaaaagcggccattaccaccatgata
ttcggcaagcaggcatcgccgtgggtcacgacgagatcctcgccgtcgggcatacgcgccttgagcctggcgaacagttcgg
ctggcgcgagcccctgatgctcgtccgatcatcctgatcgacaagaccggcaccatccgagtacgtgctcgctcgatgcg
atgatcgcaggtggtcgaatgggcaggtagccggatcaagcgtatgcagccgccgcattgcatcagccatgatggatactact
cggcaggagcaaggtgagatgacaggagatcctgccccggcacttcgcccaatagcagccagtcccacccgcttcagtgac
aacgtcgagcacagccgcgcaaggaacgcccgtcgtggccagccacgatagccgcgctgcctcgtcttgcagttcattcagg
gcaccggacaggtcggtcttgacaaaaagaaccgggcgaccctgcgctgacagccggaacacggcggcatcagagcagcc
gattgtctgttgtgcccagtcatagccgaatagcctctccacccaagccgccggagaacctgcgtgcaatccatcttgttcaatca
tgcgaaacgatcctcatcctgtctcttgatcagatcttgatccctgcgccatcagatccttggcggcaagaaagccatccagttta
ctttgcagggcttcccaaccttaccagagggcggcccaactggcaattcc (pPh006)

SEQ ID NO: 8 gacgtctgtgcaagtactactgttctgcagtcacttgaattcgatacccagctgggtggagtgcaccaaggagcatgcgaagga
aacgtttcgcagaagcttccgcaaggtaccacttgccgcggagtatttgtacatttgaaggatcctcaagtcggccgcccgttcc
atggatactcgtcgaccattacgctagccgtctggagctcggactgcttaagtcgctccatatgctgaaatgagctgttgacaatta
atcatccggctcgtataatgtgtggaattgtgagcggataacaatttcacaccccgggataaggaggacaattgatgcgtaaagg
agaagaacttttcactggagttgtcccaattcttgttgaattagatggtgatgttaatgggcacaaattactgtcagtggagagggt
gaaggtgatgcaacatacgaaaacttaccctaaattatttgcactactggaaaactacctgttccgtggccaacacttgtcact
acttcggttatggtgttcaatgctttgcgagataccagatcacatgaaacagcatgactttttcaagagtgccatgcccgaaggt
tacgtacaggaaagaactatattatcaaagatgacgggaactacaagacacgtgctgaagtcaagtttgaaggtgataccttgt
taatagaatcgagttaaaaggtattgattttaaagaagatggaaacattcttggacacaaattggaatacaactataactcacacaa
tgtatacatcatggcagacaaacaaaagaatggaatcaaagttaacttcaaaattagacacaacattgaagatggaagcgttcaa
ctagcagaccattatcaacaaaatactccgattggcgatggccctgtccttttaccagacaaccattacctgtccacacaatctgcc
ctttcgaaagatcccaacgaaaagagaccacatggtccttcttgagtttgtaaccgctgctgggattacacatggcatggatg
aactatacaaataaggcgccagggttgatatctatcgccctagggaccgtctcgagagcgccctgtagcggcgcattaagcgc
ggcgggtgtggtggttacgcgcagcgtgaccgctacacttgccagcgccctagcgcccgctccttttcgctttcttcccttcct
cgccacgttcgccggctttccccgtcaagctctaaatcgggggctccctttagggttccgatttagtgctttacggcacctcgacc
ccaaaaaacttgattagggtgatggttcacgtagtgggccatcgccctgatagacggttttcgccctttgacgttggagtccacgt
tctttaatagtggactcttgttccaaactggaacaacactcaaccctatctcggtctattcttttgatttataagggattttgccgatttc
ggcctattggttaaaaaatgagctgatttaacaaaaatttaacgcgaattaaatattaatccaacgcgtggcatcaaataaaacgaa
aggctcagtcgaaagactggttttcgtttgtggcggtgaacgtctcctgtaggaacaaatccgccgcctaga
cttaggcgttcggctgcggcgagcggtatcagctcacctcaaaggcggtaatacggttatccacagaatcaggggataacgcag
gaaagaacatgtgagcaaaaggccagcaaaaggccaggaaccgtaaaaaggccgcgttgctggcgttttttccataggctccg
cccccctgacgagcatcacaaaaatcgacgctcaagtcagaggtggcgaaacccgacaggactataaagataccaggcgttt
cccctggaagctcctcgtgcgctctcctgttccgaccctgccgcttaccggatacctgtccgcctttctccttcgggaagcgt
ggcgctttctcatagctcacgctgtaggtatctcagttcggtgtaggtcgttcgctccaagctgggctgtgtgcacgaacccccg -continued

SEQUENCES ttcagcccgaccgctgcgccttatccggtaactatcgtcttgagtccaaccggtaagacacgacttatcgccactggcagcagc
cactggtaacaggattagcagagcgaggtatgtaggcggtgctacagagttcttgaagtggtggcctaactacggctacactag
aaggacagtatttggtatctgcgctctgctgaagccagttaccttcggaaaaagagttggtagctatgatccggcaaacaaacc
accgctggtagcggtggttttttttgtttgcaagcagcagattacgcgcagaaaaaaaggatctcaagaagatcctttgatcttttcta
cggggtctgacgctcagtggaacgaaaactcacgttaagggattttggtcatggctagtgcttggattctcaccaataaaaaacg
cccggcggcaaccgagcgttctgaacaaatccagatggagttctgaggtcattactggatctatcaacaggagtccaagccaat
tctcgaacccagagtcccgctcagaagaactcgtcaagaaggcgatagaaggcgatgcgctgcgatcgggagcggcgat
accgtaaagcacgaggaagcggtcagccattcgccgccaagctcttcagcaatatcacgggtagccaacgctatgtcctgat
agcggtccgccacacccagccggccacagtcgatgaatccagaaaagcggccattttccaccatgatattcggcaagcaggc
atcgccgtgggtcacgacgagatcctcgccgtcgggcatacgcgccttgagcctggcgaacagttcggctggcgcgagccc
tgatgctatcgtccagatcatcctgatcgacaagaccggcttccatccgagtacgtgctcgctcgatgcgatgtttcgcttggtgg
tcgaatgggcaggtagccggatcaagcgtatgcagccgccgcattgcatcagccatgatggataagcttcggagcaag
gtgagatgacaggagatcctgcccggcacttcgcccaatagcagccagtcccttcccgcttcagtgacaacgtcgagcacag
ccgcgcaaggaacgcccgtcgtggccagccacgatagccgcgctgcctcgtcttgcagttcattcagggcaccggacaggtc
ggtcttgacaaaaagaaccgggcgaccctgcgctgacagccggaacacggcggcatcagagcagccgattgtctgttgtgcc
cagtcatagccgaatagcctctccacccaagccgccggagaacctgcgtgcaatccatcttgttcaatcatgcgaaacgatcctc
atcctgtctcttgatcagatcttgatccctgcgccatcagatcctgtcggcaagaaagccatccagtttactttgcagggcttcc
caaccttaccagagggcggcccaactggcaattcc (M6G bacteriophage)

SEQ ID NO: 9 aatgctactactattagtagaattgatgccacctttcagctcgcgccccaaatgaaaatatagctaaacaggttattgaccattttgc
gaaatgtatctaatggtcaaactaaatctactcgttcgcagaattgggaatcaactgttatatgaatgaaacttccagacaccgta
ctttagttgcatatttaaaacatgttgagctacagcattatattcagcaattaagctctaagccatccgcaaaaatgacctcttatcaa
aaggagcaattaaaggtactctctaatcctgacctgttggagtttgcttccggtctggttcgctttgaagctcgaattaaaacgcgat
atttgaagtcttctgggcttcctcttaatctttttgatgcaatccgattgcttctgac-
tataatagtcagggtaaagacctgatttttgatt
tatggtcattctcgttttctgaactgtttaaagcatttgaggggattcaatgaatatttatgacgattccgcagtattggacgctatcc
agtctaaacattttactattacccctcctctggcaaactcttttgcaaaagcctctcgctattttggtttttatcgtcgtctggtaaacga
gggttatgatagtgttgctcttactatgcctcgtaattcctttggcgttatgtatctg-
cattagttgaatgtggtattcctaaatctcaac
tgatgaatctttctacctgtaataatgttgttccgttagttcgttttattaacgta-
gattttcttcccaacgtcctgactggtataatgagc
cagttcttaaaatcgcataaggtaattcacaatgattaaagttgaaattaaaccatctcaagcccaatttactactcgttctggtgtttc
tcgtcagggcaagccttattcactgaatgagcagctttgttacgttgatttgggtaatgaatatccggttcttgtcaagattactcttg
atgaagtcagccagcctatgcgcctggtctgtacaccgttcatctgtcctattcaaagttggtcagttcggttccatatgattgac
cgtctgcgcctcgttccggctaagtaacatggagcaggtcgcggattcgacacaatttatcaggcgatgatacaaatctccgttg
tactttgtttcgcgcttggtataatcgctgggggtcaaagatgagtgttttagtgtattcttttgcctattcgttttaggttggtgccttc
gtagtggcattacgtatttaccgtttaatggaaacttcctcatgaaaaagtcttttagtcctcaaagcctctgtagcgttgctaccc
tcgaccgatgctgtattcgctgctgagggtgacgatcccgcaaaagcggccataactccctgcaagcctcagcgaccgaata
tatcggttatgcgtgggcgatggagagtcattgtcggcgcaactatcggtatcaagctgataagaaattcacctcgaaagcaag
ctgataaaccgatacaattaaaggctcataggagccattattggagattacaacgtgaaaaaattattattcgcaattcattagtt
gacctactattctcactccgctgaaactgagaaagttgatagcaaaatcccatacagaaaattcatttactaacgtctggaaaga
cgacaaaacttagatcgttacgctaactatgagggctgtctgtggaatgctacagggcgagtagtagtactggtgacgaaactca
gtgttacggtacatgggacctattgggcttgctatccctgaaaatgagggtggtggctctgagggtggcggactgagggtggc
ggactgagggtggcggtactaaacctcctgagtacggtgatacacctattccgggctatacttatatcaaccctctcgacggcac
ttatccgcctggtactgagcaaaacccccgctaatcctaatccactcttgaggagtctcagcctcttaatactacatgatcagaata
ataggttccgaaataggcaggggcattaactgtttatacgggcactgttactcaaggcactgaccccgttaaaacttattaccag
tacactcctgtatcatcaaaagccatgtatgacgcttactggaacggtaaattcagagactgcgctaccattctggattaatgagg
atttatttgatgtgaatatcaaggccaatcgtctgacctgcctcaacctcctgtcaatgctggcggcggctctggtggtggactgg
tggcggctctgagggtggtggctctgagggtggcggttctgagggtggcggctctgagggaggcggttccggtggtggctct
ggttccggtgattttgattatgaaaagatggcaaacgctaataagggggctatggctaaaagccgagaaaatcgccgatacag
tctgacgctaaaggcaaacttgattctgtcgctactgattacggtgctgctatcgatggatcattggtgacgtaccggcagctaa
tggtaatggtgctactggtgattttgctggctctaattcccaaatggctcaagtcggtgacggtgataattcaccataatgaataatt
tccgtcaatatttaccaccctccctcaatcggttgaatgtcgcccattgtctaggcgctggtaaaccatatgaattactattgattgt
gacaaaataaacttattccgtggtgtcgctgatcattatatgagcaccatatctgatgtttactacgtagctgctaacactgcgta
ataaggagtcttaatcatgccagacttagggtattccgttattattgcgtacctcggtaccactggtaactagttcggctatctgct
tacttacttaaaaagggcttcggtaagatagctattgctattcattgatcagctcttattattgggcttaactcaattcagtgggttat
ctctctgatattagcgctcaattaccctctgactttgttcagggtgttcagttaattctc-
ccgtcaatgcgcttccctgtttttatgttatt
ctctctgtaaaggctgctattacatattgacgttaaacaaaaaatcgtacttataggattgggataaataatatggctgatattgt
aactggcaaattaggctctggaaagacgctcgttagcgttggtaagattcaggataaaattgtagctgggtgcaaaatagcaact
aatcttgatttaaggcttcaaaacctcccgcaagtcgggaggacgctaaaacgcctcgcgacttagaataccggataagccact
atatctgatttgcttgctattgggcgcggtaatgattcctacgatgaaaataaaaacggcttgcttgactcgatgagtgcggtactt
ggataatacccgttcaggaatgataaggaaagacagccgattattgattggtactacatgctcgtaattaggatgggatattt
tacttgacaggacttatctattgagataaacaggcgcgactgcattagctgaacatgagatattgtcgtcgtctggacagaatta
cataccattgtcggtactttatattctcttattactggctcgaaaatgcctctgcctaaattacatgaggcgagttaaatatggcgatt
ctcaattaagccctactgagagcgaggattatactggtaagaatagtataacgcatatgactataaacaggattactagtaatta
tgattccggtgatattcttatttaacgccttatttcatcacacggtcggtatttcaaaccattaaatttaggtcagaagatgaaattaacta
aaatatatttgaaaagattctcgcgactagtatgcgattggatttgcatcagcatttacatatagttatataacccaacctaagcc
ggaggttaaaaaggtagtctctcagacctatgattagataaattcactattgactatctcagcgtcttaatctaagctatcgctatga
ttcaaggattctaagggaaaattaattaatagcgacgatttacagaagcaaggttattcactcacatatattgatttatgtactgatcc
attaaaaaaggtaattcaaatgaaatttgttaaattagtatatgtttgatgatgatcatcatatttgctcaggtgaaa
tgaataattcgcctctgcgcgattagtaacttggtattcaaagcaatcaggcgaatccgttattgatctcccgatgtaaaaggtact
gttactgtatattcatctgacgttaaacctgaaaatctacgcaatttattatactgattacgtgcaaataattagatatggtaggact
aaccatccattattcagaagtataatccaaacaatcaggattatattgatgaattgccatcatctgataatcaggaatatgatgataa
accgctccactggtggatattgaccgcaaaatgataatgttactcaaactataaaattaataacgttcgggcaaaggatttaata
cgagagtcgaattgatgtaaagtctaatacactaaatcctcaaatgtattatctattgacggctctaatctattagagttagtgctcct -continued

SEQUENCES

```
aaagatattttagataaccttcctcaattcctttcaactgttgatttgccaactgaccagatattgattgagggtttgatatttgaggttc
agcaaggtgatgctttagatttttcatttgctgctggctctcagcgtggcactgttgcaggcggtgttaatactgaccgcctcacctc
tgttttatcttctgctggtggttcgttcggtattttttaatggcgatgttttagggctatcagttcgcgcattaaagactaatagccattca
aaaatattgtctgtgccacgtattcttacgattcaggtcagaagggactatctctgaggccagaatgtcccattattactggtcgt
gtgactggtgaatctgccaatgtaaataatccatttcagacgattgagcgtcaaaatgtaggtataccatgagcgtattcctgagc
aatggctggcggtaatattgactggatattaccagcaaggccgatagatgagacttctactcaggcaagtgatgttattactaatc
aaagaagtattgctacaacggttaatttgcgtgatggacagactcattactcggtggcctcactgattataaaaacacactcagga
actggcgtaccgacctgtctaaaatcccataatcggcctcctgatagctcccgctctgattctaacgaggaaagcacgttatacg
tgctcgtcaaagcaaccatagtacgcgccctgtagcggcgcattaagcgcggcgggtgtggtggttacgcgcagcgtgaccg
ctacacttgccagcgccctagcgcccgctccatcgattcaccatcctactcgccacgttcgccggctaccccgtcaagctcta
aatcgggggctccattagggaccgatttagtgattacggcacctcgaccccaaaaaacttgatagggtgatggacacgtagt
gggccatcgccctgatagacggtattcgccattgacgaggagtccacgttattaatagtggactcttgaccaaactggaacaa
cactcaaccctatctcgggctattcattgatttataagggattagccgatttcgggactgcttaagtcgctccatatgctgaaatga
gctgagacaattaatcatccggctcgtataatgtgtggaattgtgagcggataacaatttcacaccccgggataaggaggacaat
tgatgcgtaaaggagaagaactatcactggagagtcccaattcttgagaattagatggtgatgttaatgggcacaaattactgtc
agtggagagggtgaaggtgatgcaacatacggaaaacttacccttaaatttatttgcactactggaaaactacctgaccgtggcc
aacacttgtcactactacggttatggtgacaatgctagcgagataccagatcacatgaaacagcatgactattcaagagtgcc
atgcccgaaggttacgtacaggaaagaactatattttcaaagatgacgggaactacaagacacgtgctgaagtcaagtttgaag
gtgatacccagttaatagaatcgagttaaaaggtattgatataaagaagatggaaacattcaggacacaaattggaatacaacta
taactcacacaatgtatacatcatggcagacaaacaaaagaatggaatcaaagtttaacttcaaaattagacacaacattgaagat
ggaagcgttcaactagcagaccattatcaacaaaatactccgattggcgatggccctgtccattaccagacaaccattacctgtc
cacacaatctgccattcgaaagatcccaacgaaaagagagaccacatggtccacttgagtagtaaccgctgctgggattacac
atggcatggatgaactatacaaataaggcgccagggagatatctatcgccctagggaccgtctcgagagaatcaatattaatcc
aacgcgtggcatcaaataaaacgaaaggctcagtcgaaagactgggccatcgattatctggatagtcggtgaacgctctcctg
agtaggacaaatccgccgccctagactattggttaaaaaatgagctgatttaacaaaaatttaatgcgaatataacaaaatattaac
gatacaatttaaatatttgcttatacaatcacctgatagggcattctgattatcaaccggggtacatatgattgacatgctagatt
acgattaccgttcatcgattctcttgatgctccagactctcaggcaatgacctgatagcattgtagatctctcaaaaatagctaccc
tctccggcattaatttatcagctagaacggagaatatcatattgatggtgatttgactgtctccggccatctcaccatttgaatatta
cctacacattactcaggcattgcatttaaaatatatgagggactaaaaatattatccagcgagaaataaaggatctcccgcaaa
agtattacagggtcataatgttttggtacaaccgatttagctttatgctctgaggcttt-
attgcttaattttgctaattctttgccttgcct
gtatgatttattggatgtt
```

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is to be deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

"Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

All references, patents and patent applications disclosed herein are incorporated by reference with respect to the subject matter for which each is cited, which in some cases may encompass the entirety of the document.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method of functionalizing endogenous *Escherichia coli* (*E. coli*) in a subject, the method comprising delivering to a subject having an inflammatory bowel disease, non-lytic recombinant Inoviridae M13 coliphage that
   are not comprised within a bacterial cell during delivery,
   infect viable nonpathogenic endogenous *E. coli* present in the subject, and
   are engineered to contain at least one nucleic acid comprising an inducible promoter operably linked to a nucleotide sequence that encodes an interleukin (IL), to produce viable nonpathogenic functionalized *E. coli* in the subject.

2. The method of claim 1, wherein the inflammatory bowel disease is Crohn's disease.

3. The method of claim 1, wherein the IL is IL-4.

4. The method of claim 1, wherein the inflammatory bowel disease is ulcerative colitis.

5. The method of claim 1, wherein the IL is IL-6.

6. The method of claim 1, wherein the IL is IL-10.

7. The method of claim 1, wherein the IL is IL-11.

8. The method of claim 1, wherein the IL is IL-13.

* * * * *

```
                         SEQUENCE LISTING

<160> NUMBER OF SEQ ID NOS: 9

<210> SEQ ID NO 1
<211> LENGTH: 6249
<212> TYPE: DNA
<213> ORGANISM: Artificial Sequence
<220> FEATURE:
<223> OTHER INFORMATION: Synthetic Polynucleotide

<400> SEQUENCE: 1
gacgtctgtg caagtactac tgttctgcag tcacttgaat tcaagaaacc aatagtccat      60
attgcatcag acattgccgt cactgcgtct tttactggct cttctcgcta accaaaccgg     120 taacccgct tattaaaagc attctgtaac aaagcgggac caaagccatg acaaaagcgc      180
gtaacaaaag tgtctataat cacggcagaa aagtccacat tgattatttg cacggcgtca     240
cactttgcta tgccatagca tttttatcca taagattagc ggatcatacc tgacgctttt     300
tatcgcaact ctctactgtt tctccataca gctgaaaagc ttacgggagg aacgttatga     360
atcagaccga cacatcacct atcaggctgc gcaggagctg gaacaccagc gagatagaag     420
cgctctttga cgagcatgcc ggacgtatcg atccgcgcat ttataccgat gaggatctgt     480
accaactcga actggagcgt gtcttcgccc ggtcctggct gctgttgggg catgaaaccc     540
agattcgcaa gccgggcgat tacatcacga cctacatggg tgaagaccct gtcgtggtcg     600
tccggcagaa agacgccagc attgccgtgt tcctgaacca gtgccgccac cgtggcatgc     660
gcatctgccg cgcggatgcc ggaaacgcga aggcgttcac ttgcagctac cacgggtggg     720
cttacgacac cgccggcaat cttgtcaatg tgccttacga ggccgaatcc ttcgcgtgcc     780
tgaacaagaa ggaatggagc ccgctgaagg cccgggtaga aacctacaag ggcctgattt     840
tcgccaactg ggatgagaac gctgtagacc tcgacacgta tctgggcgag gcgaagttct     900
acatggacca catgctcgac cgcaccgagg ccggcaccga agcgatcccg ggcgtgcaga     960
agtgggtcat tccctgtaac tggaaattcg ccgcagagca gttttgcagc gacatgtacc    1020
atgccgggac gacctcgcat ctgtctggca tcctggcagg cctgccagaa gaccttgaaa    1080
tggccgacct tgctccgccg acagttggca agcagtaccg tgcgtcatgg ggcggacatg    1140
gaagtggctt ctatgtcggc gaccccaatc tgatgcttgc catcatgggg ccaaaggtca    1200
```

```
ccagctactg gaccgaaggc cccgcgtcgg aaaaggcggc cgaacgtctg ggtagcgtgg      1260
agcgcggctc gaaactcatg gtcgagcaca tgaccgtctt ccccacgtgt tccttcctcc      1320
caggtatcaa tacggtccgg acatggcatc cgcgcgggcc gaacgaggtc gaggtatggg      1380
cgtttacggt ggtcgatgct gatgctcctg acgatatcaa ggaagagttc cggcgccaga      1440
cgctgcgcac cttctctgcc ggtggcgtgt tcgagcagga cgacggggag aactgggtcg      1500
agatccagca catcctgcga ggccacaagg cgcggagccg ccctttcaat gccgagatga      1560
gcatggacca gaccgtcgac aacgacccgg tttaccccgg gcggatcagc aacaacgtct      1620
acagcgagga agctgcccgc gggctctatg cccattggct gcggatgatg acatcccccg      1680
actgggacgc gctgaaggcg acacgctgaa tccagagaca gcttgcgcca cgcagtggcg      1740
ccggccagag gccgcatttg acttcgaccc aggttggatg cggtggacct tgtccatttg      1800
aaatctacaa ggaacgacca tgattgattc agccaacaga gccgacgtct ttctccgcaa      1860
gccggcaccc gtagcgcccg aactgcagca cgaagtcgag cagttctact attgggaggc      1920
caagcttctc aacgatcgcc gcttcgagga gtggttcgcg ctgctcgcgg aagacattca      1980
ctacttcatg cccattcgca ccacgcggat catgcgggac tcgcgccttg aatactcagg      2040
ctcccgagag tacgcgcact tcgatgacga cgccacgatg atgaagggac gcttgcgcaa      2100
gatcacgtcc gacgtgagct ggtccgagaa ccccgcatcg cggacccggc atctcgtgag      2160
caacgtgatg atcgtcggcg cagaggcaga aggggagtac gaaatctcaa gcgccttcat      2220
tgtgtaccgc aatcgtctgg agcggcagct cgacatcttt gccggtgagc gtcgcgatac      2280
gttgcgccgt aacacgagcg aggccgggtt cgagatcgtc aatcggacca tcctgatcga      2340
ccagagcacc atcctggcca ataacctcag tttcttcttc taggtgatgt catgacttgg      2400
acatacatat tgcggcaggg tgacctgcca cccggtgaga tgcagcgcta cgaaggcggc      2460
ccggaacctg tgatggtctg caacgtcgat ggcgagttct tcgcggtgca ggatacctgc      2520
acgcatgggg actgggcgtt gtcggatggt tacctggacg gtgatattgt cgaatgcacg      2580
ttgcatttcg gcaagttctg cgtgcggacc gggaaggtga aggcgctgcc tgcttgcaaa      2640
cctatcaagg tattcccaat caaggtcgaa ggcgatgaag tgcacgtcga tctcgacaac      2700
ggggagttga agtgatggct acccatgtgg cgatcatcgg caatggcgtg ggtggcttca      2760
cgaccgcgca ggccctacgt gccgagggct tcgaggggaa atctcgctg attggggacg       2820 aaccgcatct ccctatgac cgaccatcct tgtccaaggc ggttctcgac ggcagccttg       2880
agcggccgcc catactggcc gaggccgatt ggtacgcga ggcccgcatc gacatgctga       2940
ccggcccgga agtcactgcc cttgatgtgc agacaaggac gatcagtctg gatgatggca      3000
ccacgctctc tgcggacgcc atcgtcatcg cgacgggcag tcgagcgcgg acgatggcgt      3060
tgcccggcag ccaactgccg ggcgtcgtaa cgctgcgcac ctacggtgac gtgcaggtat      3120
tgcgcgatag ttggacttcc gcgacgcggc tgctgattgt gggtggcgga ttgatcggct      3180
gcgaggtcgc gacgacggcg cgcaagctcg gcctgtcggt cacgatcctg gaggcaggtg      3240
atgaactgct ggtccgagta cttgggcggc gtatcggtgc ctggctgcgc ggcctgctga      3300
cagaacttgg tgtgcaggtc gagttgggaa cgggtgtcgt aggttttct ggtgagggcc       3360 agctcgaaca agtcatggcc agcgatgggc gcagcttcgt agccgatagc gcactcatt       3420 gcgtcggcgc ggagcccgcg gatcaacttg cgcgtcaagc gggcttggca tgtgaccgcg      3480
gcgtcattgt cgatcactgc ggtgcgacgc ttgccaaagg cgtattcgcc gtcggagatg      3540
```

```
tggccagttg gccgctgcgc gccggcggcc ggcgttcgct cgaaacctat atgaacgcgc    3600
agcgccaagc cgccgcggtg gctgcggcca ttctggggaa aaacgtatcg gcaccgcaac    3660
tgcccgtgtc ctggacggag atcgctgggc atcgcatgca gatggcgggc gatatcgaag    3720
gacctggtga tttcgtctcg cgcggcatgc ccggtagtgg cgctgccctg ttgttccgcc    3780
tgcaggagcg aaggattcag gcggtcgtcg cggtcgatgc accccgtgac ttcgcgcttg    3840
caacccgatt ggtagaagcc cgcgcggcaa tcgagccagc acggctggca gatctttcaa    3900
acagtatgcg cgattttgtt cgtgcgaatg aaggagacct aacgtgaggt acccgagaat    3960
tggcttggac tcctgttgat agatccagta atgacctcag aactccatct ggatttgttc    4020
agaacgctcg gttgccgccg ggcgtttttt attggtgaga atccaagcag tagtcaggat    4080
cctcaagtcg gccgcccgtt ccatggatac tcgtcgacca ttacgctagc cgtctggagc    4140
tcggactgct aagtcgctcc catatgctcg ttcccgggac tacacaattg tcccccggcg    4200
ccagggttga tatctatcgc cctagggacc gtctcgagag aatcaatatt aatccaacgc    4260
gtggcatcaa ataaaacgaa aggctcagtc gaaagactgg gcctttcgtt ttatctgttg    4320
tttgtcggtg aacgctctcc tgagtaggac aaatccgccg ccctagactt aggcgttcgg    4380
ctgccggcag cggtatcagc tcactcaaag gcggtaatac ggttatccac agaatcaggg    4440
gataacgcag gaaagaacat gtgagcaaaa ggccagcaaa aggccaggaa ccgtaaaaag    4500
gccgcgttgc tggcgttttt ccataggctc cgcccccctg acgagcatca caaaaatcga    4560
cgctcaagtc agaggtggcg aaacccgaca ggactataaa gataccaggc gtttccccct    4620
ggaagctccc tcgtgcgctc tcctgttccg accctgccgc ttaccggata cctgtccgcc    4680
tttctccctt cgggaagcgt ggcgctttct catagctcac gctgtaggta tctcagttcg    4740
gtgtaggtcg ttcgctccaa gctgggctgt gtgcacgaac cccccgttca gcccgaccgc    4800
tgcgccttat ccggtaacta tcgtcttgag tccaacccgg taagacacga cttatcgcca    4860
ctggcagcag ccactggtaa caggattagc agagcgaggt atgtaggcgg tgctacagag    4920
ttcttgaagt ggtggcctaa ctacggctac actagaagga cagtatttgg tatctgcgct    4980
ctgctgaagc cagttacctt cggaaaaaga gttggtagct cttgatccgg caaacaaacc    5040
accgctggta gcggtggttt ttttgtttgc aagcagcaga ttacgcgcag aaaaaaagga    5100
tctcaagaag atcctttgat cttttctacg gggtctgacg ctcagtggaa cgaaaactca    5160
cgttaaggga ttttggtcat ggctagtgct tggattctca ccaataaaaa acgcccggcg    5220
gcaaccgagc gttctgaaca atccagatg gagttctgag gtcattactg gatctatcaa     5280
caggagtcca agccaattct cgaaccccag agtcccgctc agaagaactc gtcaagaagg    5340
cgatagaagg cgatgcgctg cgaatcggga gcggcgatac cgtaaagcac gaggaagcgg    5400
tcagcccatt cgccgccaag ctcttcagca atatcacggg tagccaacgc tatgtcctga    5460
tagcggtccg ccacacccag ccggccacag tcgatgaatc cagaaaagcg gccattttcc    5520
accatgatat tcggcaagca ggcatcgccg tgggtcacga cgagatcctc gccgtcgggc    5580
atacgcgcct tgagcctggc gaacagttcg gctggcgcga gccctgatg ctcttcgtcc    5640 agatcatcct gatcgacaag accggcttcc atccgagtac gtgctcgctc gatgcgatgt    5700
ttcgcttggt ggtcgaatgg gcaggtagcc ggatcaagcg tatgcagccg ccgcattgca    5760
tcagccatga tggatacttt ctcggcagga gcaaggtgag atgacaggag atcctgcccc    5820
ggcacttcgc ccaatagcag ccagtccctt cccgcttcag tgacaacgtc gagcacagcc    5880
gcgcaaggaa cgcccgtcgt ggccagccac gatagccgcg ctgcctcgtc ttgcagttca    5940
```

```
ttcagggcac cggacaggtc ggtcttgaca aaaagaaccg ggcgaccctg cgctgacagc    6000
cggaacacgg cggcatcaga gcagccgatt gtctgttgtg cccagtcata gccgaatagc    6060
ctctccaccc aagccgccgg agaacctgcg tgcaatccat cttgttcaat catgcgaaac    6120
gatcctcatc ctgtctcttg atcagatctt gatccctgc gccatcagat ccttggcggc    6180
aagaaagcca tccagtttac tttgcagggc ttcccaacct taccagaggg cggcccaact    6240
ggcaattcc                                                             6249

<210> SEQ ID NO 2
<211> LENGTH: 6037
<212> TYPE: DNA
<213> ORGANISM: Artificial Sequence
<220> FEATURE:
<223> OTHER INFORMATION: Synthetic Polynucleotide

<400> SEQUENCE: 2
gacgtctgtg caagtactac tgttctgcag tcacttgaat tctccctatc agtgatagag      60
attgacatcc ctatcagtga tagagatact gagcacatca gcaggacgca ctgacccagc     120
tgaaaagctt acgggaggaa cgttatgaat cagaccgaca catcacctat caggctgcgc     180
aggagctgga acaccagcga gatagaagcg ctctttgacg agcatgccgg acgtatcgat     240
ccgcgcattt ataccgatga ggatctgtac caactcgaac tggagcgtgt cttcgcccgg     300
tcctggctgc tgttggggca tgaaacccag attcgcaagc cgggcgatta catcacgacc     360
tacatgggtg aagaccctgt cgtggtcgtc cggcagaaag acgccagcat tgccgtgttc     420
ctgaaccagt gccgccaccg tggcatgcgc atctgccgcg cggatgccgg aaacgcgaag     480
gcgttcactt gcagctacca cgggtgggct tacgacaccg ccggcaatct tgtcaatgtg     540
ccttacgagg ccgaatcctt cgcgtgcctg aacaagaagg aatggagccc gctgaaggcc     600
cgggtagaaa cctacaaggg cctgattttc gccaactggg atgagaacgc tgtagacctc     660
gacacgtatc tgggcgaggc gaagttctac atggaccaca tgctcgaccg caccgaggcc     720
ggcaccgaag cgatcccggg cgtgcagaag tgggtcattc cctgtaactg gaaattcgcc     780
gcagagcagt tttgcagcga catgtaccat gccgggacga cctcgcatct gtctggcatc     840
ctggcaggcc tgccagaaga ccttgaaatg gccgaccttg ctccgccgac agttggcaag     900
cagtaccgtg cgtcatgggg cggacatgga agtggcttct atgtcggcga ccccaatctg     960
atgcttgcca tcatggggcc aaaggtcacc agctactgga ccgaaggccc cgcgtcggaa    1020
aaggcggccg aacgtctggg tagcgtggag cgcggctcga aactcatggt cgagcacatg    1080
accgtcttcc ccacgtgttc cttcctccca ggtatcaata cggtccggac atggcatccg    1140
cgcgggccga acgaggtcga ggtatgggcg tttacggtgg tcgatgctga tgctcctgac    1200
gatatcaagg aagagttccg gcgccagacg ctgcgcacct tctctgccgg tggcgtgttc    1260
gagcaggacg acgggagaa ctgggtcgag atccagcaca tcctgcgagg ccacaaggcg    1320
cggagccgcc ctttcaatgc cgagatgagc atggaccaga ccgtcgacaa cgacccggtt    1380 tacccccgggc ggatcagcaa caacgtctac agcgaggaag ctgccgcgcg gctctatgcc    1440
cattggctgc ggatgatgac atcccccgac tgggacgcg tgaaggcgac acgctgaatc    1500
cagagacagc ttgcgccacg cagtggcgcc ggccagaggc cgcatttgac ttcgacccag    1560
gttggatgcg gtggaccttg tccatttgaa atctacaagg aacgaccatg attgattcag    1620
ccaacagagc cgacgtcttt ctccgcaagc cggcacccgt agcgcccgaa ctgcagcacg    1680
```

-continued

```
aagtcgagca gttctactat tgggaggcca agcttctcaa cgatcgccgc ttcgaggagt      1740
ggttcgcgct gctcgcggaa gacattcact acttcatgcc cattcgcacc acgcggatca      1800
tgcgggactc gcgccttgaa tactcaggct cccgagagta cgcgcacttc gatgacgacg      1860
ccacgatgat gaagggacgc ttgcgcaaga tcacgtccga cgtgagctgg tccgagaacc      1920
ccgcatcgcg gacccggcat ctcgtgagca acgtgatgat cgtcggcgca gaggcagaag      1980
gggagtacga aatctcaagc gccttcattg tgtaccgcaa tcgtctggag cggcagctcg      2040
acatctttgc cggtgagcgt cgcgatacgt tgcgccgtaa cacgagcgag gccgggttcg      2100
agatcgtcaa tcggaccatc ctgatcgacc agagcaccat cctggccaat aacctcagtt      2160
tcttcttcta ggtgatgtca tgacttggac atacatattg cggcagggtg acctgccacc      2220
cggtgagatg cagcgctacg aaggcggccc ggaacctgtg atggtctgca acgtcgatgg      2280
cgagttcttc gcggtgcagg atacctgcac gcatgggac tgggcgttgt cggatggtta      2340
cctggacggt gatattgtcg aatgcacgtt gcatttcggc aagttctgcg tgcggaccgg      2400
gaaggtgaag gcgctgcctg cttgcaaacc tatcaaggta ttcccaatca aggtcgaagg      2460
cgatgaagtg cacgtcgatc tcgacaacgg ggagttgaag tgatggctac ccatgtggcg      2520
atcatcggca atggcgtggg tggcttcacg accgcgcagg ccctacgtgc cgagggcttc      2580
gaggggagaa tctcgctgat tggggacgaa ccgcatctcc cctatgaccg accatccttg      2640
tccaaggcgg ttctcgacgg cagccttgag cggccgccca tactggccga ggccgattgg      2700
tacggcgagg cccgcatcga catgctgacc ggcccggaag tcactgccct tgatgtgcag      2760
acaaggacga tcagtctgga tgatggcacc acgctctctg cggacgccat cgtcatcgcg      2820
acgggcagtc gagcgcggac gatggcgttg cccggcagcc aactgccggg cgtcgtaacg      2880
ctgcgcacct acggtgacgt gcaggtattg cgcgatagtt ggacttccgc gacgcggctg      2940
ctgattgtgg gtggcggatt gatcggctgc gaggtcgcga cgacggcgcg caagctcggc      3000
ctgtcggtca cgatcctgga ggcaggtgat gaactgctgg tccgagtact tgggcggcgt      3060
atcggtgcct ggctgcgcgg cctgctgaca gaacttggtg tgcaggtcga gttgggaacg      3120
ggtgtcgtag gttttctctgg tgagggccag ctcgaacaag tcatggccag cgatgggcgc      3180
agcttcgtag ccgatagcgc actcattttgc gtcggcgcgg agcccgcgga tcaacttgcg      3240
cgtcaagcgg gcttggcatg tgaccgcggc gtcattgtcg atcactgcgg tgcgacgctt      3300
gccaaaggcg tattcgccgt cggagatgtg gccagttggc cgctgcgcgc cggcggccgg      3360
cgttcgctcg aaacctatat gaacgcgcag cgccaagccg ccgcggtggc tgcggccatt      3420
ctggggaaaa acgtatcggc accgcaactg cccgtgtcct ggacggagat cgctgggcat      3480
cgcatgcaga tggcgggcga tatcgaagga cctggtgatt tcgtctcgcg cggcatgccc      3540
ggtagtggcg ctgccctgtt gttccgcctg caggagcgaa ggattcaggc ggtcgtcgcg      3600
gtcgatgcac cccgtgactt cgcgcttgca acccgattgg tagaagcccg cgcggcaatc      3660
gagccagcac ggctggcaga tctttcaaac agtatgcgcg attttgttcg tgcgaatgaa      3720
ggagacctaa cgtgaggtac ccgagaattg gcttggactc ctgttgatag atccagtaat      3780
gacctcagaa ctccatctgg atttgttcag aacgctcggt tgccgccggg cgttttttat      3840
tggtgagaat ccaagcagta gtcaggatcc tcaagtcggc cgcccgttcc atggatactc      3900
gtcgaccatt acgctagccg tctggagctc ggactgctta agtcgctcca tatgctcgtt      3960
cccgggacta cacaattgtc ccccggcgcc agggttgata tctatcgccc tagggaccgt      4020
ctcgagagaa tcaatattaa tccaacgcgt ggcatcaaat aaaacgaaag gctcagtcga      4080
```

```
aagactgggc ctttcgtttt atctgttgtt tgtcggtgaa cgctctcctg agtaggacaa    4140
atccgccgcc ctagacttag gcgttcggct gcggcgagcg gtatcagctc actcaaaggc    4200
ggtaatacgg ttatccacag aatcagggga taacgcagga agaacatgt gagcaaaagg     4260 ccagcaaaag gccaggaacc gtaaaaaggc cgcgttgctg gcgttttttcc ataggctccg   4320 ccccccctgac gagcatcaca aaaatcgacg ctcaagtcag aggtggcgaa acccgacagg   4380
actataaaga taccaggcgt ttccccctgg aagctccctc gtgcgctctc ctgttccgac    4440
cctgccgctt accggatacc tgtccgcctt ctcccttcg ggaagcgtgg cgctttctca     4500
tagctcacgc tgtaggtatc tcagttcggt gtaggtcgtt cgctccaagc tgggctgtgt   4560
gcacgaaccc cccgttcagc ccgaccgctg cgccttatcc ggtaactatc gtcttgagtc   4620
caacccggta agacacgact tatcgccact ggcagcagcc actggtaaca ggattagcag   4680
agcgaggtat gtaggcggtg ctacagagtt cttgaagtgg tggcctaact acggctacac   4740
tagaaggaca gtatttggta tctgcgctct gctgaagcca gttaccttcg gaaaaagagt   4800
tggtagctct tgatccggca aacaaaccac cgctggtagc ggtggttttt tgtttgcaa    4860 gcagcagatt acgcgcagaa aaaaaggatc tcaagaagat cctttgatct tttctacggg   4920
gtctgacgct cagtggaacg aaaactcacg ttaagggatt ttggtcatgg ctagtgcttg   4980
gattctcacc aataaaaaac gcccggcggc aaccgagcgt tctgaacaaa tccagatgga   5040
gttctgaggt cattactgga tctatcaaca ggagtccaag ccaattctcg aaccccagag   5100
tcccgctcag aagaactcgt caagaaggcg atagaaggcg atgcgctgcg aatcgggagc   5160
ggcgataccg taaagcacga ggaagcggtc agcccattcg ccgccaagct cttcagcaat   5220
atcacgggta gccaacgcta tgtcctgata gcggtccgcc acacccagcc ggccacagtc   5280
gatgaatcca gaaaagcggc cattttccac catgatattc ggcaagcagg catcgccgtg   5340
ggtcacgacg agatcctcgc cgtcgggcat acgcgcttg agcctggcga acagttcggc    5400
tggcgcgagc ccctgatgct cttcgtccag atcatcctga tcgacaagac cggcttccat   5460
ccgagtacgt gctcgctcga tgcgatgttt cgcttggtgg tcgaatgggc aggtagccgg   5520
atcaagcgta tgcagccgcc gcattgcatc agccatgatg gatactttct cggcaggagc   5580
aaggtgagat gacaggagat cctgccccgg cacttcgccc aatagcagcc agtcccttcc   5640
cgcttcagtg acaacgtcga gcacagccgc gcaaggaacg cccgtcgtgg ccagccacga   5700
tagccgcgct gcctcgtctt gcagttcatt cagggcaccg gacaggtcgg tcttgacaaa   5760
aagaaccggg cgaccctgcg ctgacagccg gaacacggcg gcatcagagc agccgattgt   5820
ctgttgtgcc cagtcatagc cgaatagcct ctccacccaa gcggccggag aacctgcgtg   5880
caatccatct tgttcaatca tgcgaaacga tcctcatcct gtctcttgat cagatcttga   5940 tccctgcgc catcagatcc ttggcggcaa gaaagccatc cagtttactt tgcagggctt    6000
cccaacctta ccagagggcg gcccaactgg caattcc                            6037
```

<210> SEQ ID NO 3
<211> LENGTH: 4497
<212> TYPE: DNA
<213> ORGANISM: Artificial Sequence
<220> FEATURE:
<223> OTHER INFORMATION: Synthetic Polynucleotide

<400> SEQUENCE: 3

```
gacgtctgtg caagtactaa gaaaccaata gtccatattg catcagacat tgccgtcact    60
```

| | |
|---|---|
| gcgtcttta ctggctcttc tcgctaacca aaccggtaac cccgcttatt aaaagcattc | 120 |
| tgtaacaaag cgggaccaaa gccatgacaa aagcgcgtaa caaaagtgtc tataatcacg | 180 |
| gcagaaaagt ccacattgat tatttgcacg gcgtcacact ttgctatgcc atagcatttt | 240 |
| tatccataag attagcggat catacctgac gcttttatc gcaactctct actgtttctc | 300 |
| catacagctg aaggattaag gaggtagcat gcatgaaaaa gcgtatcggt attgttggtg | 360 |
| caggcactgc cggcctccat cttggcctct tcctccgcca gcatgacgtc gacgtcactg | 420 |
| tgtacactga tcgtaagccc gatgagtaca gtggactgcg gctcctgaat accgttgctc | 480 |
| acaacgcggt gacggtgcag cgggaggttg ccctcgacgt caatgagtgg ccgtctgagg | 540 |
| agtttggcta tttcggccac tactactacg taggtgggcc gcagcccatg cgtttctacg | 600 |
| gtgatctcaa ggctcccagc cgtgcagtgg actaccgtct ctacctgccg atgctgatgc | 660 |
| gtgcactgga agccagggc ggcaagttct gctacgacgc cgtgtctgcc gaagatctgg | 720 |
| aagggctgtc ggagcagtat gatctgctgg ttgtgtgcac tggtaaatac gccctcggca | 780 |
| aggtgttcga gaagcagtcc gaaaactcgc ccttcgagaa gccgcaacgg gcactgtgcg | 840 |
| ttggtctctt caagggcatc aaggaagcac cgattcgcgc ggtgactatg tccttctcgc | 900 |
| cagggcatgg cgagctgatt gagattccaa ccctgtcgtt caatggcatg agcacagcgc | 960 |
| tggtgctcga aaaccatatt ggtagcgatc tggaagtcct cgcccacacc aagtatgacg | 1020 |
| atgacccgcg tgcgttcctc gatctgatgc tggagaagct gcgtaagcat catccttccg | 1080 |
| ttgccgagcg catcgatccg gctgagttcg acctggccaa cagttctctg gacatcctcc | 1140 |
| agggcggtgt tgtgccagta ttccgcgacg gtcatgcgac cctcaataac ggcaaaacca | 1200 |
| tcatcgggct gggcgacatc caggcaactg tcgatccggt cttgggccag ggcgcgaaca | 1260 |
| tggcgtccta tgcggcatgg attctgggcg aggaaatcct tgcgcactct gtctacgacc | 1320 |
| tgcgcttcag cgaacacctg gagcgtcgcc gccaggatcg cgtgctgtgc gccacccgct | 1380 |
| ggaccaactt cactctgagc gccttcacgg aacttccgcc ggaattcctc accttccttc | 1440 |
| agatcctgag ccagagccgt gaaatggctg atgagttcac ggacaacttc aactatccgg | 1500 |
| aacttcagtg ggatcgcttc tccagcccgg aacgtatcgg tcagtggtgc agccagtacg | 1560 |
| cacccactat tgcggcctga cgctattgct ccgctggtca aggccagcgg agccctaact | 1620 |
| cctgggtgat tcaaatgacg ttaaaaaaag atgtggtggt ggatatcgac tccaccagct | 1680 |
| tccgccaggc ggttgcactg ttcgcgacgg gaattgcggt tctcagcgcg gagactgacg | 1740 |
| agggcgaagt gcatggcatg acggtgaaca gcttcacctc catcagtctg gacccgccga | 1800 |
| ctgtgatggt gtccctgaag tcgggccgta tgcatgagct gctgactcaa ggcggacgct | 1860 |
| tcggcgtcag cctcctgggt gaaagtcaga agatgttatc ggcattcttc agcaagcgtg | 1920 |
| tgatcgatgg cactcctcct cctgctttca cagttcaggc cggcctcccc actctgcggg | 1980 |
| acgccatggc ctggttcgaa tgcgaggtgg agagcacggt tgaagtacac gaccacacgc | 2040 |
| tcttcattgc gcgcgttagc gcctgtggag tgccggaggc gaatgccccc cagccgctgc | 2100 |
| tgttctttgc cagccgttat cacggcaacc cgttgccgct gaattgaaac gttcgagaat | 2160 |
| tggcttggac tcctgttgat agatccagta atgacctcag aactccatct ggatttgttc | 2220 |
| agaacgctcg gttgccgccg ggcgtttttt attggtgaga atccaagcag tagtcaaagc | 2280 |
| ttccgcaagg taccactttg ccgcggagta tttgtacatt tgaaggatcc tcaagtcggc | 2340 |
| cgcccgttcc atggatactc gtcgaccatt acgctagccg tctggagctc ggactgctta | 2400 |
| agtcgctcca tatgctcgtt cccgggacta cacaattgtc cccggcgcc agggttgata | 2460 |

```
tctatcgccc tagggaccgt ctcgagagaa tcaatattaa tccaacgcgt ggcatcaaat    2520
aaaacgaaag gctcagtcga aagactgggc ctttcgtttt atctgttgtt tgtcggtgaa    2580
cgctctcctg agtaggacaa atccgccgcc ctagacttag gcgttcggct gcggcgagcg    2640
gtatcagctc actcaaaggc ggtaatacgg ttatccacag aatcagggga taacgcagga    2700
aagaacatgt gagcaaaagg ccagcaaaag gccaggaacc gtaaaaaggc cgcgttgctg    2760
gcgttttttcc ataggctccg cccccctgac gagcatcaca aaaatcgacg ctcaagtcag    2820
aggtggcgaa acccgacagg actataaaga taccaggcgt ttccccctgg aagctccctc    2880
gtgcgctctc ctgttccgac cctgccgctt accggatacc tgtccgcctt ctcccttcg    2940
ggaagcgtgg cgctttctca tagctcacgc tgtaggtatc tcagttcggt gtaggtcgtt    3000
cgctccaagc tgggctgtct gcacgaaccc cccgttcagc ccgaccgctg cgccttatcc    3060
ggtaactatc gtcttgagtc caacccggta agacacgact tatcgccact ggcagcagcc    3120
actggtaaca ggattagcag agcgaggtat gtaggcggtg ctacagagtt cttgaagtgg    3180
tggcctaact acggctacac tagaaggaca gtatttggta tctgcgctct gctgaagcca    3240
gttaccttcg gaaaaagagt tggtagctct tgatccggca acaaaccac cgctggtagc    3300
ggtggttttt ttgtttgcaa gcagcagatt acgcgcagaa aaaaggatc tcaagaagat    3360
cctttgatct tttctacggg gtctgacgct cagtggaacg aaaactcacg ttaagggatt    3420
ttggtcatgg ctagtgcttg gattctcacc aataaaaaac gcccggcggc aaccgagcgt    3480
tctgaacaaa tccagatgga gttctgaggt cattactgga tctatcaaca ggagtccaag    3540
ccaattctcg aaccccagag tcccgctcag aagaactcgt caagaaggcg atagaaggcg    3600
atgcgctgcg aatcgggagc ggcgataccg taaagcacga ggaagcggtc agcccattcg    3660
ccgccaagct cttcagcaat atcacgggta gccaacgcta tgtcctgata gcggtccgcc    3720
acacccagcc ggccacagtc gatgaatcca gaaaagcggc cattttccac catgatattc    3780
ggcaagcagg catcgccgtg gtcacgacg agatcctcgc cgtcgggcat acgcgccttg    3840
agcctggcga acagttcggc tggcgcgagc ccctgatgct cttcgtccag atcatcctga    3900
tcgacaagac cggcttccat ccgagtacgt gctcgctcga tgcgatgttt cgcttggtgg    3960
tcgaatgggc aggtagccgg atcaagcgta tgcagccgcc gcattgcatc agccatgatg    4020
gatactttct cggcaggagc aaggtgagat gacaggagat cctgccccgg cacttcgccc    4080
aatagcagcc agtcccttcc cgcttcagtg acaacgtcga gcacagccgc gcaaggaacg    4140
cccgtcgtgg ccagccacga tagccgcgct gcctcgtctt gcagttcatt cagggcaccg    4200
gacaggtcgg tcttgacaaa aagaaccggg cgaccctgcg ctgacagccg gaacacggcg    4260
gcatcagagc agccgattgt ctgttgtgcc cagtcatagc cgaatagcct ctccacccaa    4320
gccgccggag aacctgcgtg caatccatct tgttcaatca tgcgaaacga tcctcatcct    4380
gtctcttgat cagatcttga tcccctgcgc catcagatcc ttggcggcaa gaaagccatc    4440
cagtttactt tgcagggctt cccaacctta ccagagggcg gcccaactgg caattcc        4497
```

<210> SEQ ID NO 4
<211> LENGTH: 4285
<212> TYPE: DNA
<213> ORGANISM: Artificial Sequence
<220> FEATURE:
<223> OTHER INFORMATION: Synthetic Polynucleotide

<400> SEQUENCE: 4

| | |
|---|---|
| gacgtctgtg caagtacttc cctatcagtg atagagattg acatccctat cagtgataga | 60 |
| gatactgagc acatcagcag gacgcactga cccagctgaa ggattaagga ggtagcatgc | 120 |
| atgaaaaagc gtatcggtat tgttggtgca ggcactgccg gcctccatct tggcctcttc | 180 |
| ctccgccagc atgacgtcga cgtcactgtg tacactgatc gtaagcccga tgagtacagt | 240 |
| ggactgcggc tcctgaatac cgttgctcac aacgcggtga cggtgcagcg ggaggttgcc | 300 |
| ctcgacgtca atgagtggcc gtctgaggag tttggctatt tcggccacta ctactacgta | 360 |
| ggtgggccgc agcccatgcg tttctacggt gatctcaagg ctcccagccg tgcagtggac | 420 |
| taccgtctct acctgccgat gctgatgcgt gcactggaag ccaggggcgg caagttctgc | 480 |
| tacgacgccg tgtctgccga agatctggaa gggctgtcgg agcagtatga tctgctggtt | 540 |
| gtgtgcactg gtaaatacgc cctcggcaag gtgttcgaga agcagtccga aaactcgccc | 600 |
| ttcgagaagc cgcaacgggc actgtgcgtt ggtctcttca agggcatcaa ggaagcaccg | 660 |
| attcgcgcgg tgactatgtc cttctcgcca gggcatggcg agctgattga gattccaacc | 720 |
| ctgtcgttca atggcatgag cacagcgctg gtgctcgaaa accatattgg tagcgatctg | 780 |
| gaagtcctcg cccacaccaa gtatgacgat gacccgcgtg cgttcctcga tctgatgctg | 840 |
| gagaagctgc gtaagcatca tccttccgtt gccgagcgca tcgatccggc tgagttcgac | 900 |
| ctggccaaca gttctctgga catcctccag ggcggtgttg tgccagtatt ccgcgacggt | 960 |
| catgcgaccc tcaataacgg caaaaccatc atcgggctgg cgacatcca ggcaactgtc | 1020 |
| gatccggtct tgggccaggg cgcgaacatg gcgtcctatg cggcatggat tctgggcgag | 1080 |
| gaaatccttg cgcactctgt ctacgacctg cgcttcagcg aacacctgga gcgtcgccgc | 1140 |
| caggatcgcg tgctgtgcgc cacccgctgg accaacttca ctctgagcgc cttcacggaa | 1200 |
| cttccgccgg aattcctcac cttccttcag atcctgagcc agagccgtga atggctgat | 1260 |
| gagttcacgg acaacttcaa ctatccggaa cttcagtggg atcgcttctc cagcccggaa | 1320 |
| cgtatcggtc agtggtgcag ccagtacgca cccactattg cggcctgacg ctattgctcc | 1380 |
| gctggtcaag gccagcggag ccctaactcc tgggtgattc aaatgacgtt aaaaaaagat | 1440 |
| gtggtggtga atatcgactc caccagcttc cgccaggcgg ttgcactgtt cgcgacggga | 1500 |
| attgcggttc tcagcgcgga gactgacgag ggcgaagtgc atggcatgac ggtgaacagc | 1560 |
| ttcacctcca tcagtctgga cccgccgact gtgatggtgt ccctgaagtc gggccgtatg | 1620 |
| catgagctgc tgactcaagg cggacgcttc ggcgtcagcc tcctgggtga agtcagaag | 1680 |
| atgttatcgg cattcttcag caagcgtgtg atcgatggca ctcctcctcc tgctttcaca | 1740 |
| gttcaggccg gcctccccac tctgcgggac gccatggcct ggttcgaatg cgaggtggag | 1800 |
| agcacggttg aagtacacga ccacacgctc ttcattgcgc gcgttagcgc ctgtggagtg | 1860 |
| ccggaggcga atgccccca gccgctgctg ttctttgcca gccgttatca cggcaacccg | 1920 |
| ttgccgctga attgaaacgt tcgagaattg gcttggactc tgttgatag atccagtaat | 1980 |
| gacctcagaa ctccatctgg atttgttcag aacgctcggt tgccgccggg cgttttttat | 2040 |
| tggtgagaat ccaagcagta gtcaaagctt ccgcaaggta ccactttgcc gcggagtatt | 2100 |
| tgtacatttg aaggatcctc aagtcggccg cccgttccat ggatactcgt cgaccattac | 2160 |
| gctagccgtc tggagctcgg actgcttaag tcgctccata tgctcgttcc cgggactaca | 2220 |
| caattgtccc ccggcgccag ggttgatatc tatcgcccta gggaccgtct cgagagaatc | 2280 |
| aatattaatc caacgcgtgg catcaaataa aacgaaaggc tcagtcgaaa gactgggcct | 2340 |
| ttcgtttat ctgttgtttg tcggtgaacg ctctcctgag taggacaaat ccgccgccct | 2400 |

```
agacttaggc gttcggctgc ggcgagcggt atcagctcac tcaaaggcgg taatacggtt    2460
atccacagaa tcaggggata acgcaggaaa gaacatgtga gcaaaaggcc agcaaaaggc    2520
caggaaccgt aaaaaggccg cgttgctggc gttttttccat aggctccgcc cccctgacga   2580
gcatcacaaa aatcgacgct caagtcagag gtggcgaaac ccgacaggac tataaagata    2640
ccaggcgttt ccccctggaa gctccctcgt gcgctctcct gttccgaccc tgccgcttac    2700
cggatacctg tccgcctttc tcccttcggg aagcgtggcg ctttctcata gctcacgctg    2760
taggtatctc agttcggtgt aggtcgttcg ctccaagctg ggctgtctgc acgaaccccc    2820
cgttcagccc gaccgctgcg ccttatccgg taactatcgt cttgagtcca acccggtaag    2880
acacgactta tcgccactgg cagcagccac tggtaacagg attagcagag cgaggtatgt    2940
aggcggtgct acagagttct tgaagtggtg gcctaactac ggctacacta aggacagt     3000 atttggtatc tgcgctctgc tgaagccagt taccttcgga aaaagagttg gtagctcttg    3060
atccggcaaa caaaccaccg ctggtagcgg tggttttttt gtttgcaagc agcagattac    3120
gcgcagaaaa aaaggatctc aagaagatcc tttgatcttt tctacggggt ctgacgctca    3180
gtggaacgaa aactcacgtt aagggatttt ggtcatggct agtgcttgga ttctcaccaa    3240
taaaaaacgc ccgcggcaa ccgagcgttc tgaacaaatc cagatggagt tctgaggtca    3300
ttactggatc tatcaacagg agtccaagcc aattctcgaa ccccagagtc ccgctcagaa    3360
gaactcgtca agaaggcgat agaaggcgat gcgctgcgaa tcgggagcgg cgataccgta    3420
aagcacgagg aagcggtcag cccattcgcc gccaagctct tcagcaatat cacgggtagc    3480
caacgctatg tcctgatagc ggtccgccac acccagccgg ccacagtcga tgaatccaga    3540
aaagcggcca ttttccacca tgatattcgg caagcaggca tcgccgtggg tcacgacgag    3600
atcctcgccg tcgggcatac gcgccttgag cctggcgaac agttcggctg gcgcgagccc    3660
ctgatgctct tcgtccagat catcctgatc gacaagaccg gcttccatcc gagtacgtgc    3720
tcgctcgatg cgatgtttcg cttggtggtc gaatgggcag gtagccggat caagcgtatg    3780
cagccgccgc attgcatcag ccatgatgga tactttctcg gcaggagcaa ggtgagatga    3840
caggagatcc tgccccggca cttcgcccaa tagcagccag tcccttcccg cttcagtgac    3900
aacgtcgagc acagccgcgc aaggaacgcc cgtcgtggcc agccacgata gccgcgctgc    3960
ctcgtcttgc agttcattca gggcaccgga caggtcggtc ttgacaaaaa gaaccgggcg    4020
accctgcgct gacagccgga acacggcggc atcagagcag ccgattgtct gttgtgccca    4080
gtcatagccg aatagcctct ccacccaagc ggccggagaa cctgcgtgca atccatcttg    4140
ttcaatcatg cgaaacgatc ctcatcctgt ctcttgatca gatcttgatc ccctgcgcca    4200
tcagatcctt ggcggcaaga aagccatcca gtttactttg cagggcttcc caaccttacc    4260
agagggcggc ccaactggca attcc                                          4285
```

<210> SEQ ID NO 5
<211> LENGTH: 9507
<212> TYPE: DNA
<213> ORGANISM: Artificial Sequence
<220> FEATURE:
<223> OTHER INFORMATION: Synthetic Polynucleotide

<400> SEQUENCE: 5

```
aatgctacta ctattagtag aattgatgcc acctttcag ctcgcgcccc aaatgaaaat    60
atagctaaac aggttattga ccatttgcga atgtatctta atggtcaaac taaatctact   120
```

```
cgttcgcaga attgggaatc aactgttata tggaatgaaa cttccagaca ccgtacttta    180
gttgcatatt taaaacatgt tgagctacag cattatattc agcaattaag ctctaagcca    240
tccgcaaaaa tgacctctta tcaaaaggag caattaaagg tactctctaa tcctgacctg    300
ttggagtttg cttccggtct ggttcgcttt gaagctcgaa ttaaaacgcg atatttgaag    360
tctttcgggc ttcctcttaa tcttttgat gcaatccgct ttgcttctga ctataatagt     420
cagggtaaag acctgatttt tgatttatgg tcattctcgt tttctgaact gtttaaagca    480
tttgagggg attcaatgaa tatttatgac gattccgcag tattggacgc tatccagtct     540
aaacatttta ctattacccc ctctggcaaa acttcttttg caaaagcctc tcgctatttt    600
ggtttttatc gtcgtctggt aaacgagggt tatgatagtt ttgctcttac tatgcctcgt    660
aattcctttt ggcgttatgt atctgcatta gttgaatgtg gtattcctaa atctcaactg    720
atgaatcttt ctacctgtaa taatgttgtt ccgttagttc gttttattaa cgtagatttt    780
tcttcccaac gtcctgactg gtataatgag ccagttctta aaatcgcata aggtaattca    840
caatgattaa agttgaaatt aaaccatctc aagcccaatt tactactcgt tctggtgttt    900
ctcgtcaggg caagccttat tcactgaatg agcagctttg ttacgttgat ttgggtaatg    960
aatatccggt tcttgtcaag attactcttg atgaaggtca gccagcctat gcgcctggtc   1020
tgtacaccgt tcatctgtcc tcttttcaaag ttggtcagtt cggttccctt atgattgacc   1080
gtctgcgcct cgttccggct aagtaacatg gagcaggtcg cggatttcga cacaatttat   1140
caggcgatga tacaaatctc cgttgtactt tgtttcgcgc ttggtataat cgctgggggt   1200
caaagatgag tgttttagtg tattcttttg cctctttcgt tttaggttgg tgccttcgta   1260
gtggcattac gtattttacc cgtttaatgg aaacttcctc atgaaaaagt ctttagtcct   1320
caaagcctct gtagccgttg ctaccctcgt tccgatgctg tctttcgctg ctgagggtga   1380
cgatcccgca aaagcggcct ttaactcect gcaagcctca gcgaccgaat atatcggtta   1440
tgcgtgggcg atggttgttg tcattgtcgg cgcaactatc ggtatcaagc tgtttaagaa   1500
attcacctcg aaagcaagct gataaaccga tacaattaaa ggctcctttt ggagcctttt   1560
ttttggagat tttcaacgtg aaaaaattat tattcgcaat tcctttagtt gttcctttct   1620
attctcactc cgctgaaact gttgaaagtt gtttagcaaa atcccataca gaaaattcat   1680
ttactaacgt ctggaaagac gacaaaaactt tagatcgtta cgctaactat gagggctgtc   1740
tgtggaatgc tacaggcgtt gtagtttgta ctggtgacga aactcagtgt tacggtacat   1800
gggttcctat tgggcttgct atccctgaaa atgagggtgg tggctctgag ggtggcggtt   1860
ctgagggtgg cggttctgag ggtggcggta ctaaacctcc tgagtacggt gatacaccta   1920
ttccgggcta tacttatatc aaccctctcg acggcactta ccgcctggt actgagcaaa   1980
accccgctaa tcctaatcct tctcttgagg agtctcagcc tcttaatact ttcatgtttc   2040
agaataatag gttccgaaat aggcaggggg cattaactgt ttatacgggc actgttactc   2100
aaggcactga cccgttaaa acttattacc agtacactcc tgtatcatca aaagccatgt   2160
atgacgctta ctggaacggt aaattcagag actgcgcttt ccattctggc tttaatgagg   2220
atttatttgt ttgtgaatat caaggccaat cgtctgacct gcctcaacct cctgtcaatg   2280
ctggcggcgg ctctggtggt ggttctggtg gcggctctga gggtggtggc tctgagggtg   2340
gcggttctga gggtggcggc tctgaggag gcggttccgg tggtggctct ggttccggtg   2400
attttgatta tgaaaagatg gcaacgcta ataaggggc tatgaccgaa aatgccgatg     2460
aaaacgcgct acagtctgac gctaaaggca aacttgattc tgtcgctact gattacggtg   2520
```

```
ctgctatcga tggtttcatt ggtgacgttt ccggccttgc taatggtaat ggtgctactg      2580
gtgattttgc tggctctaat tcccaaatgg ctcaagtcgg tgacggtgat aattcacctt      2640
taatgaataa tttccgtcaa tatttacctt ccctccctca atcggttgaa tgtcgccctt      2700
ttgtctttgg cgctggtaaa ccatatgaat tttctattga ttgtgacaaa ataaacttat      2760
tccgtggtgt ctttgcgttt cttttatatg ttgccacctt tatgtatgta ttttctacgt      2820
ttgctaacat actgcgtaat aaggagtctt aatcatgcca gttcttttgg gtattccgtt      2880
attattgcgt ttcctcggtt tccttctggt aactttgttc ggctatctgc ttacttttct      2940
taaaaagggc ttcggtaaga tagctattgc tatttcattg tttcttgctc ttattattgg      3000
gcttaactca attcttgtgg gttatctctc tgatattagc gctcaattac cctctgactt      3060
tgttcagggt gttcagttaa ttctcccgtc taatgcgctt ccctgttttt atgttattct      3120
ctctgtaaag gctgctattt tcatttttga cgttaaacaa aaaatcgttt cttatttgga      3180
ttgggataaa taatatggct gtttattttg taactggcaa attaggctct ggaaagacgc      3240
tcgttagcgt tggtaagatt caggataaaa ttgtagctgg gtgcaaaata gcaactaatc      3300
ttgatttaag gcttcaaaac ctcccgcaag tcgggaggtt cgctaaaacg cctcgcgttc      3360
ttagaatacc ggataagcct tctatatctg atttgcttgc tattgggcgc ggtaatgatt      3420
cctacgatga aaataaaaac ggcttgcttg ttctcgatga gtgcggtact tggtttaata      3480
cccgttcttg gaatgataag gaaagacagc cgattattga ttggtttcta catgctcgta      3540
aattaggatg ggatattatt tttcttgttc aggacttatc tattgttgat aaacaggcgc      3600
gttctgcatt agctgaacat gttgtttatt gtcgtcgtct ggacagaatt actttacctt      3660
ttgtcggtac tttatattct cttattactg gctcgaaaat gcctctgcct aaattacatg      3720
ttggcgttgt aaatatggc gattctcaat taagccctac tgttgagcgt tggctttata      3780
ctggtaagaa tttgtataac gcatatgata ctaaacaggc ttttttctagt aattatgatt      3840 ccggtgttta ttcttatttta acgccttatt tatcacacgg tcggtatttc aaaccattaa      3900
atttaggtca gaagatgaaa ttaactaaaa tatatttgaa aaagttttct cgcgttcttt      3960
gtcttgcgat tggatttgca tcagcattta catatagtta tataacccaa cctaagccgg      4020
aggttaaaaa ggtagtctct cagacctatg attttgataa attcactatt gactcttctc      4080
agcgtcttaa tctaagctat cgctatgttt tcaaggattc taagggaaaa ttaattaata      4140
gcgacgattt acagaagcaa ggttattcac tcacatatat tgatttatgt actgtttcca      4200
ttaaaaaagg taattcaaat gaaattgtta atgtaattaa ttttgttttt cttgatgttt      4260
gtttcatcat cttcttttgc tcaggtaatt gaaatgaata attcgcctct gcgcgatttt      4320
gtaacttggt attcaaagca atcaggcgaa tccgttattg tttctcccga tgtaaaaggt      4380
actgttactg tatattcatc tgacgttaaa cctgaaaatc tacgcaattt ctttatttct      4440
gttttacgtg caaataattt tgatatggta ggttctaacc cttccattat tcagaagtat      4500
aatccaaaca atcaggatta tattgatgaa ttgccatcat ctgataatca ggaatatgat      4560
gataattccg ctccttctgg tggtttcttt gttccgcaaa atgataatgt tactcaaact      4620
tttaaaatta ataacgttcg ggcaaaggat ttaatacgag ttgtcgaatt gtttgtaaag      4680
tctaatactt ctaaatcctc aaatgtatta tctattgacg gctctaatct attagttgtt      4740
agtgctccta agatatttt agataacctt cctcaattcc tttcaactgt tgatttgcca      4800
actgaccaga tattgattga gggtttgata tttgaggttc agcaaggtga tgctttagat      4860
```

```
ttttcatttg ctgctggctc tcagcgtggc actgttgcag gcggtgttaa tactgaccgc   4920
ctcacctctg ttttatcttc tgctggtggt tcgttcggta tttttaatgg cgatgtttta   4980
gggctatcag ttcgcgcatt aaagactaat agccattcaa aatattgtc tgtgccacgt    5040
attcttacgc tttcaggtca aagggttct atctctgttg ccagaatgt ccctttttatt   5100
actggtcgtg tgactggtga atctgccaat gtaaataatc catttcagac gattgagcgt   5160
caaaatgtag gtatttccat gagcgttttt cctgttgcaa tggctggcgg taatattgtt   5220
ctggatatta ccagcaaggc cgatagtttg agttcttcta ctcaggcaag tgatgttatt   5280
actaatcaaa gaagtattgc tacaacggtt aatttgcgtg atggacagac tcttttactc   5340
ggtggcctca ctgattataa aaacacttct caggattctg gcgtaccgtt cctgtctaaa   5400
atcccttaa tcggcctcct gtttagctcc cgctctgatt ctaacgagga agcacgtta    5460
tacgtgctcg tcaaagcaac catagtacgc gccctgtagc ggcgcattaa gcgcggcggg   5520
tgtggtggtt acgcgcagcg tgaccgctac acttgccagc gccctagcgc ccgctccttt   5580
cgctttcttc ccttcctttc tcgccacgtt cgccggcttt ccccgtcaag ctctaaatcg   5640
ggggctccct ttagggttcc gatttagtgc tttacggcac ctcgacccca aaaaacttga   5700
tttgggtgat ggttcacgta gtgggccatc gccctgatag acggttttc gccctttgac    5760
gttggagtcc acgttcttta atagtggact cttgttccaa actggaacaa cactcaaccc   5820
tatctcgggc tattctttg atttataagg gattttgccg atttcggaac caccatcaaa   5880
caggattttc gcctgctggg gcaaaccagc gtggaccgct tgctgcaact ctctcagggc   5940
caggcggtga agggcaatca gctgttgccc gtctcactgg tgaaaagaaa aaccaccctg   6000
gcgcccaata cgcaaaccgc ctctccccgc gcgttggccg attcattaat gcagctggca   6060
cgacaggttt cccgactgga aagcgggcag tgagcgcaac gcaattaatg tgagttagct   6120
cactcattag gcacccagg ctttacactt tatgcttccg gctcgtatgt tgtgtggaat    6180
tgtgagcgga taacaatttc acacaggaaa cagctatgac catgattacg aattcgagct   6240
ctgactactg cttggattct caccaataaa aaacgcccgg cggcaaccga gcgttctgaa   6300
caaatccaga tggagttctg aggtcattac tggatctatc aacaggagtc caagccaatt   6360
ctcgaacgtt tcaattcagc ggcaacgggt tgccgtgata acggctggca aagaacagca   6420
gcggctgggg ggcattcgcc tccggcactc cacaggcgct aacgcgcgca atgaagagcg   6480
tgtggtcgtg tacttcaacc gtgctctcca cctcgcattc gaaccaggcc atggcgtccc   6540
gcagagtggg gaggccggcc tgaactgtga aagcaggagg aggagtgcca tcgatcacac   6600
gcttgctgaa gaatgccgat aacatcttct gactttcacc caggaggctg acgccgaagc   6660
gtccgccttg agtcagcagc tcatgcatac ggcccgactt cagggacacc atcacagtcg   6720
gcgggtccag actgatggag gtgaagctgt tcaccgtcat gccatgcact tcgccctcgt   6780
cagtctccgc gctgagaacc gcaattcccg tcgcgaacag tgcaaccgcc tggcggaagc   6840
tggtggagtc gatatccacc accacatctt tttttaacgt catttgaatc acccaggagt   6900
tagggctccg ctggccttga ccagcggagc aatagcgtca ggccgcaata gtgggtgcgt   6960
actggctgca ccactgaccg atacgttccg ggctggagaa gcgatcccac tgaagttccg   7020
gatagttgaa gttgtccgtg aactcatcag ccatttcacg gctctggctc aggatctgaa   7080
ggaaggtgag gaattccggc ggaagttccg tgaaggcgct cagagtgaag ttggtccagc   7140
gggtggcgca cagcacgcga tcctggcggc gacgctccag gtgttcgctg aagcgcaggt   7200
cgtagacaga gtgcgcaagg atttcctcgc ccagaatcca tgccgcatag gacgccatgt   7260
```

```
tcgcgccctg gcccaagacc ggatcgacag ttgcctggat gtcgcccagc ccgatgatgg   7320
ttttgccgtt attgagggtc gcatgaccgt cgcggaatac tggcacaaca ccgccctgga   7380
ggatgtccag agaactgttg gccaggtcga actcagccgg atcgatgcgc tcggcaacgg   7440
aaggatgatg cttacgcagc ttctccagca tcagatcgag aacgcacgc gggtcatcgt    7500 catacttggt gtgggcgagg acttccagat cgctaccaat atggttttcg agcaccagcg   7560
ctgtgctcat gccattgaac gacagggttg gaatctcaat cagctcgcca tgccctggcg   7620
agaaggacat agtcaccgcg cgaatcggtg cttccttgat gcccttgaag agaccaacgc   7680
acagtgcccg ttgcggcttc tcgaagggcg agttttcgga ctgcttctcg aacaccttgc   7740
cgagggcgta tttaccagtg cacacaacca gcagatcata ctgctccgac agcccttcca   7800
gatcttcggc agacacggcg tcgtagcaga acttgccgcc cctggcttcc agtgcacgca   7860
tcagcatcgg caggtagaga cggtagtcca ctgcacggct gggagccttg agatcaccgt   7920
agaaacgcat gggctgcggc ccacctacgt agtagtagtg gccgaaatag ccaaactcct   7980
cagacggcca ctcattgacg tcgagggcaa cctcccgctg caccgtcacc gcgttgtgag   8040
caacggtatt caggagccgc agtccactgt actcatcggg cttacgatca gtgtacacag   8100
tgacgtcgac gtcatgctgg cggaggaaga ggccaagatg gaggccggca gtgcctgcac   8160
caacaatacc gatacgcttt ttcatgcatg ctacctcctt aatccttcag ctgtatggag   8220
aaacagtaga gagttgcgat aaaaagcgtc aggtatgatc cgctaatctt atggataaaa   8280
atgctatggc atagcaaagt gtgacgccgt gcaaataatc aatgtggact tttctgccgt   8340
gattatagac acttttgtta cgcgcttttg tcatggcttt ggtcccgctt tgttacagaa   8400
tgcttttaat aagcggggtt accggtttgg ttagcgagaa gagccagtaa aagacgcagt   8460
gacggcaatg tctgatgcaa tatggactat tggtttcttg gtacccgggg atcctctaga   8520
gtcgacctgc aggcatgcaa gcttggcact ggccgtcgtt ttacaacgtc gtgactggga   8580
aaaccctggc gttacccaac ttaatcgcct tgcagcacat cccccttttcg ccagctggcg   8640 taatagcgaa gaggcccgca ccgatcgccc ttcccaacag ttgcgcagcc tgaatggcga   8700
atggcgcttt gcctggtttc cggcaccaga agcggtgccg aaagctggc tggagtgcga    8760 tcttcctgag gccgatactg tcgtcgtccc ctcaaactgg cagatgcacg gttacgatgc   8820
gcccatctac accaacgtga cctatcccat tacggtcaat ccgccgtttg ttcccacgga   8880
gaatccgacg ggttgttact cgctcacatt taatgttgat gaaagctggc tacaggaagg   8940
ccagacgcga attattttg atggcgttcc tattggttaa aaaatgagct gatttaacaa    9000
aaatttaatg cgaattttaa caaaatatta cgtttacaa tttaaatatt gcttataca     9060 atcttcctgt ttttgggct tttctgatta tcaaccgggg tacatatgat tgacatgcta    9120
gttttacgat taccgttcat cgattctctt gtttgctcca gactctcagg caatgacctg   9180
atagcctttg tagatctctc aaaaatagct accctctccg gcattaattt atcagctaga   9240
acggttgaat atcatattga tggtgatttg actgtctccg gcctttctca ccctttttgaa  9300 tctttaccta cacattactc aggcattgca tttaaaatat atgagggttc taaaaatttt   9360
tatccttgcg ttgaaataaa ggcttctccc gcaaaagtat tacagggtca taatgttttt   9420
ggtacaaccg atttagcttt atgctctgag gctttattgc ttaattttgc taattctttg   9480
ccttgcctgt atgatttatt ggatgtt                                       9507
```

<210> SEQ ID NO 6

<211> LENGTH: 9295
<212> TYPE: DNA
<213> ORGANISM: Artificial Sequence
<220> FEATURE:
<223> OTHER INFORMATION: Synthetic Polynucleotide

<400> SEQUENCE: 6

| | | | | | |
|---|---|---|---|---|---|
| aatgctacta | ctattagtag | aattgatgcc | acctttcag | ctcgcgcccc | aaatgaaaat | 60 |
| atagctaaac | aggttattga | ccatttgcga | aatgtatcta | atggtcaaac | taaatctact | 120 |
| cgttcgcaga | attgggaatc | aactgttata | tggaatgaaa | cttccagaca | ccgtacttta | 180 |
| gttgcatatt | taaaacatgt | tgagctacag | cattatattc | agcaattaag | ctctaagcca | 240 |
| tccgcaaaaa | tgacctctta | tcaaaaggag | caattaaagg | tactctctaa | tcctgacctg | 300 |
| ttggagtttg | cttccggtct | ggttcgcttt | gaagctcgaa | ttaaaacgcg | atatttgaag | 360 |
| tctttcgggc | ttcctcttaa | tcttttgat | gcaatccgct | ttgcttctga | ctataatagt | 420 |
| cagggtaaag | acctgatttt | tgatttatgg | tcattctcgt | tttctgaact | gtttaaagca | 480 |
| tttgagggg | attcaatgaa | tatttatgac | gattccgcag | tattggacgc | tatccagtct | 540 |
| aaacatttta | ctattacccc | ctctggcaaa | acttctttg | caaaagcctc | tcgctatttt | 600 |
| ggtttttatc | gtcgtctggt | aaacgagggt | tatgatagtg | ttgctcttac | tatgcctcgt | 660 |
| aattcctttt | ggcgttatgt | atctgcatta | gttgaatgtg | gtattcctaa | atctcaactg | 720 |
| atgaatcttt | ctacctgtaa | taatgttgtt | ccgttagttc | gttttattaa | cgtagatttt | 780 |
| tcttcccaac | gtcctgactg | gtataatgag | ccagttctta | aaatcgcata | aggtaattca | 840 |
| caatgattaa | agttgaaatt | aaaccatctc | aagcccaatt | tactactcgt | tctggtgttt | 900 |
| ctcgtcaggg | caagccttat | tcactgaatg | agcagctttg | ttacgttgat | ttgggtaatg | 960 |
| aatatccggt | tcttgtcaag | attactcttg | atgaaggtca | gccagcctat | gcgcctggtc | 1020 |
| tgtacaccgt | tcatctgtcc | tctttcaaag | ttggtcagtt | cggttccctt | atgattgacc | 1080 |
| gtctgcgcct | cgttccggct | aagtaacatg | gagcaggtcg | cggatttcga | cacaattat | 1140 |
| caggcgatga | tacaaatctc | cgttgtactt | tgtttcgcgc | ttggtataat | cgctggggt | 1200 |
| caaagatgag | tgttttagtg | tattcttttg | cctctttcgt | tttaggttgg | tgccttcgta | 1260 |
| gtggcattac | gtatttacc | cgtttaatgg | aaacttcctc | atgaaaaagt | ctttagtcct | 1320 |
| caaagcctct | gtagccgttg | ctaccctcgt | tccgatgctg | tctttcgctg | ctgagggtga | 1380 |
| cgatcccgca | aaagcggcct | ttaactccct | gcaagcctca | gcgaccgaat | atatcggtta | 1440 |
| tgcgtgggcg | atggttgttg | tcattgtcgg | cgcaactatc | ggtatcaagc | tgtttaagaa | 1500 |
| attcacctcg | aaagcaagct | gataaaccga | tacaattaaa | ggctcctttt | ggagcctttt | 1560 |
| ttttggagat | ttcaacgtg | aaaaaattat | tattcgcaat | tcctttagtt | gttccttttct | 1620 |
| attctcactc | cgctgaaact | gttgaaagtt | gtttagcaaa | atcccataca | gaaaattcat | 1680 |
| ttactaacgt | ctggaaagac | gacaaaactt | tagatcgtta | cgctaactat | gagggctgtc | 1740 |
| tgtggaatgc | tacaggcgtt | gtagtttgta | ctggtgacga | aactcagtgt | tacggtacat | 1800 |
| gggttcctat | tgggcttgct | atccctgaaa | atgagggtgg | tggctctgag | ggtggcggtt | 1860 |
| ctgagggtgg | cggttctgag | ggtggcggta | ctaaacctcc | tgagtacggt | gatacaccta | 1920 |
| ttccgggcta | tacttatatc | aaccctctcg | acggcactta | tccgcctggt | actgagcaaa | 1980 |
| accccgctaa | tcctaatcct | tctcttgagg | agtctcagcc | tcttaatact | ttcatgtttc | 2040 |
| agaataatag | gttccgaaat | aggcaggggg | cattaactgt | ttatacgggc | actgttactc | 2100 |
| aaggcactga | ccccgttaaa | acttattacc | agtacactcc | tgtatcatca | aaagccatgt | 2160 |

```
atgacgctta ctggaacggt aaattcagag actgcgcttt ccattctggc tttaatgagg    2220
atttatttgt ttgtgaatat caaggccaat cgtctgacct gcctcaacct cctgtcaatg    2280
ctggcggcgg ctctggtggt ggttctggtg gcggctctga gggtggtggc tctgagggtg    2340
gcggttctga gggtggcggc tctgaggag gcggttccgg tggtggctct ggttccggtg    2400
attttgatta tgaaaagatg gcaaacgcta ataaggggc tatgaccgaa aatgccgatg    2460
aaaacgcgct acagtctgac gctaaaggca aacttgattc tgtcgctact gattacggtg    2520
ctgctatcga tggtttcatt ggtgacgttt ccggccttgc taatggtaat ggtgctactg    2580
gtgattttgc tggctctaat tcccaaatgg ctcaagtcgg tgacggtgat aattcacctt    2640
taatgaataa tttccgtcaa tatttacctt ccctccctca atcggttgaa tgtcgccctt    2700
ttgtctttgg cgctggtaaa ccatatgaat tttctattga ttgtgacaaa ataaacttat    2760
tccgtggtgt ctttgcgttt cttttatatg ttgccacctt tatgtatgta ttttctacgt    2820
ttgctaacat actgcgtaat aaggagtctt aatcatgcca gttcttttgg gtattccgtt    2880
attattgcgt ttcctcggtt tccttctggt aactttgttc ggctatctgc ttacttttct    2940
taaaaagggc ttcggtaaga tagctattgc tatttcattg tttcttgctc ttattattgg    3000
gcttaactca attcttgtgg gttatctctc tgatattagc gctcaattac cctctgactt    3060
tgttcagggt gttcagttaa ttctcccgtc taatgcgctt ccctgttttt atgttattct    3120
ctctgtaaag gctgctattt tcattttga cgttaaacaa aaaatcgttt cttatttgga    3180
ttgggataaa taatatggct gtttattttg taactggcaa attaggctct ggaaagacgc    3240
tcgttagcgt tggtaagatt caggataaaa ttgtagctgg gtgcaaaata gcaactaatc    3300
ttgatttaag gcttcaaaac ctcccgcaag tcgggaggtt cgctaaaacg cctcgcgttc    3360
ttagaatacc ggataagcct tctatatctg atttgcttgc tattgggcgc ggtaatgatt    3420
cctacgatga aaataaaaac ggcttgcttg ttctcgatga gtgcggtact ggtttaata    3480 cccgttcttg gaatgataag gaaagacagc cgattattga ttggtttcta catgctcgta    3540
aattaggatg ggatattatt tttcttgttc aggacttatc tattgttgat aaacaggcgc    3600
gttctgcatt agctgaacat gttgtttatt gtcgtcgtct ggacagaatt actttacctt    3660
ttgtcggtac tttatattct cttattactg gctcgaaaat gcctctgcct aaattacatg    3720
ttggcgttgt aaatatggc gattctcaat taagccctac tgttgagcgt tggctttata    3780
ctggtaagaa tttgtataac gcatatgata ctaaacaggc ttttctagt aattatgatt    3840 ccggtgttta ttcttattta acgccttatt tatcacacgg tcggtatttc aaaccattaa    3900
atttaggtca gaagatgaaa ttaactaaaa tatatttgaa aaagttttct cgcgttcttt    3960
gtcttgcgat tggatttgca tcagcattta catatagtta tataacccaa cctaagccgg    4020
aggttaaaaa ggtagtctct cagacctatg attttgataa attcactatt gactcttctc    4080
agcgtcttaa tctaagctat cgctatgttt tcaaggattc taagggaaaa ttaattaata    4140
gcgacgattt acagaagcaa ggttattcac tcacatatat tgatttatgt actgtttcca    4200
ttaaaaaagg taattcaaat gaaattgtta aatgtaatta attttgtttt cttgatgttt    4260
gtttcatcat cttcttttgc tcaggtaatt gaaatgaata attcgcctct gcgcgatttt    4320
gtaacttggt attcaaagca atcaggcgaa tccgttattg tttctcccga tgtaaaaggt    4380
actgttactg tatattcatc tgacgttaaa cctgaaaatc tacgcaattt ctttatttct    4440
gttttacgtg caaataattt tgatatggta ggttctaacc cttccattat tcagaagtat    4500
```

```
aatccaaaca atcaggatta tattgatgaa ttgccatcat ctgataatca ggaatatgat    4560
gataattccg ctccttctgg tggtttcttt gttccgcaaa atgataatgt tactcaaact    4620
tttaaaatta ataacgttcg ggcaaaggat ttaatacgag ttgtcgaatt gtttgtaaag    4680
tctaatactt ctaaatcctc aaatgtatta tctattgacg gctctaatct attagttgtt    4740
agtgctccta aagatatttt agataacctt cctcaattcc tttcaactgt tgatttgcca    4800
actgaccaga tattgattga gggtttgata tttgaggttc agcaaggtga tgctttagat    4860
ttttcatttg ctgctggctc tcagcgtggc actgttgcag gcggtgttaa tactgaccgc    4920
ctcacctctg ttttatcttc tgctggtggt tcgttcggta tttttaatgg cgatgtttta    4980
gggctatcag ttcgcgcatt aaagactaat agccattcaa aaatattgtc tgtgccacgt    5040
attcttacgc tttcaggtca aaggggttct atctctgttg gccagaatgt ccctttttatt    5100 actggtcgtg tgactggtga atctgccaat gtaaataatc catttcagac gattgagcgt    5160
caaaatgtag gtatttccat gagcgttttt cctgttgcaa tggctggcgg taatattgtt    5220
ctggatatta ccagcaaggc cgatagtttg agttcttcta ctcaggcaag tgatgttatt    5280
actaatcaaa gaagtattgc tacaacggtt aatttgcgtg atggacagac tctttttactc    5340 ggtggcctca ctgattataa aaacacttct caggattctg gcgtaccgtt cctgtctaaa    5400 atcccttttaa tcggcctcct gtttagctcc cgctctgatt ctaacgagga aagcacgtta    5460
tacgtgctcg tcaaagcaac catagtacgc gccctgtagc ggcgcattaa gcgcggcggg    5520
tgtggtggtt acgcgcagcg tgaccgctac acttgccagc gccctagcgc ccgctccttt    5580
cgctttcttc ccttcctttc tcgccacgtt cgccggcttt ccccgtcaag ctctaaatcg    5640
ggggctccct ttagggttcc gatttagtgc tttacggcac ctcgacccca aaaaacttga    5700
tttgggtgat ggttcacgta gtgggccatc gccctgatag acggtttttc gccctttgac    5760
gttggagtcc acgttcttta atagtggact cttgttccaa actggaacaa cactcaaccc    5820
tatctcgggc tattcttttg atttataagg gattttgccg atttcggaac caccatcaaa    5880
caggattttc gcctgctggg gcaaaccagc gtggaccgct tgctgcaact ctctcagggc    5940
caggcggtga agggcaatca gctgttgccc gtctcactgg tgaaaagaaa aaccaccctg    6000
gcgcccaata cgcaaaccgc ctctccccgc gcgttggccg attcattaat gcagctggca    6060
cgacaggttt cccgactgga aagcgggcag tgagcgcaac gcaattaatg tgagttagct    6120
cactcattag gcaccccagg ctttacactt tatgcttccg gctcgtatgt tgtgtggaat    6180
tgtgagcgga taacaatttc acacaggaaa cagctatgac catgattacg aattcgagct    6240
ctgactactg cttggattct caccaataaa aaacgcccgg cggcaaccga gcgttctgaa    6300
caaatccaga tggagttctg aggtcattac tggatctatc aacaggagtc caagccaatt    6360
ctcgaacgtt tcaattcagc ggcaacgggt tgccgtgata acggctggca agaacagca    6420 gcggctgggg ggcattcgcc tccggcactc cacaggcgct aacgcgcgca atgaagagcg    6480
tgtggtcgtg tacttcaacc gtgctctcca cctcgcattc gaaccaggcc atggcgtccc    6540
gcagagtggg gaggccggcc tgaactgtga aagcaggagg aggagtgcca tcgatcacac    6600
gcttgctgaa gaatgccgat aacatcttct gactttcacc caggaggctg acgccgaagc    6660
gtccgccttg agtcagcagc tcatgcatac ggcccgactt cagggacacc atcacagtcg    6720
gcgggtccag actgatggag gtgaagctgt tcaccgtcat gccatgcact tcgccctcgt    6780
cagtctccgc gctgagaacc gcaattcccg tcgcgaacag tgcaaccgcc tggcggaagc    6840
tggtggagtc gatatccacc accacatctt tttttaacgt catttgaatc acccaggagt    6900
```

```
tagggctccg ctggccttga ccagcggagc aatagcgtca ggccgcaata gtgggtgcgt    6960
actggctgca ccactgaccg atacgttccg ggctggagaa gcgatcccac tgaagttccg    7020
gatagttgaa gttgtccgtg aactcatcag ccatttcacg gctctggctc aggatctgaa    7080
ggaaggtgag gaattccggc ggaagttccg tgaaggcgct cagagtgaag ttggtccagc    7140
gggtggcgca cagcacgcga tcctggcggc gacgctccag gtgttcgctg aagcgcaggt    7200
cgtagacaga gtgcgcaagg atttcctcgc ccagaatcca tgccgcatag gacgccatgt    7260
tcgcgccctg gcccaagacc ggatcgacag ttgcctggat gtcgcccagc ccgatgatgg    7320
ttttgccgtt attgagggtc gcatgaccgt cgcggaatac tggcacaaca ccgccctgga    7380
ggatgtccag agaactgttg gccaggtcga actcagccgg atcgatgcgc tcggcaacgg    7440
aaggatgatg cttacgcagc ttctccagca tcagatcgag gaacgcacgc gggtcatcgt    7500
catacttggt gtgggcgagg acttccagat cgctaccaat atggttttcg agcaccagcg    7560
ctgtgctcat gccattgaac gacagggttg gaatctcaat cagctcgcca tgccctggcg    7620
agaaggacat agtcaccgcg cgaatcggtg cttccttgat gcccttgaag agaccaacgc    7680
acagtgcccg ttgcggcttc tcgaagggcg agttttcgga ctgcttctcg aacaccttgc    7740
cgagggcgta tttaccagtg cacacaacca gcagatcata ctgctccgac agcccttcca    7800
gatcttcggc agacacggcg tcgtagcaga acttgccgcc cctggcttcc agtgcacgca    7860
tcagcatcgg caggtagaga cggtagtcca ctgcacggct gggagccttg agatcaccgt    7920
agaaacgcat gggctgcggc ccacctacgt agtagtagtg gccgaaatag ccaaactcct    7980
cagacggcca ctcattgacg tcgagggcaa cctcccgctg caccgtcacc gcgttgtgag    8040
caacggtatt caggagccgc agtccactgt actcatcggg cttacgatca gtgtacacag    8100
tgacgtcgac gtcatgctgg cggaggaaga ggccaagatg gaggccggca gtgcctgcac    8160
caacaatacc gatacgcttt ttcatgcatg ctacctcctt aatccttcag ctgggtcagt    8220
gcgtcctgct gatgtgctca gtatctctat cactgatagg gatgtcaatc tctatcactg    8280
atagggaggt acccggggat cctctagagt cgacctgcag gcatgcaagc ttggcactgg    8340
ccgtcgtttt acaacgtcgt gactgggaaa accctggcgt tacccaactt aatcgccttg    8400
cagcacatcc cctttcgcc agctggcgta atagcgaaga ggcccgcacc gatcgccctt    8460
cccaacagtt gcgcagcctg aatggcgaat ggcgctttgc ctggtttccg gcaccagaag    8520
cggtgccgga agctggctg gagtgcgatc ttcctgaggc cgatactgtc gtcgtcccct    8580
caaactggca gatgcacggt tacgatgcgc ccatctacac caacgtgacc tatcccatta    8640
cggtcaatcc gccgtttgtt cccacggaga atccgacggg ttgttactcg ctcacattta    8700
atgttgatga agctggcta caggaaggcc agacgcgaat tatttttgat ggcgttccta    8760
ttggttaaaa aatgagctga tttaacaaaa atttaatgcg aattttaaca aaatattaac    8820
gtttacaatt taaatatttg cttatacaat cttcctgttt ttggggcttt tctgattatc    8880
aaccggggta catatgattg acatgctagt tttacgatta ccgttcatcg attctcttgt    8940
ttgctccaga ctctcaggca atgacctgat agcctttgta gatctctcaa aaatagctac    9000
cctctccggc attaatttat cagctagaac ggttgaatat catattgatg gtgatttgac    9060
tgtctccggc ctttctcacc cttttgaatc tttacctaca cattactcag gcattgcatt    9120
taaaatatat gagggttcta aaaatttttta tccttgcgtt gaaataaagg cttctcccgc    9180
aaaagtatta cagggtcata atgttttggg tacaaccgat ttagctttat gctctgaggc    9240
```
tttattgctt aatttgcta attctttgcc ttgcctgtat gatttattgg atgtt    9295

<210> SEQ ID NO 7
<211> LENGTH: 3101
<212> TYPE: DNA
<213> ORGANISM: Artificial Sequence
<220> FEATURE:
<223> OTHER INFORMATION: Synthetic Polynucleotide

<400> SEQUENCE: 7
gacgtctgtg caagtactac tgttctgcag tcacttgaat tcgataccca gctgggtgga     60
gtgcaccaag gagcatgcga aggaaacgtt tcgcagaagc ttccgcaagg taccactttg    120
ccgcggagta tttgtacatt tgaaggatcc tcaagtcggc cgcccgttcc atggatactc    180
gtcgaccatt acgctagccg tctggagctc ggactgctta agtcgctcca tatgctgaaa    240
tgagctgttg acaattaatc atccggctcg tataatgtgt ggaattgtga gcggataaca    300
atttcacacc ccgggataag gaggacaatt gatgcgtaaa ggagaagaac ttttcactgg    360
agttgtccca attcttgttg aattagatgg tgatgttaat gggcacaaat tttctgtcag    420
tggagagggt gaaggtgatg caacatacgg aaaacttacc cttaaattta tttgcactac    480
tggaaaacta cctgttccgt ggccaacact tgtcactact ttcggttatg tgttcaatg    540
ctttgcgaga tacccagatc acatgaaaca gcatgacttt ttcaagagtg ccatgcccga    600
aggttacgta caggaaagaa ctatattttt caaagatgac gggaactaca agacacgtgc    660
tgaagtcaag tttgaaggtg ataccccttgt taatagaatc gagttaaaag gtattgattt    720
taaagaagat ggaaacattc ttggacacaa attggaatac aactataact cacacaatgt    780
atacatcatg gcagacaaac aaaagaatgg aatcaaagtt aacttcaaaa ttagacacaa    840
cattgaagat ggaagcgttc aactagcaga ccattatcaa caaaatactc cgattggcga    900
tggccctgtc cttttaccag acaaccatta cctgtccaca caatctgccc tttcgaaaga    960
tcccaacgaa aagagagacc acatggtcct tcttgagttt gtaaccgctg ctgggattac   1020
acatggcatg gatgaactat acaaataagg cgccagggtt gatatctatc gccctaggga   1080
ccgtctcgag agaatcaata ttaatccaac gcgtggcatc aaataaaacg aaaggctcag   1140
tcgaaagact gggcctttcg ttttatctgt tgtttgtcgg tgaacgctct cctgagtagg   1200
acaaatccgc cgccctagac ttaggcgttc ggctgcggcg agcggtatca gctcactcaa   1260
aggcggtaat acggttatcc acagaatcag gggataacgc aggaaagaac atgtgagcaa   1320
aaggccagca aaaggccagg aaccgtaaaa aggccgcgtt gctggcgttt ttccataggc   1380
tccgcccccc tgacgagcat cacaaaaatc gacgctcaag tcagaggtgg cgaaacccga   1440
caggactata agataccagg cgtttccccc ctggaagctc cctcgtgcgc tctcctgttc   1500
cgaccctgcc gcttaccgga tacctgtccg cctttctccc ttcgggaagc gtggcgcttt   1560
ctcatagctc acgctgtagg tatctcagtt cggtgtaggt cgttcgctcc aagctgggct   1620
gtctgcacga accccccgtt cagcccgacc gctgcgcctt atccggtaac tatcgtcttg   1680
agtccaaccc ggtaagacac gacttatcgc cactggcagc agccactggt aacaggatta   1740
gcagagcgag gtatgtaggc ggtgctacag agttcttgaa gtggtggcct aactacggct   1800
acactagaag gacagtattt ggtatctgcg ctctgctgaa gccagttacc ttcggaaaaa   1860
gagttggtag ctcttgatcc ggcaaacaaa ccaccgctgg tagcggtggt ttttttgttt   1920
gcaagcagca gattacgcgc agaaaaaaag gatctcaaga atccttg atcttttcta   1980
cggggtctga cgctcagtgg aacgaaaact cacgttaagg gattttggtc atggctagtg   2040

| | |
|---|---:|
| cttggattct caccaataaa aaacgcccgg cggcaaccga gcgttctgaa caaatccaga | 2100 |
| tggagttctg aggtcattac tggatctatc aacaggagtc caagccaatt ctcgaacccc | 2160 |
| agagtcccgc tcagaagaac tcgtcaagaa ggcgatagaa ggcgatgcgc tgcgaatcgg | 2220 |
| gagcggcgat accgtaaagc acgaggaagc ggtcagccca ttcgccgcca agctcttcag | 2280 |
| caatatcacg ggtagccaac gctatgtcct gatagcggtc cgccacaccc agccggccac | 2340 |
| agtcgatgaa tccagaaaag cggccatttt ccaccatgat attcggcaag caggcatcgc | 2400 |
| cgtgggtcac gacgagatcc tcgccgtcgg gcatacgcgc cttgagcctg gcgaacagtt | 2460 |
| cggctggcgc gagcccctga tgctcttcgt ccagatcatc ctgatcgaca gaccggcttt | 2520 |
| ccatccgagt acgtgctcgc tcgatgcgat gtttcgcttg gtggtcgaat gggcaggtag | 2580 |
| ccggatcaag cgtatgcagc cgccgcattg catcagccat gatggatact ttctcggcag | 2640 |
| gagcaaggtg agatgacagg agatcctgcc ccggcacttc gcccaatagc agccagtccc | 2700 |
| ttcccgcttc agtgacaacg tcgagcacag ccgcgcaagg aacgcccgtc gtggccagcc | 2760 |
| acgatagccg cgctgcctcg tcttgcagtt cattcagggc accggacagg tcggtcttga | 2820 |
| caaaaagaac cgggcgaccc tgcgctgaca gccggaacac ggcggcatca gagcagccga | 2880 |
| ttgtctgttg tgcccagtca tagccgaata gcctctccac ccaagccgcc ggagaacctg | 2940 |
| cgtgcaatcc atcttgttca atcatgcgaa acgatcctca tcctgtctct tgatcagatc | 3000 |
| ttgatcccct gcgccatcag atccttggcg gcaagaaagc catccagttt actttgcagg | 3060 |
| gcttcccaac cttaccagag ggcggcccaa ctggcaattc c | 3101 |

```
<210> SEQ ID NO 8
<211> LENGTH: 3524
<212> TYPE: DNA
<213> ORGANISM: Artificial Sequence
<220> FEATURE:
<223> OTHER INFORMATION: Synthetic Polynucleotide

<400> SEQUENCE: 8
```

| | |
|---|---:|
| gacgtctgtg caagtactac tgttctgcag tcacttgaat tcgatacccca gctgggtgga | 60 |
| gtgcaccaag gagcatgcga aggaaacgtt tcgcagaagc ttccgcaagg taccactttg | 120 |
| ccgcggagta tttgtacatt tgaaggatcc tcaagtcggc cgcccgttcc atggatactc | 180 |
| gtcgaccatt acgctagccg tctggagctc ggactgctta agtcgctcca tatgctgaaa | 240 |
| tgagctgttg acaattaatc atccggctcg tataatgtgt ggaattgtga gcggataaca | 300 |
| atttcacacc ccgggataag gaggacaatt gatgcgtaaa ggagaagaac ttttcactgg | 360 |
| agttgtccca attcttgttg aattagatgg tgatgttaat gggcacaaat tttctgtcag | 420 |
| tggagagggt gaaggtgatg caacatacgg aaaacttacc cttaaattta tttgcactac | 480 |
| tggaaaacta cctgttccgt ggccaacact tgtcactact ttcggttatg gtgttcaatg | 540 |
| ctttgcgaga tacccagatc acatgaaaca gcatgacttt ttcaagagtg ccatgcccga | 600 |
| aggttacgta caggaaagaa ctatattttt caaagatgac gggaactaca agacacgtgc | 660 |
| tgaagtcaag tttgaaggtg atacccttgt taatagaatc gagttaaaag gtattgattt | 720 |
| taaagaagat ggaaacattc ttggacacaa attggaatac aactataact cacacaatgt | 780 |
| atacatcatg gcagacaaac aaaagaatgg aatcaaagtt aacttcaaaa ttagacacaa | 840 |
| cattgaagat ggaagcgttc aactagcaga ccattatcaa caaaatactc cgattggcga | 900 |
| tggccctgtc cttttaccag acaaccatta cctgtccaca caatctgccc tttcgaaaga | 960 |

```
tcccaacgaa aagagagacc acatggtcct tcttgagttt gtaaccgctg ctgggattac    1020
acatggcatg gatgaactat acaaataagg cgccagggtt gatatctatc gccctaggga    1080
ccgtctcgag agcgccctgt agcggcgcat taagcgcggc gggtgtggtg gttacgcgca    1140
gcgtgaccgc tacacttgcc agcgcccta g cgcccgctcc tttcgctttc ttcccttcct    1200
ttctcgccac gttcgccggc tttccccgtc aagctctaaa tcggggctc cctttagggt      1260 tccgatttag tgctttacgg cacctcgacc ccaaaaaact tgattaggt gatggttcac     1320 gtagtgggcc atcgccctga tagacggttt ttcgcccttt gacgttggag tccacgttct    1380
ttaatagtgg actcttgttc caaactggaa caacactcaa ccctatctcg gtctattctt    1440
ttgatttata agggattttg ccgatttcgg cctattggtt aaaaaatgag ctgatttaac    1500
aaaaatttaa cgcgaattaa atattaatcc aacgcgtggc atcaaataaa acgaaaggct    1560
cagtcgaaag actgggcctt tcgttttatc tgttgtttgt cggtgaacgc tctcctgagt    1620
aggacaaatc cgccgcccta gacttaggcg ttcggctgcg gcgagcggta tcagctcact    1680
caaaggcggt aatacggtta tccacagaat caggggataa cgcaggaaag aacatgtgag    1740
caaaaggcca gcaaaaggcc aggaaccgta aaaaggccgc gttgctggcg ttttttccata    1800 ggctccgccc cctgacgag catcacaaaa atcgacgctc aagtcagagg tggcgaaacc    1860
cgacaggact ataaagatac caggcgtttc ccctggaag ctccctcgtg cgctctcctg     1920
ttccgaccct gccgcttacc ggatacctgt ccgcctttct cccttcggga agcgtggcgc    1980
tttctcatag ctcacgctgt aggtatctca gttcggtgta ggtcgttcgc tccaagctgg    2040
gctgtctgca cgaaccccc gttcagcccg accgctgcgc cttatccggt aactatcgtc    2100
ttgagtccaa cccggtaaga cacgacttat cgccactggc agcagccact ggtaacagga    2160
ttagcagagc gaggtatgta ggcggtgcta cagagttctt gaagtggtgg cctaactacg    2220
gctacactag aaggacagta tttggtatct gcgctctgct gaagccagtt accttcggaa    2280
aaagagttgg tagctcttga tccggcaaac aaaccaccgc tggtagcggt ggtttttttg    2340
tttgcaagca gcagattacg cgcagaaaaa aaggatctca agaagatcct ttgatctttt    2400
ctacggggtc tgacgctcag tggaacgaaa actcacgtta agggattttg gtcatggcta    2460
gtgcttggat tctcaccaat aaaaaacgcc cggcggcaac cgagcgttct gaacaaatcc    2520
agatggagtt ctgaggtcat tactggatct atcaacagga gtccaagcca attctcgaac    2580
cccagagtcc cgctcagaag aactcgtcaa gaaggcgata gaaggcgatg cgctgcgaat    2640
cgggagcggc gataccgtaa agcacgagga gccggtcagc ccattcgccg ccaagctctt    2700
cagcaatatc acgggtagcc aacgctatgt cctgatagcg gtccgccaca cccagccggc    2760
cacagtcgat gaatccagaa aagcggccat tttccaccat gatattcggc aagcaggcat    2820
cgccgtgggt cacgacgaga tcctcgccgt cgggcatacg cgccttgagc ctggcgaaca    2880
gttcggctgg cgcgagcccc tgatgctctt cgtccagatc atcctgatcg acaagaccgg    2940
cttccatccg agtacgtgct cgctcgatgc gatgtttcgc ttggtggtcg aatgggcagg    3000
tagccggatc aagcgtatgc agccgccgca ttgcatcagc catgatggat actttctcgg    3060
caggagcaag gtgagatgac aggagatcct gccccgcac ttcgcccaat agcagccagt    3120
cccttcccgc ttcagtgaca acgtcgagca cagccgcgca aggaacgccc gtcgtggcca    3180
gccacgatag ccgcgctgcc tcgtcttgca gttcattcag ggcaccggac aggtcggtct    3240
tgacaaaaag aaccgggcga ccctgcgctg acagccggaa cacggcggca tcagagcagc    3300
cgattgtctg ttgtgcccag tcatagccga atagcctctc cacccaagcc gccggagaac    3360
```

```
ctgcgtgcaa tccatcttgt tcaatcatgc gaaacgatcc tcatcctgtc tcttgatcag    3420
atcttgatcc cctgcgccat cagatccttg gcggcaagaa agccatccag tttactttgc    3480
agggcttccc aaccttacca gagggcggcc caactggcaa ttcc                     3524

<210> SEQ ID NO 9
<211> LENGTH: 7413
<212> TYPE: DNA
<213> ORGANISM: Artificial Sequence
<220> FEATURE:
<223> OTHER INFORMATION: Synthetic Polynucleotide

<400> SEQUENCE: 9
aatgctacta ctattagtag aattgatgcc accttttcag ctcgcgcccc aaatgaaaat      60
atagctaaac aggttattga ccatttgcga aatgtatcta atggtcaaac taaatctact     120
cgttcgcaga attgggaatc aactgttata tggaatgaaa cttccagaca ccgtactta     180 gttgcatatt taaaacatgt tgagctacag cattatattc agcaattaag ctctaagcca    240
tccgcaaaaa tgacctctta tcaaaaggag caattaaagg tactctctaa tcctgacctg    300
ttggagtttg cttccggtct ggttcgcttt gaagctcgaa ttaaaacgcg atatttgaag    360
tctttcgggc ttcctcttaa tctttttgat gcaatccgct ttgcttctga ctataatagt    420
cagggtaaag acctgatttt tgatttatgg tcattctcgt tttctgaact gtttaaagca    480
tttgaggggg attcaatgaa tatttatgac gattccgcag tattggacgc tatccagtct    540
aaacatttta ctattacccc ctctggcaaa acttctttg caaagcctc tcgctatttt    600 ggtttttatc gtcgtctggt aaacgagggt tatgatagtg ttgctcttac tatgcctcgt    660
aattcctttt ggcgttatgt atctgcatta gttgaatgtg gtattcctaa atctcaactg    720
atgaatcttt ctacctgtaa taatgttgtt ccgttagttc gttttattaa cgtagatttt    780
tcttcccaac gtcctgactg gtataatgag ccagttctta aaatcgcata aggtaattca    840
caatgattaa agttgaaatt aaaccatctc aagcccaatt tactactcgt tctggtgttt    900
ctcgtcaggg caagccttat tcactgaatg agcagctttg ttacgttgat ttgggtaatg    960
aatatccggt tcttgtcaag attactcttg atgaaggtca gccagcctat gcgcctggtc   1020
tgtacaccgt tcatctgtcc tctttcaaag ttggtcagtt cggttccctt atgattgacc   1080
gtctgcgcct cgttccggct aagtaacatg gagcaggtcg cggatttcga cacaatttat   1140
caggcgatga tacaaatctc cgttgtactt tgtttcgcgc ttggtataat cgctgggggt   1200
caaagatgag tgttttagtg tattcttttg cctctttcgt tttaggttgg tgccttcgta   1260
gtggcattac gtattttacc cgtttaatgg aaacttcctc atgaaaaagt ctttagtcct   1320
caaagcctct gtagccgttg ctaccctcgt tccgatgctg tctttcgctg ctgagggtga   1380
cgatcccgca aaagcggcct ttaactccct gcaagcctca gcgaccgaat atatcggtta   1440
tgcgtgggcg atggttgttg tcattgtcgg cgcaactatc ggtatcaagc tgtttaagaa   1500
attcacctcg aaagcaagct gataaaccga tacaattaaa ggctcctttt ggagcctttt   1560
ttttggagat tttcaacgtg aaaaaattat tattcgcaat tcctttagtt gttcctttct   1620
attctcactc cgctgaaact gttgaaagtt gtttagcaaa atcccataca gaaaattcat   1680
ttactaacgt ctggaaagac gacaaaactt tagatcgtta cgctaactat gagggctgtc   1740
tgtggaatgc tacaggcgtt gtagtttgta ctggtgacga aactcagtgt tacggtacat   1800
gggttcctat tgggcttgct atccctgaaa atgagggtgg tggctctgag ggtggcggtt   1860
```

```
ctgagggtgg cggttctgag ggtggcggta ctaaacctcc tgagtacggt gatacaccta   1920
ttccgggcta tacttatatc aaccctctcg acggcactta tccgcctggt actgagcaaa   1980
accccgctaa tcctaatcct tctcttgagg agtctcagcc tcttaatact ttcatgtttc   2040
agaataatag gttccgaaat aggcaggggg cattaactgt ttatacgggc actgttactc   2100
aaggcactga ccccgttaaa acttattacc agtacactcc tgtatcatca aaagccatgt   2160
atgacgctta ctggaacggt aaattcagag actgcgcttt ccattctggc tttaatgagg   2220
atttatttgt ttgtgaatat caaggccaat cgtctgacct gcctcaacct cctgtcaatg   2280
ctggcggcgg ctctggtggt ggttctggtg gcggctctga gggtggtggc tctgagggtg   2340
gcggttctga gggtggcggc tctgagggag gcggttccgg tggtggctct ggttccggtg   2400
attttgatta tgaaaagatg gcaaacgcta ataaggggc tatgaccgaa atgccgatg    2460
aaaacgcgct acagtctgac gctaaaggca aacttgattc tgtcgctact gattacggtg   2520
ctgctatcga tggtttcatt ggtgacgttt ccggccttgc taatggtaat ggtgctactg   2580
gtgattttgc tggctctaat tcccaaatgg ctcaagtcgg tgacggtgat aattcacctt   2640
taatgaataa tttccgtcaa tatttacctt ccctccctca atcggttgaa tgtcgccctt   2700
ttgtctttgg cgctggtaaa ccatatgaat tttctattga ttgtgacaaa ataaacttat   2760
tccgtggtgt ctttgcgttt ctttatatg ttgccacctt tatgtatgta ttttctacgt    2820
ttgctaacat actgcgtaat aaggagtctt aatcatgcca gttcttttgg gtattccgtt   2880
attattgcgt ttcctcggtt tccttctggt aactttgttc ggctatctgc ttacttttct   2940
taaaagggc ttcggtaaga tagctattgc tatttcattg tttcttgctc ttattattgg    3000
gcttaactca attcttgtgg gttatctctc tgatattagc gctcaattac cctctgactt   3060
tgttcagggt gttcagttaa ttctcccgtc taatgcgctt ccctgttttt atgttattct   3120
ctctgtaaag gctgctattt tcattttga cgttaaacaa aaaatcgttt cttatttgga    3180
ttgggataaa taatatggct gtttattttg taactggcaa attaggctct ggaaagacgc   3240
tcgttagcgt tggtaagatt caggataaaa ttgtagctgg gtgcaaaata gcaactaatc   3300
ttgatttaag gcttcaaaac ctcccgcaag tcggaggtt cgctaaaacg cctcgcgttc    3360
ttagaatacc ggataagcct tctatatctg atttgcttgc tattgggcgc ggtaatgatt   3420
cctacgatga aaataaaaac ggcttgcttg ttctcgatga gtgcggtact ggtttaata    3480
cccgttcttg gaatgataag gaaagacagc cgattattga ttggtttcta catgctcgta   3540
aattaggatg ggatattatt tttccttgttc aggacttatc tattgttgat aaacaggcgc   3600
gttctgcatt agctgaacat gttgtttatt gtcgtcgtct ggacagaatt actttacctt   3660
ttgtcggtac tttatattct cttattactg gctcgaaaat gcctctgcct aaattacatg   3720
ttggcgttgt aaatatggc gattctcaat taagccctac tgttgagcgt tggctttata    3780
ctggtaagaa tttgtataac gcatatgata ctaaacaggc tttttctagt aattatgatt   3840
ccggtgttta ttcttattta acgccttatt tatcacacgg tcggtatttc aaaccattaa   3900
atttaggtca gaagatgaaa ttaactaaaa tatatttgaa aaagttttct cgcgttcttt   3960
gtcttgcgat tggatttgca tcagcattta catagttta tataacccaa cctaagccgg   4020
aggttaaaaa ggtagtctct cagacctatg attttgataa attcactatt gactcttctc   4080
agcgtcttaa tctaagctat cgctatgttt tcaaggattc taagggaaaa ttaattaata   4140
gcgacgattt acagaagcaa ggttattcac tcacatatat tgatttatgt actgtttcca   4200
ttaaaaaagg taattcaaat gaaattgtta aatgtaatta attttgtttt cttgatgttt   4260
```

```
gtttcatcat cttcttttgc tcaggtaatt gaaatgaata attcgcctct gcgcgatttt    4320
gtaacttggt attcaaagca atcaggcgaa tccgttattg tttctcccga tgtaaaaggt    4380
actgttactg tatattcatc tgacgttaaa cctgaaaatc tacgcaattt ctttatttct    4440
gttttacgtg caaataattt tgatatggta ggttctaacc cttccattat tcagaagtat    4500
aatccaaaca atcaggatta tattgatgaa ttgccatcat ctgataatca ggaatatgat    4560
gataattccg ctccttctgg tggtttcttt gttccgcaaa atgataatgt tactcaaact    4620
tttaaaatta ataacgttcg ggcaaaggat ttaatacgag ttgtcgaatt gtttgtaaag    4680
tctaatactt ctaaatcctc aaatgtatta tctattgacg gctctaatct attagttgtt    4740
agtgctccta aagatatttt agataaacctt cctcaattcc tttcaactgt tgatttgcca    4800
actgaccaga tattgattga gggttttgata tttgaggttc agcaaggtga tgctttagat    4860
ttttcatttg ctgctggctc tcagcgtggc actgttgcag gcggtgttaa tactgaccgc    4920
ctcacctctg ttttatcttc tgctggtggt tcgttcggta tttttaatgg cgatgtttta    4980
gggctatcag ttcgcgcatt aaagactaat agccattcaa aaatattgtc tgtgccacgt    5040
attcttacgc tttcaggtca aaggggttct atctctgttg gccagaatgt ccctttttatt    5100 actggtcgtg tgactggtga atctgccaat gtaaataatc catttcagac gattgagcgt    5160
caaaatgtag gtatttccat gagcgttttt cctgttgcaa tggctggcgg taatattgtt    5220
ctggatatta ccagcaaggc cgatagtttg agttcttcta ctcaggcaag tgatgttatt    5280
actaatcaaa gaagtattgc tacaacggtt aatttgcgtg atggacagac tcttttactc    5340
ggtggcctca ctgattataa aaacacttct caggattctg gcgtaccgtt cctgtctaaa    5400
atccctttaa tcggcctcct gtttagctcc cgctctgatt ctaacgagga aagcacgtta    5460
tacgtgctcg tcaaagcaac catagtacgc gccctgtagc ggcgcattaa gcgcggcggg    5520
tgtggtggtt acgcgcagcg tgaccgctac acttgccagc gccctagcgc ccgctccttt    5580
cgctttcttc ccttcctttc tcgccacgtt cgccggcttt ccccgtcaag ctctaaatcg    5640
ggggctccct ttagggttcc gatttagtgc tttacggcac ctcgaccccca aaaaacttga    5700 tttgggtgat ggttcacgta gtgggccatc gccctgatag acggttttc gccctttgac    5760 gttggagtcc acgttcttta atagtggact cttgttccaa actggaacaa cactcaaccc    5820
tatctcgggc tattcttttg atttataagg gattttgccg atttcgggac tgcttaagtc    5880
gctccatatg ctgaaatgag ctgttgacaa ttaatcatcc ggctcgtata atgtgtggaa    5940
ttgtgagcgg ataacaattt cacacccccgg gataaggagg acaattgatg cgtaaaggag    6000
aagaactttt cactggagtt gtcccaattc ttgttgaatt agatggtgat gttaatgggc    6060
acaaattttc tgtcagtgga gagggtgaag gtgatgcaac atacggaaaa cttacccta    6120 aatttatttg cactactgga aaactacctg ttccgtggcc aacacttgtc actactttcg    6180
gttatggtgt tcaatgcttt gcgagatacc cagatcacat gaaacagcat gactttttca    6240
agagtgccat gcccgaaggt tacgtacagg aaagaactat attttttcaaa gatgacggga    6300 actacaagac acgtgctgaa gtcaagtttg aaggtgatac ccttgttaat agaatcgagt    6360
taaaaggtat tgattttaaa gaagatggaa acattcttgg acacaaattg gaatacaact    6420
ataactcaca caatgtatac atcatggcag acaaacaaaa gaatggaatc aaagttaact    6480
tcaaaattag acacaacatt gaagatggaa gcgttcaact agcagaccat tatcaacaaa    6540
atactccgat tggcgatggc cctgtccttt taccagacaa ccattacctg tccacacaat    6600
```

```
                                              -continued
ctgcccttc  gaaagatccc  aacgaaaaga  gagaccacat  ggtccttctt  gagtttgtaa  6660
ccgctgctgg  gattacacat  ggcatggatg  aactatacaa  ataaggcgcc  agggttgata  6720
tctatcgccc  tagggaccgt  ctcgagagaa  tcaatattaa  tccaacgcgt  ggcatcaaat  6780
aaaacgaaag  gctcagtcga  aagactgggc  ctttcgtttt  atctgttgtt  tgtcggtgaa  6840
cgctctcctg  agtaggacaa  atccgccgcc  ctagactatt  ggttaaaaaa  tgagctgatt  6900
taacaaaaat  ttaatgcgaa  ttttaacaaa  atattaacgt  ttacaattta  aatatttgct  6960
tatacaatct  tcctgttttt  ggggcttttc  tgattatcaa  ccggggtaca  tatgattgac  7020
atgctagttt  tacgattacc  gttcatcgat  tctcttgttt  gctccagact  ctcaggcaat  7080
gacctgatag  cctttgtaga  tctctcaaaa  atagctaccc  tctccggcat  taatttatca  7140
gctagaacgg  ttgaatatca  tattgatggt  gatttgactg  tctccggcct  ttctcaccct  7200
tttgaatctt  tacctacaca  ttactcaggc  attgcattta  aaatatatga  gggttctaaa  7260
aatttttatc  cttgcgttga  aataaaggct  tctcccgcaa  aagtattaca  gggtcataat  7320
gtttttggta  caaccgattt  agctttatgc  tctgaggctt  tattgcttaa  ttttgctaat  7380
tctttgcctt  gcctgtatga  tttattggat  gtt                     7413
```